United States Patent
Holmström et al.

(10) Patent No.: US 11,556,018 B2
(45) Date of Patent: Jan. 17, 2023

(54) OPHTHALMIC MULTIFOCAL DIFFRACTIVE LENS

(71) Applicant: VSY Biyoteknoloji ve Ilaç San. A.S., Istanbul (TR)

(72) Inventors: Sven Thage Sigvard Holmström, Istanbul (TR); Isa Çim, Istanbul (TR); Hakan Urey, Istanbul (TR)

(73) Assignee: VSY BIYOTEKNOLOJI VE ILAÇ SAN. A.S., Istanbul (TR)

( * ) Notice: Subject to any disclaimer, the term of this patent is extended or adjusted under 35 U.S.C. 154(b) by 418 days.

(21) Appl. No.: 16/633,975

(22) PCT Filed: Jul. 17, 2018

(86) PCT No.: PCT/EP2018/069391
§ 371 (c)(1),
(2) Date: Jan. 24, 2020

(87) PCT Pub. No.: WO2019/020435
PCT Pub. Date: Jan. 31, 2019

(65) Prior Publication Data
US 2020/0209649 A1    Jul. 2, 2020

(30) Foreign Application Priority Data

Jul. 26, 2017  (EP) .................... 17183354

(51) Int. Cl.
*G02C 7/02*   (2006.01)
*A61F 2/16*   (2006.01)
(Continued)

(52) U.S. Cl.
CPC ............ *G02C 7/028* (2013.01); *A61F 2/1618* (2013.01); *A61F 2/1654* (2013.01); *G02C 7/044* (2013.01); *G02C 7/06* (2013.01); *G02C 2202/20* (2013.01)

(58) Field of Classification Search
CPC .......... G02C 7/028; G02C 7/06; G02C 7/044; A61F 2/1618; A61F 2/1654
(Continued)

(56) References Cited

U.S. PATENT DOCUMENTS 4,340,283 A * 7/1982 Cohen .................. G02B 5/1876
                                                        359/743
4,637,697 A * 1/1987 Freeman ................ G02C 7/042
                                                        359/742
(Continued)

FOREIGN PATENT DOCUMENTS

AU    2013202083 B2    4/2013
EP    2 503 962 B1     1/2011
(Continued)

OTHER PUBLICATIONS

Gori, F., et al., "Analytical derivation of the optimum triplicator," dated Dec. 1, 1998, pp. 13-16, Optics Communications, vol. 157, No. 1-6, Elsevier, Amsterdam, NL XP004150691.
(Continued)

*Primary Examiner* — James R Greece
(74) *Attorney, Agent, or Firm* — Crowell & Moring LLP

(57) ABSTRACT

An ophthalmic multifocal lens, and a method of manufacturing same, at least comprising focal points for near, intermediate and far vision. The lens comprises a light transmissive lens body providing a refractive focal point, and a periodic light transmissive diffraction grating, extending concentrically over at least part of a surface of the lens body and providing a set of diffractive focal points. The diffraction grating is designed to operate as an optical wave splitter, the refractive focal point providing the focal point for intermediate vision and the diffractive focal points providing the focal points for near and far vision. The diffraction grating has an optical transfer function comprising a continuous periodic phase profile function having an
(Continued)

argument modulated as a function of the radial distance (r) to the optical axis of the lens body, thereby tuning the light distribution in the focal points.

19 Claims, 24 Drawing Sheets

(51) Int. Cl.
*G02C 7/04* (2006.01)
*G02C 7/06* (2006.01)

(58) Field of Classification Search
USPC .................................................. 351/159.11
See application file for complete search history.

(56) References Cited

U.S. PATENT DOCUMENTS

| | | | | |
|---|---|---|---|---|
| 8,556,416 B2* | 10/2013 | Lawu | ..................... | G02C 7/06 623/6.31 |
| 9,239,471 B2* | 1/2016 | Zalevsky | .............. | A61F 2/1648 |
| 2006/0116764 A1 | 6/2006 | Simpson | | |
| 2009/0268155 A1 | 10/2009 | Weeber | | |

FOREIGN PATENT DOCUMENTS

| | | | | |
|---|---|---|---|---|
| EP | 2 375 276 A1 | 10/2011 | | |
| EP | 2 377 493 A1 | 10/2011 | | |
| EP | 2375276 A1 * | 10/2011 | ........... | G02B 5/1895 |
| IL | 105 434 A | 3/1998 | | |
| WO | WO 2006/023404 A2 | 3/2006 | | |
| WO | WO 2006/023404 A3 | 9/2006 | | |
| WO | WO 2014/064163 A1 | 5/2014 | | |
| WO | WO 2017/055503 A1 | 4/2017 | | |

OTHER PUBLICATIONS

International Search Report and Written Opinion, dated Nov. 20, 2018, pp. 1-14, issued in International Patent Application No. PCT/EP2018/069391, European Patent Office, Rijswijk, The Netherlands.

Extended European Search Report, dated Feb. 1, 2018, pp. 1-8, issued in European Patent Application No. 17183354.4, European Patent Office, Munich, Germany.

Romero, L.A., et al., "Theory of optimal beam splitting by phase gratings. II. Square and hexagonal gratings," dated Jul. 11, 2007, pp. 2296-2312, J. Opt. Soc. Am. A/vol. 24, No. 8, Optical Society of America, Washington, DC, 1084-7529/07/082296-17.

* cited by examiner

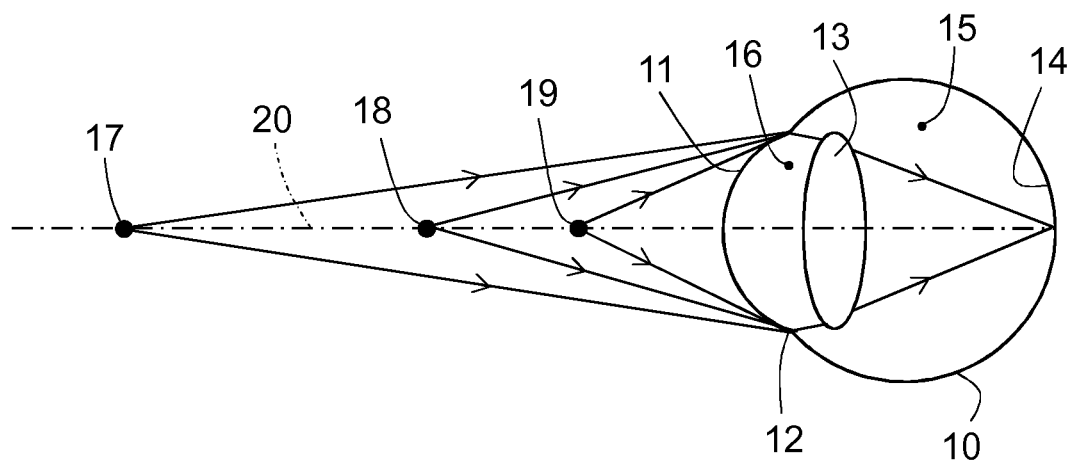
Fig. 1
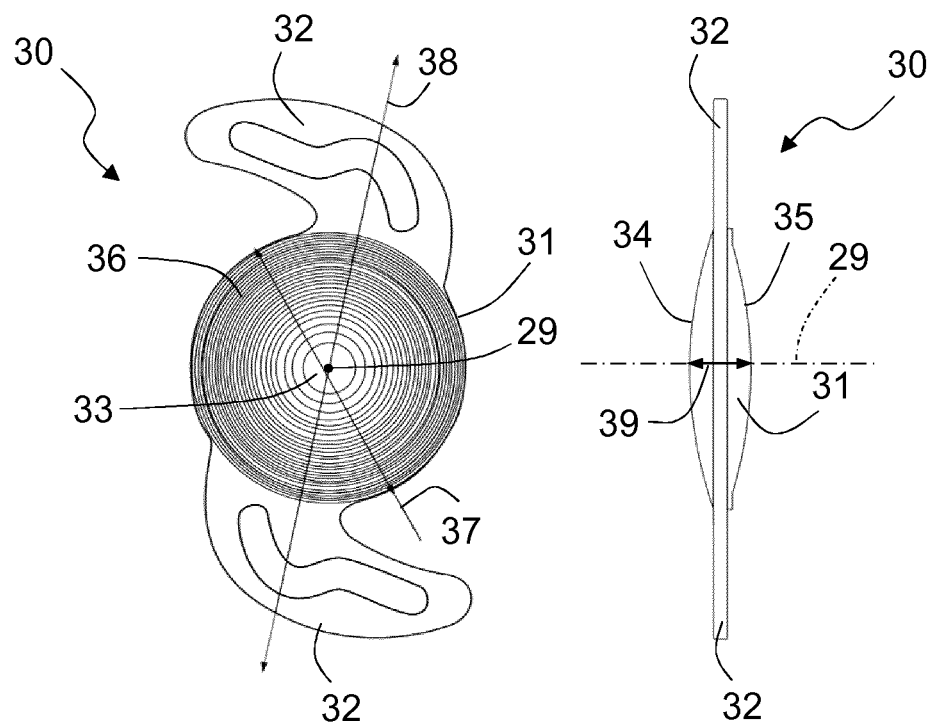
Fig. 2a
(Prior art)
Fig. 2b
(Prior art)

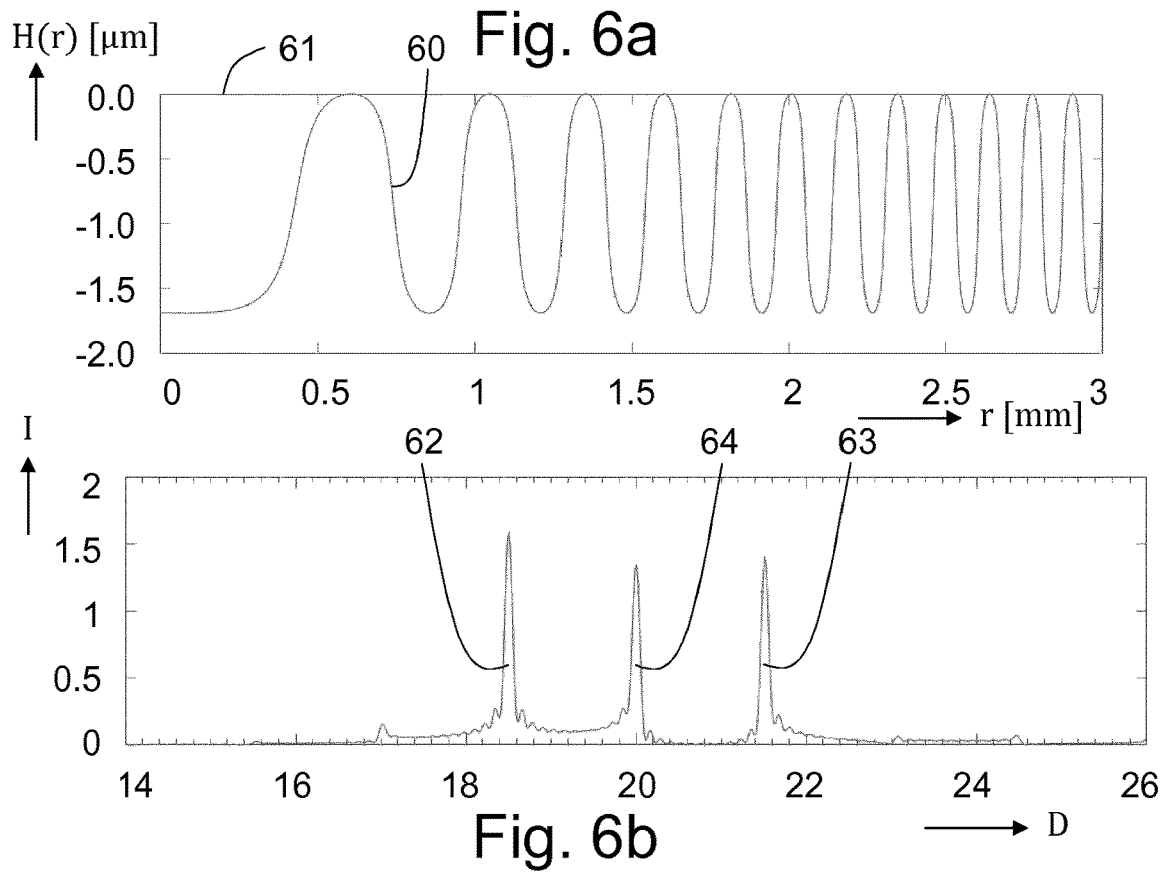
Fig. 6a
Fig. 6b
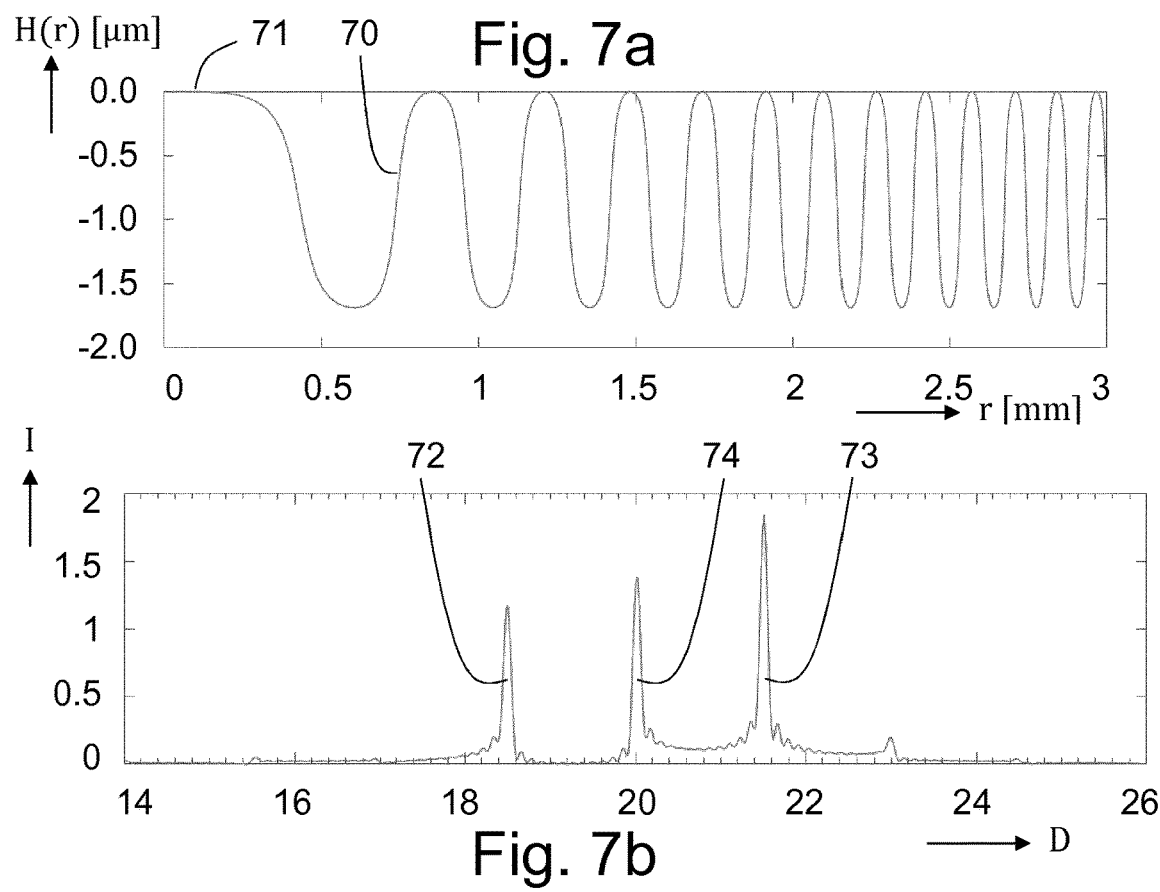
Fig. 7a
Fig. 7b

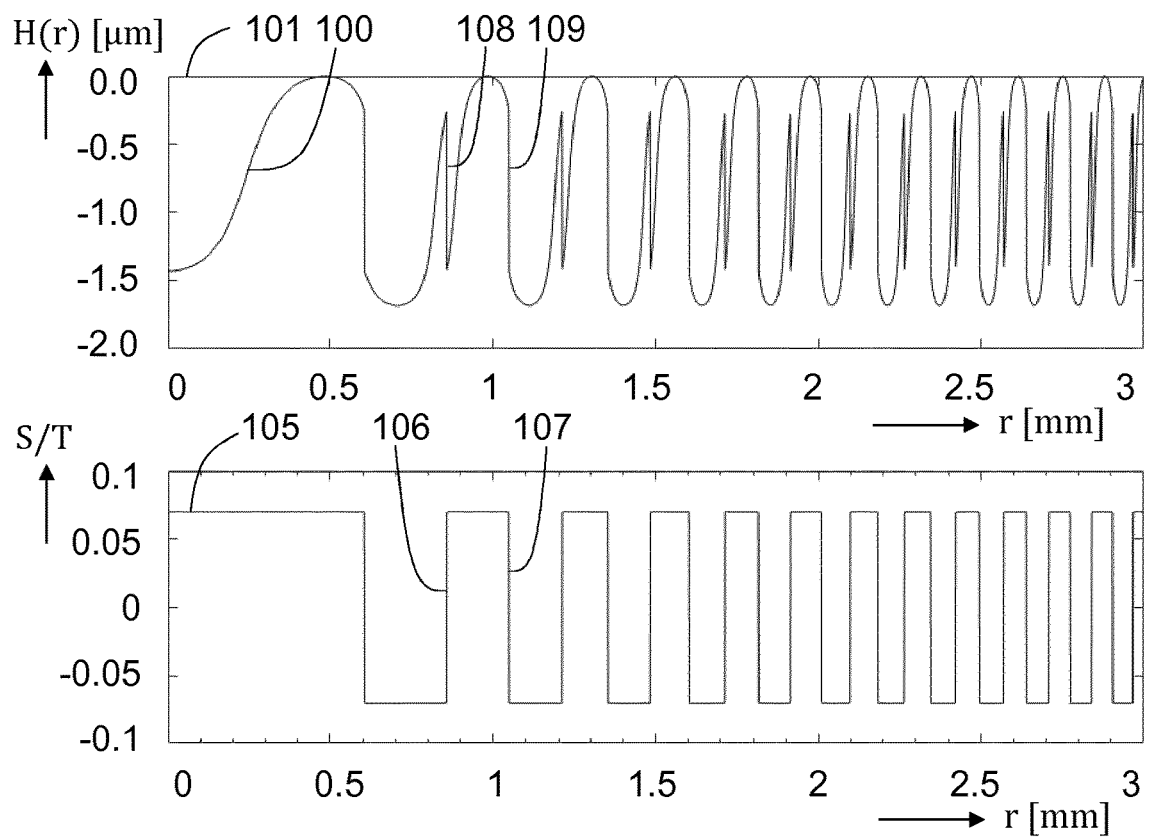
Fig. 10a
Fig. 10b
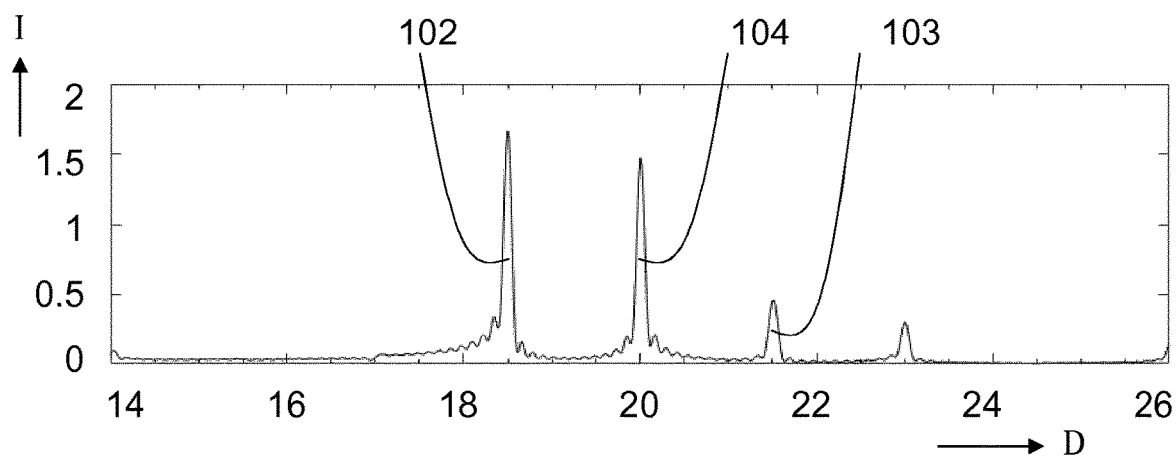
Fig. 10c

Fig. 11a
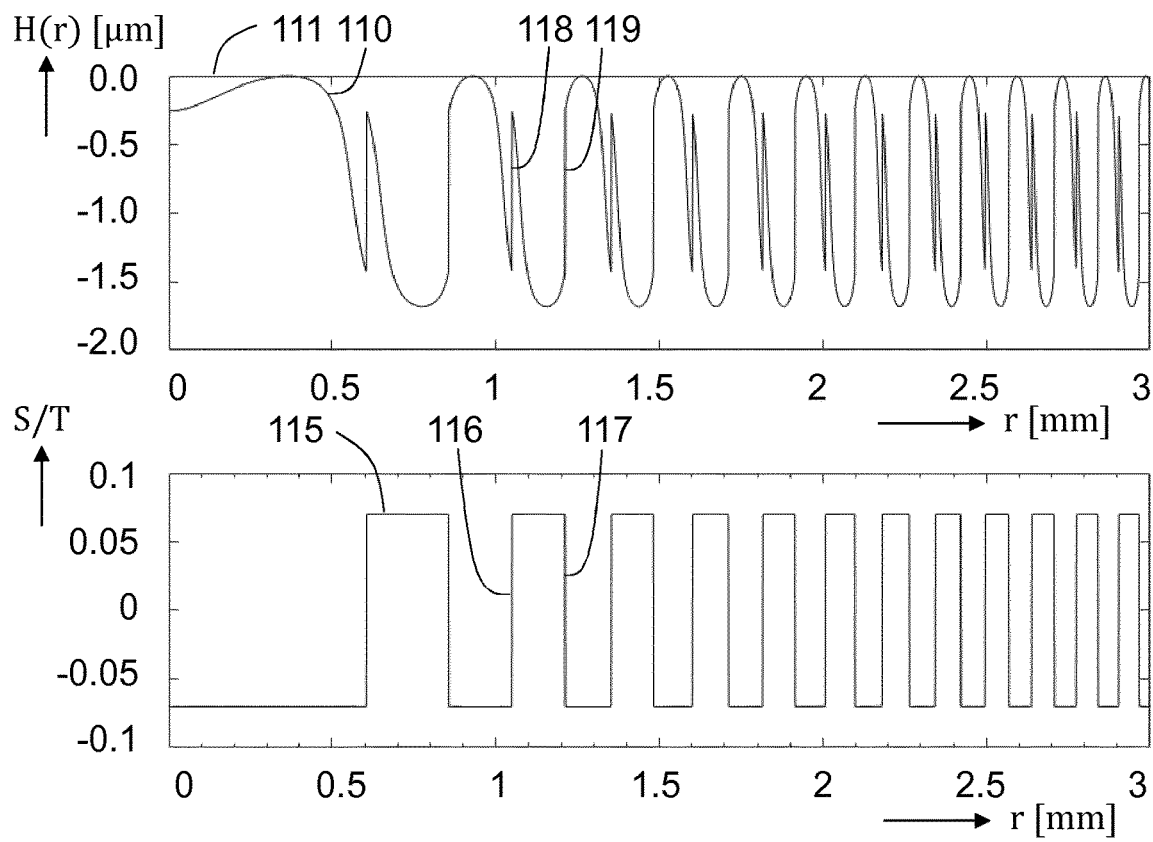
Fig. 11b
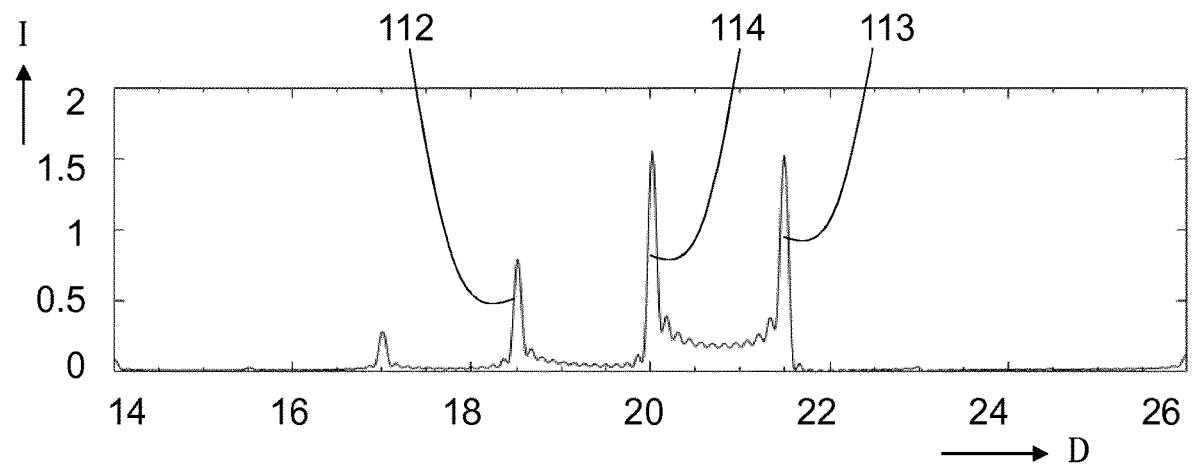
Fig. 11c

Fig. 12a
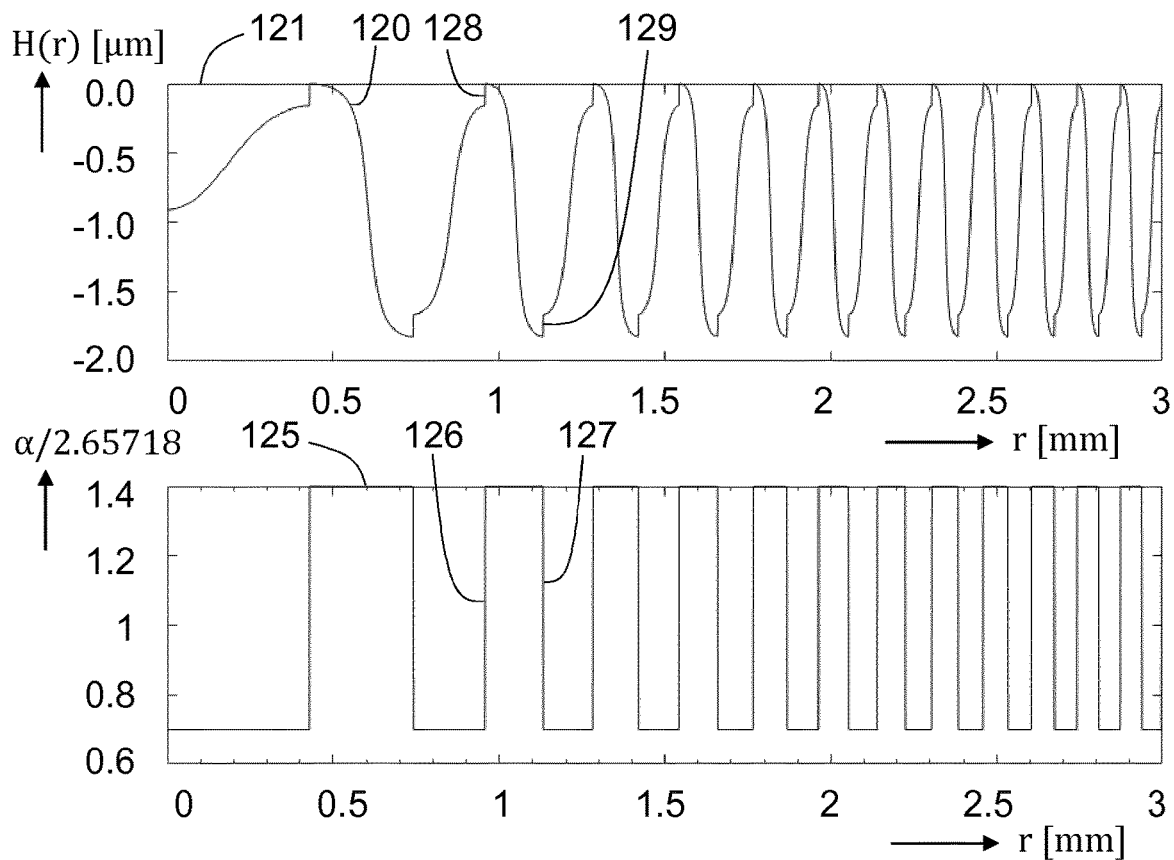
Fig. 12b
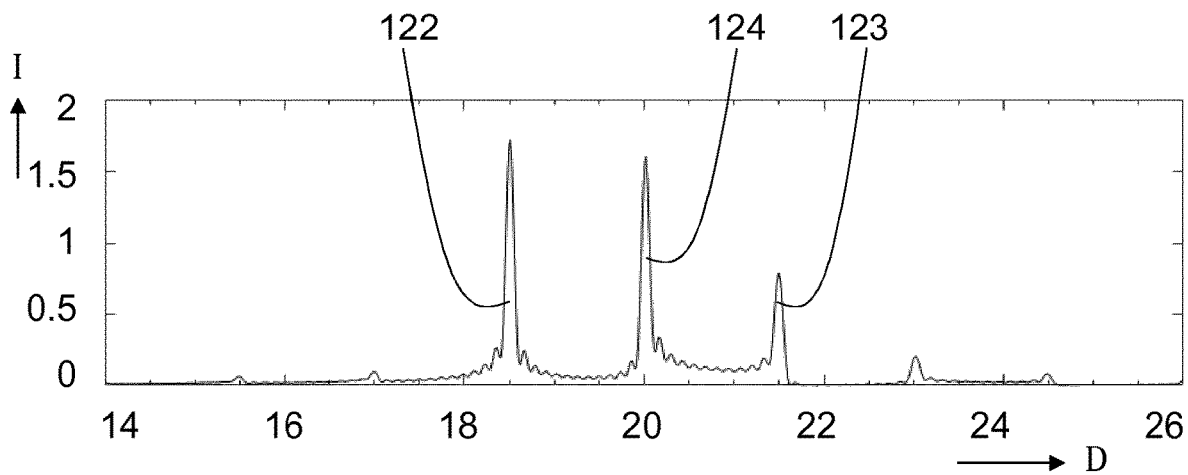
Fig. 12c

Fig. 13a
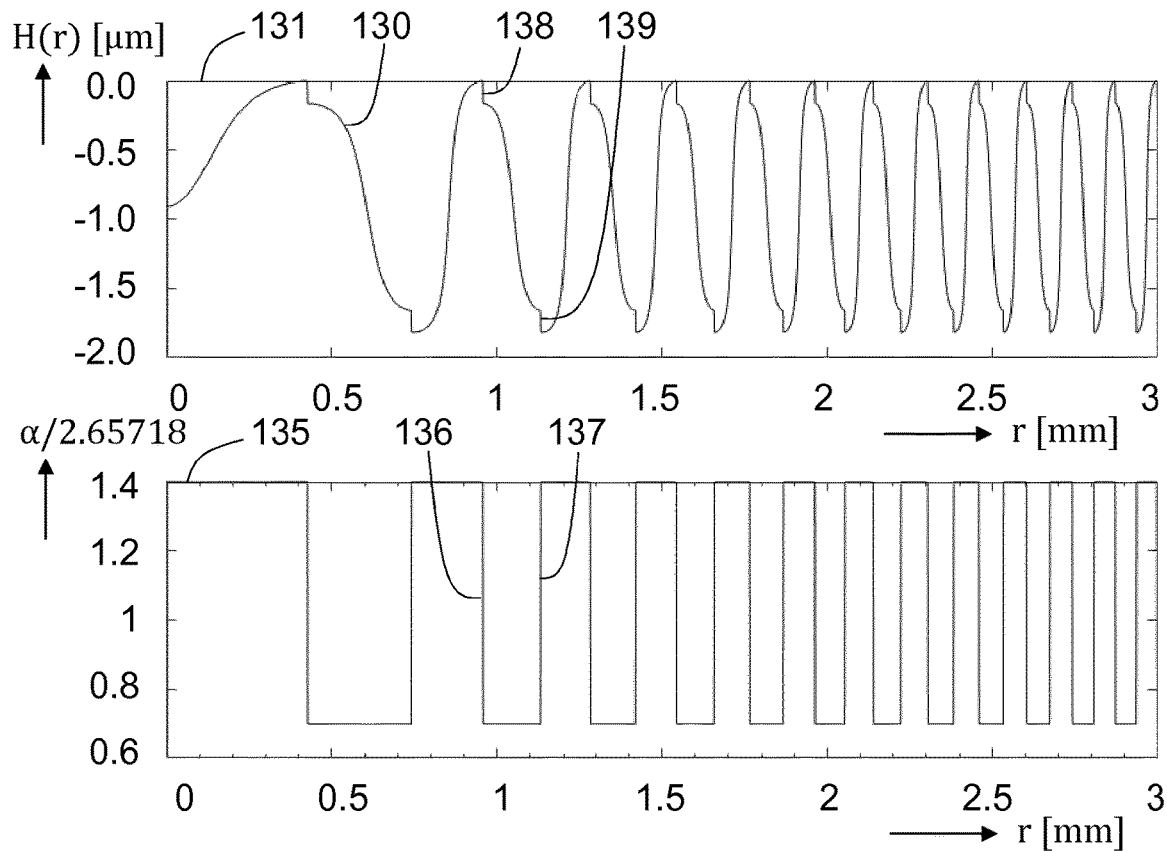
Fig. 13b
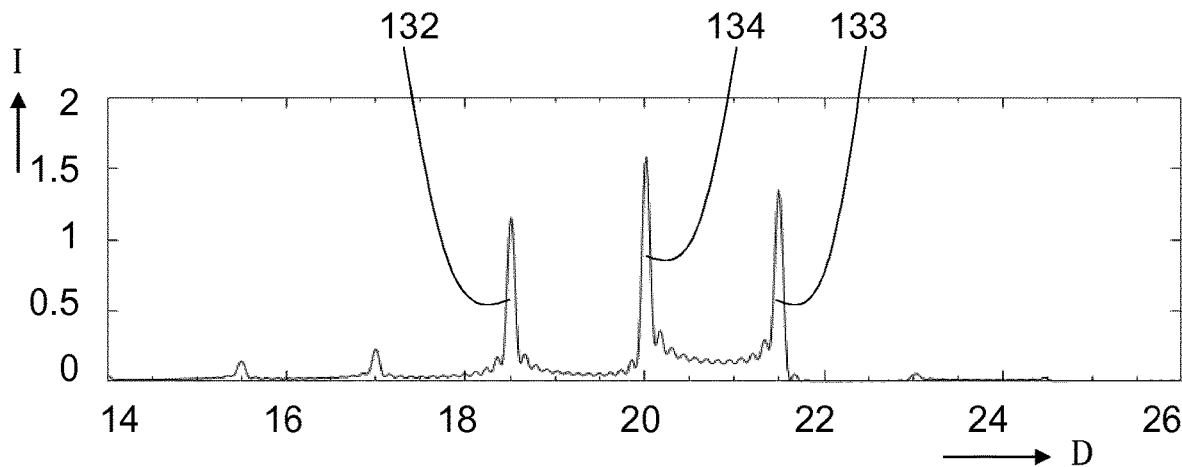
Fig. 13c

Fig. 16a
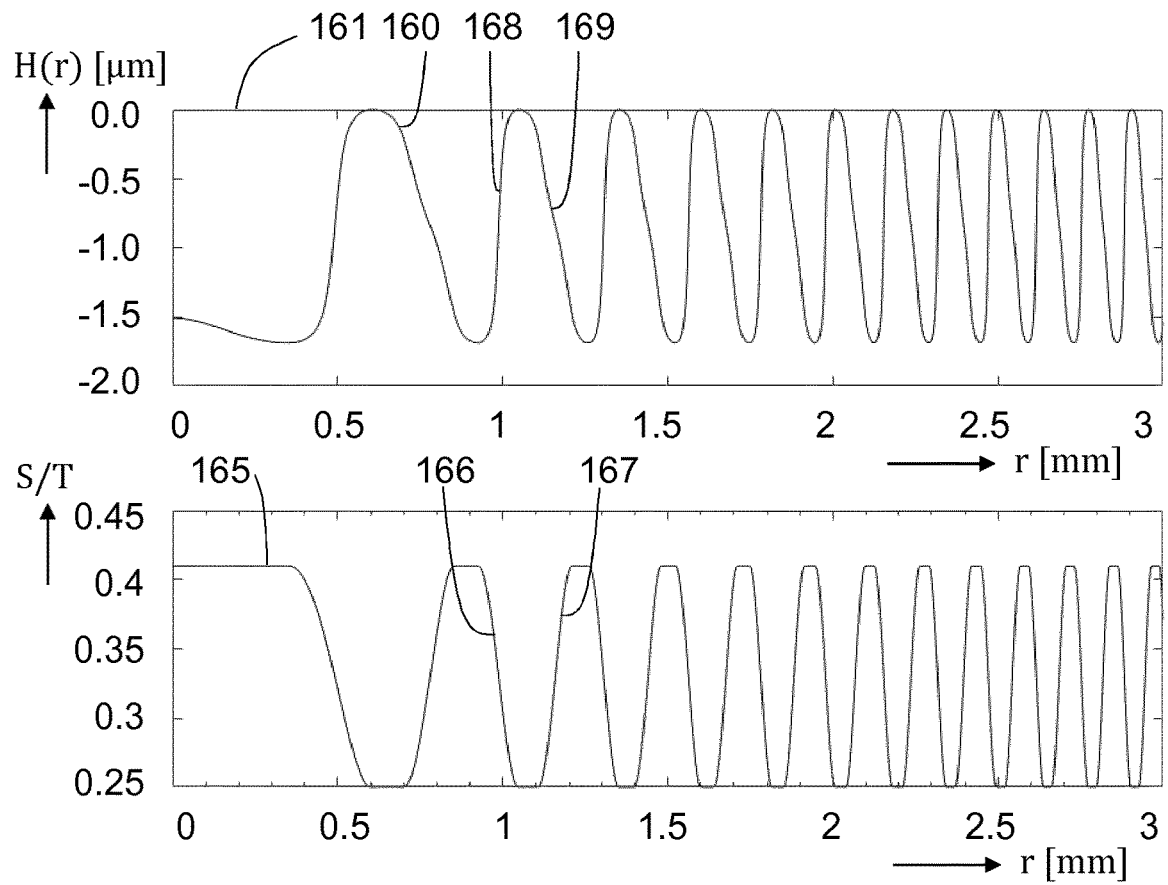
Fig. 16b
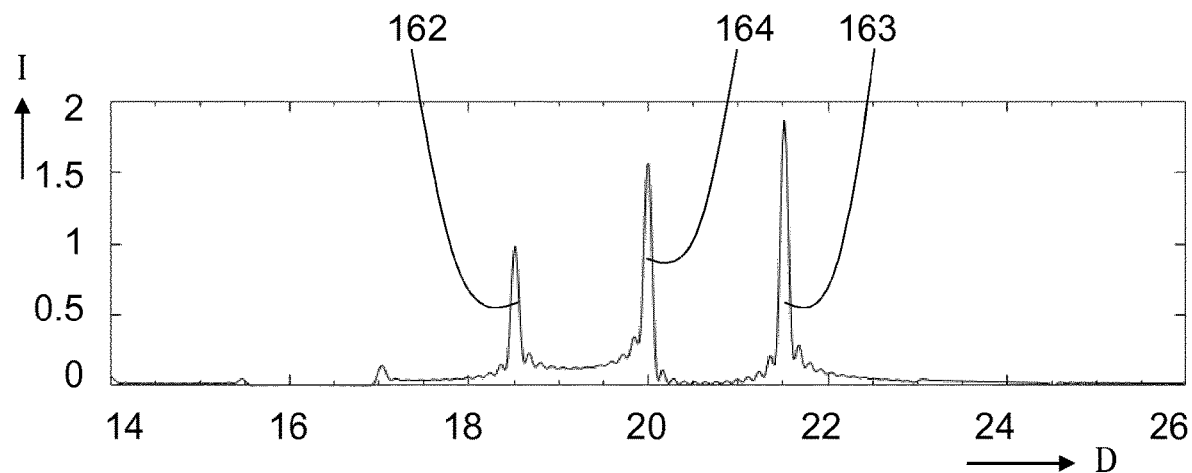
Fig. 16c

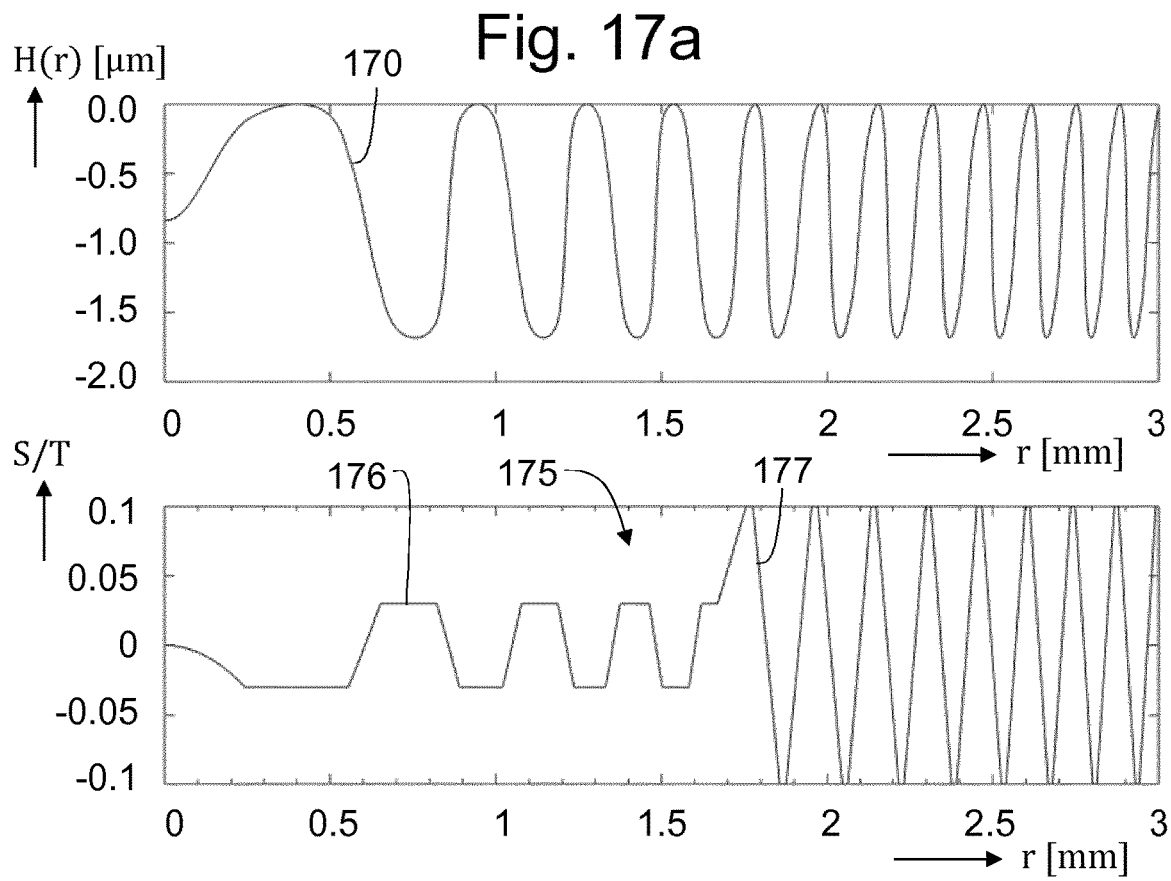
Fig. 17a
Fig. 17b
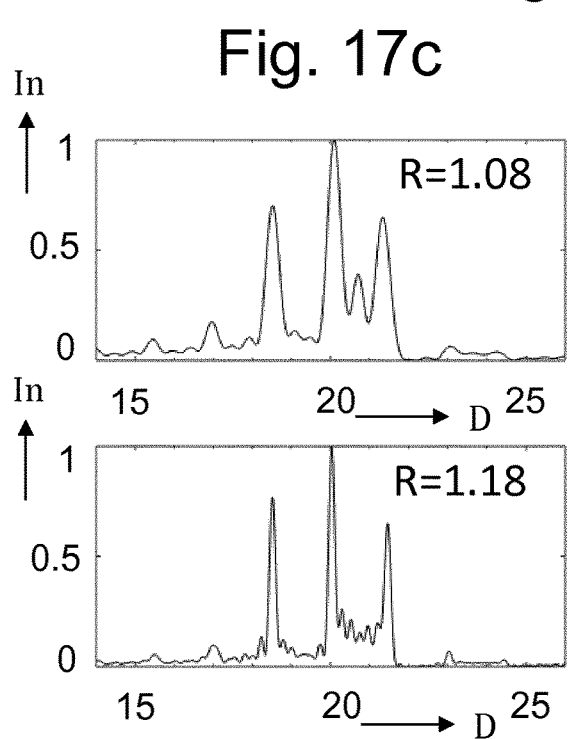
Fig. 17c
Fig. 17e
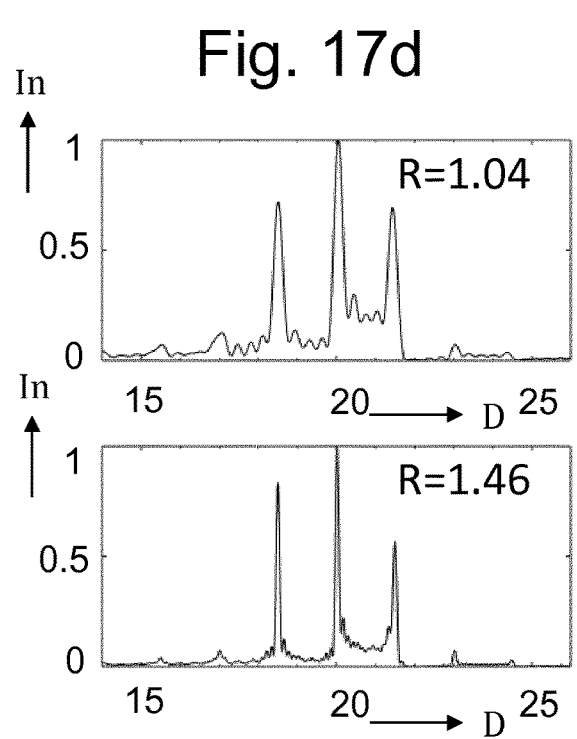
Fig. 17d
Fig. 17f

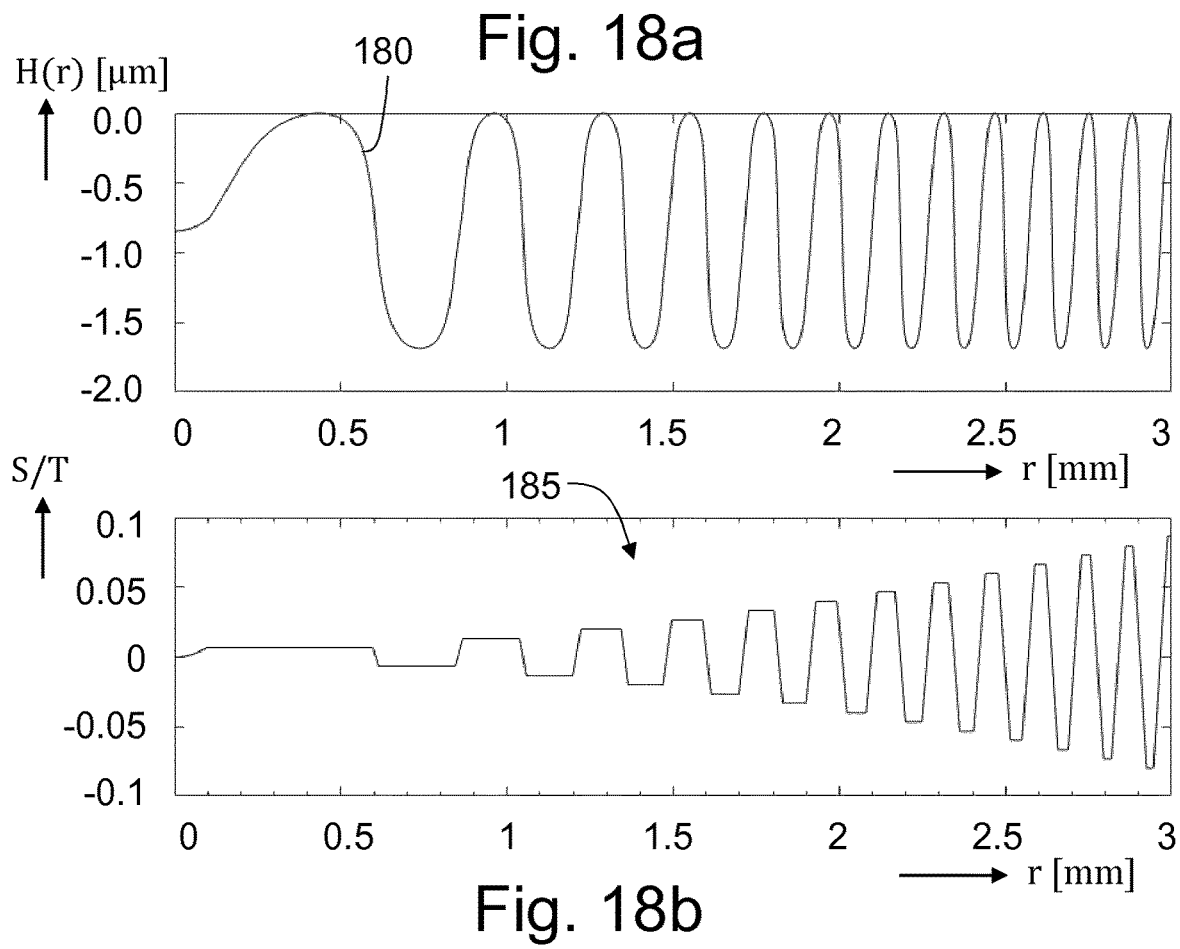
Fig. 18a
Fig. 18b
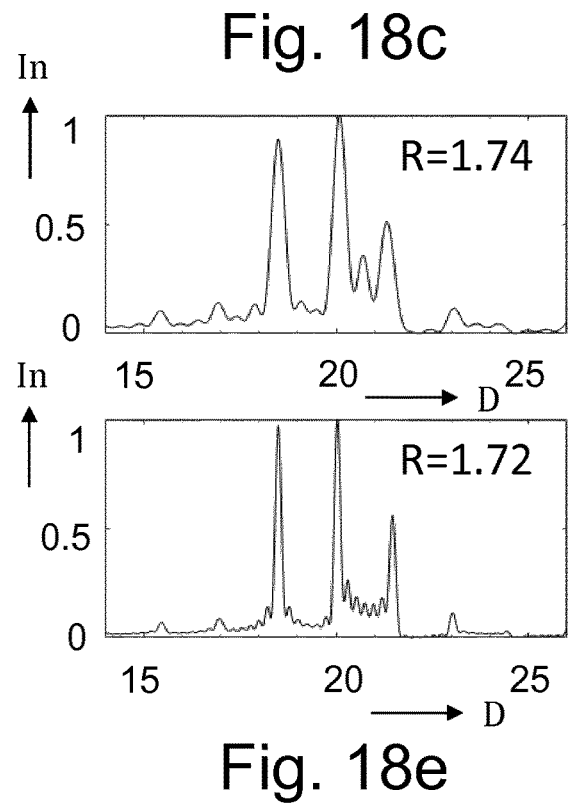
Fig. 18c
Fig. 18e
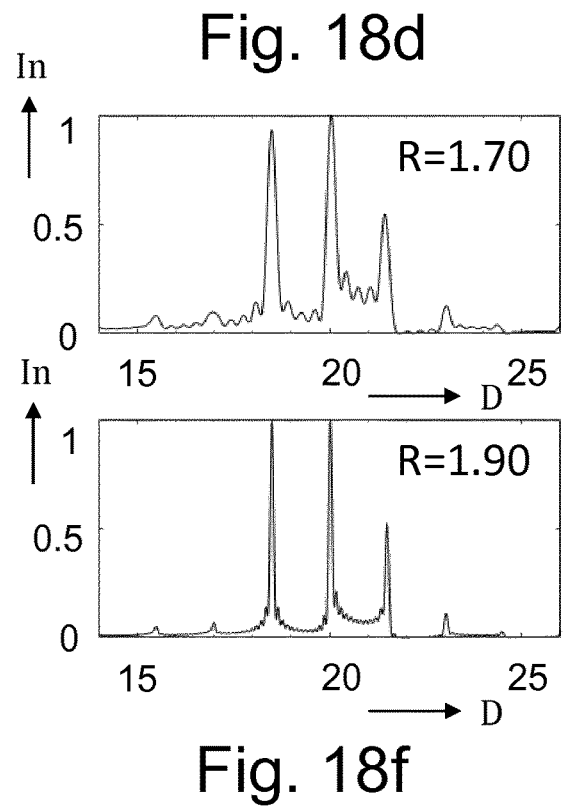
Fig. 18d
Fig. 18f

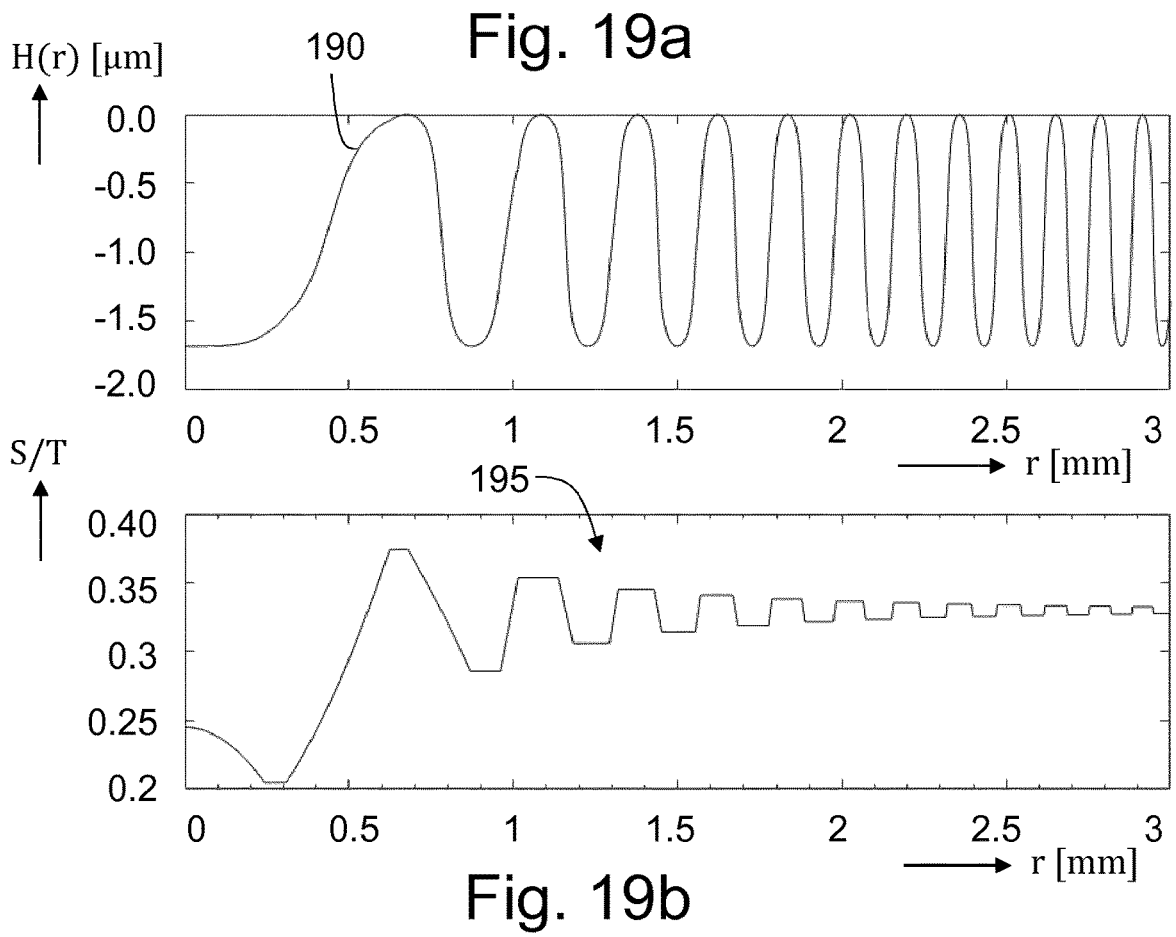
Fig. 19a
Fig. 19b
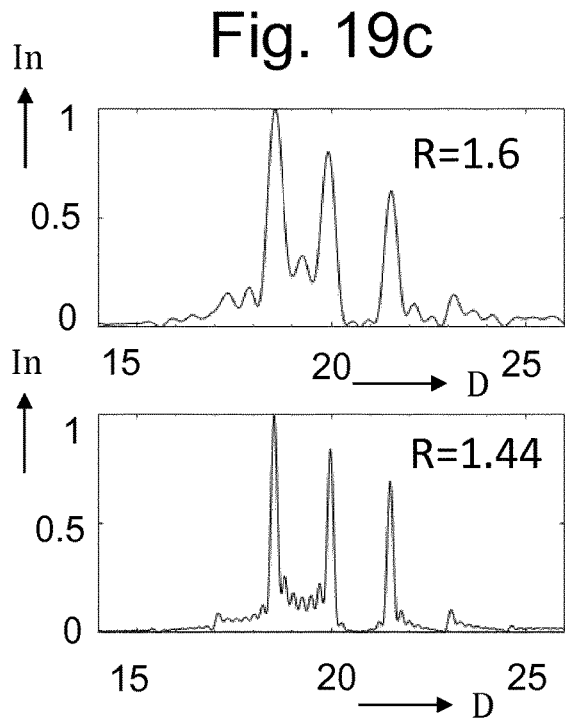
Fig. 19c
Fig. 19e
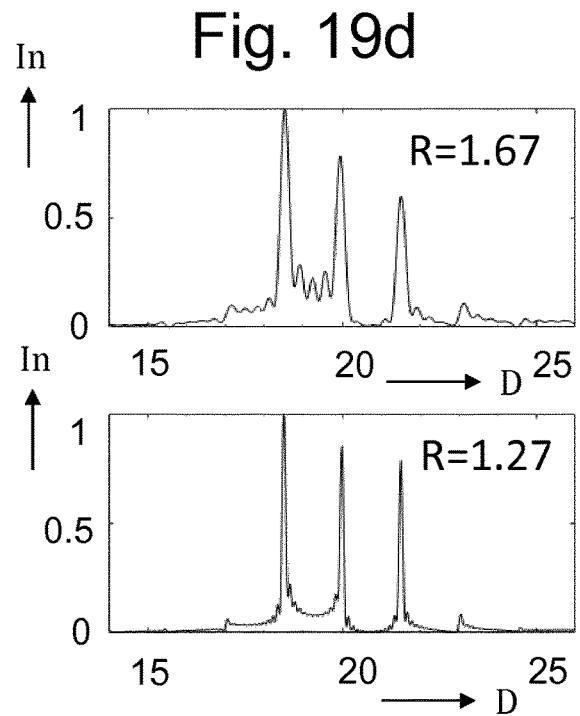
Fig. 19d
Fig. 19f

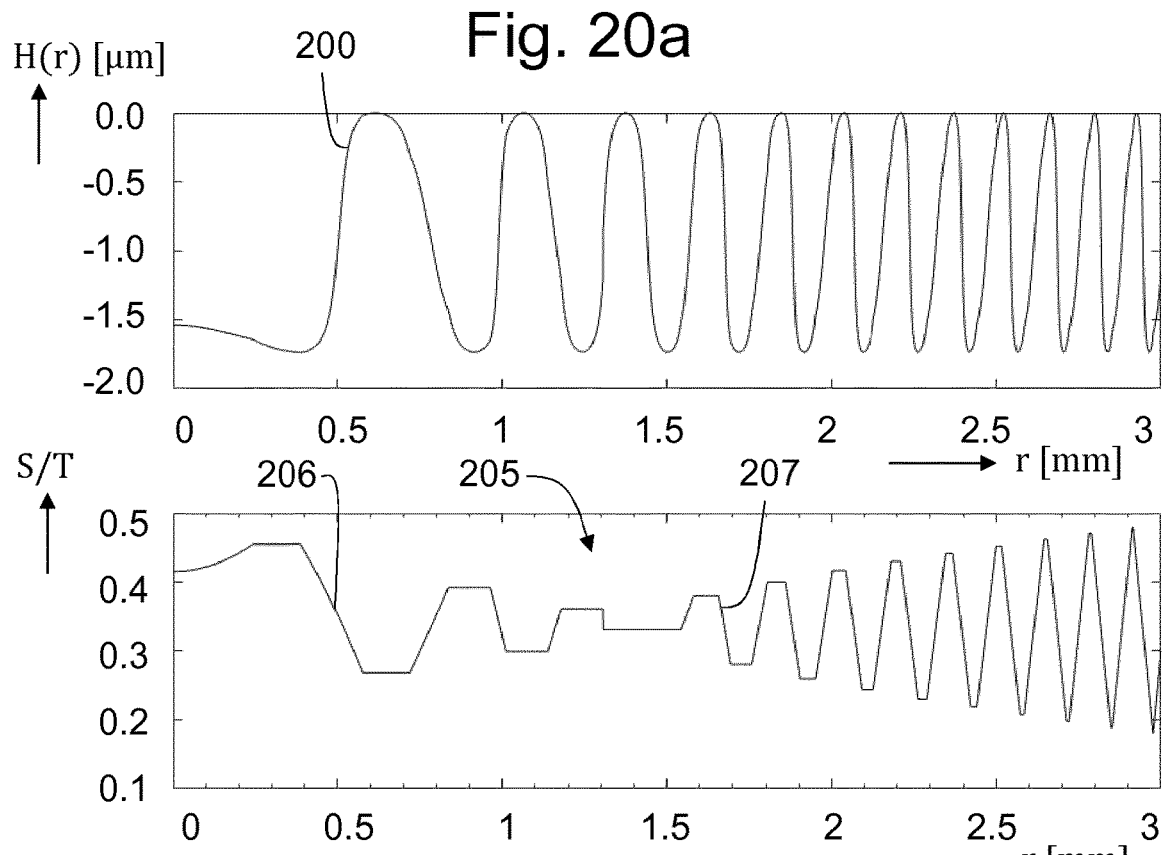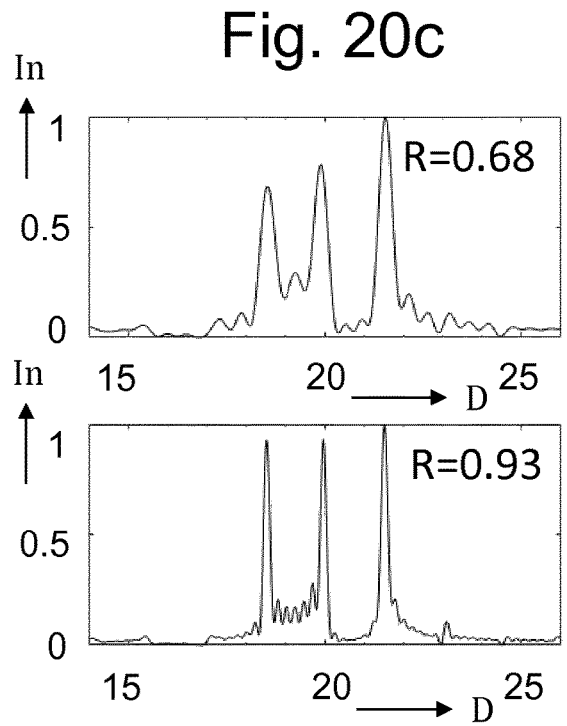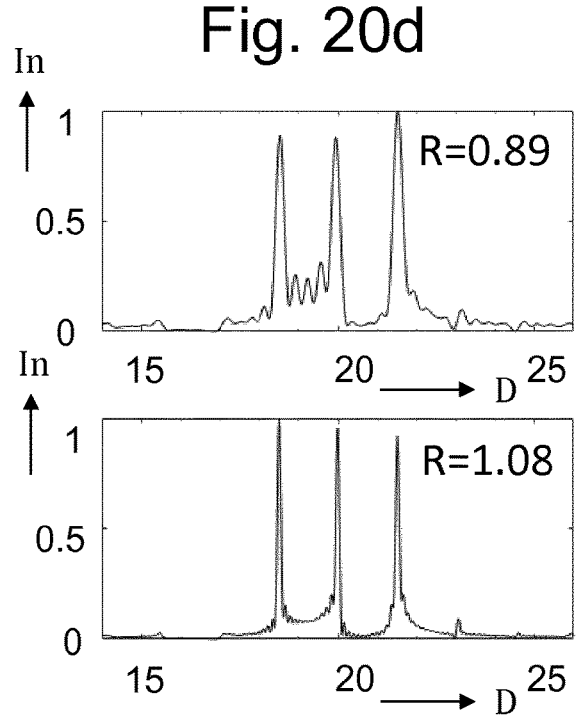

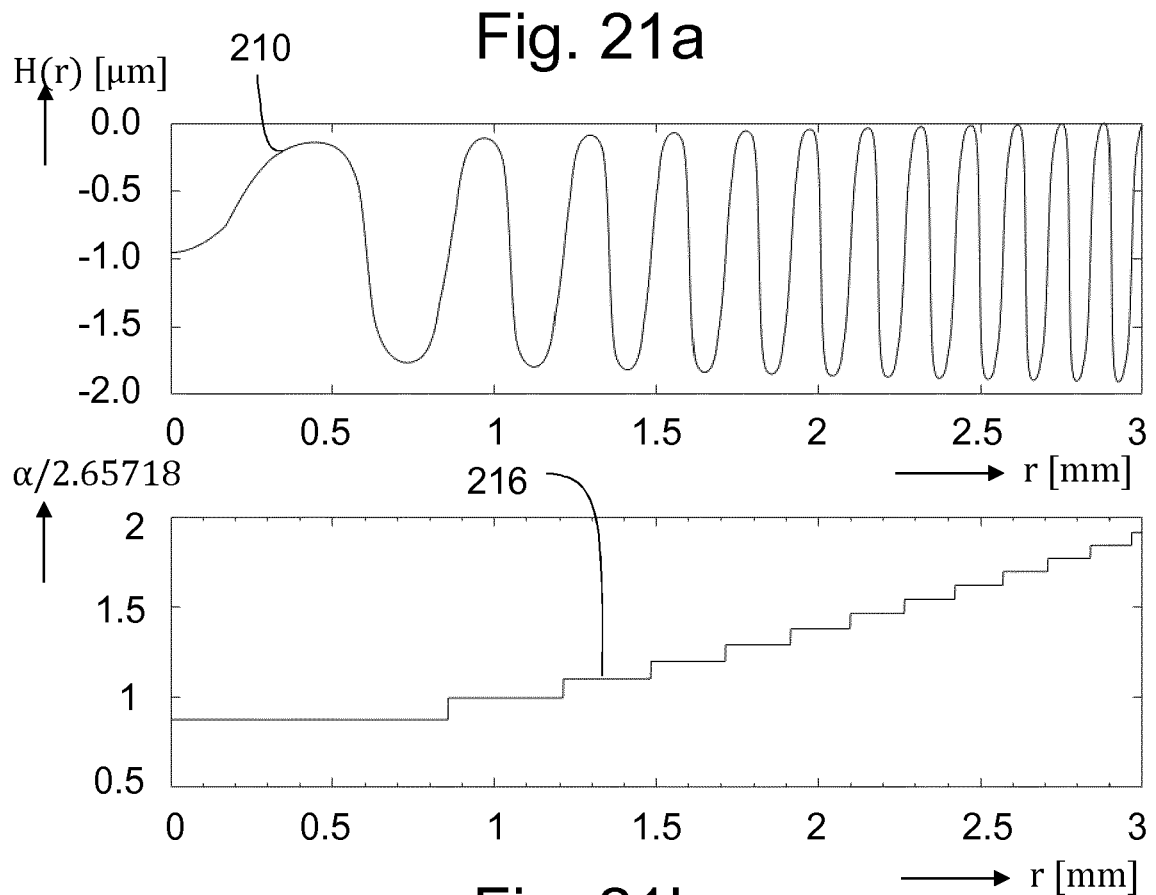
Fig. 21a
Fig. 21b
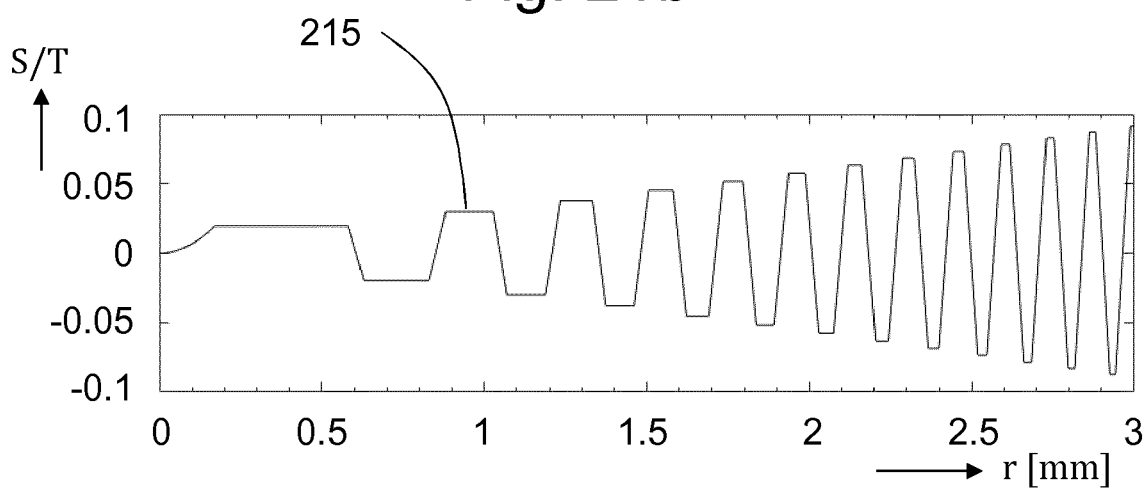
Fig. 21c

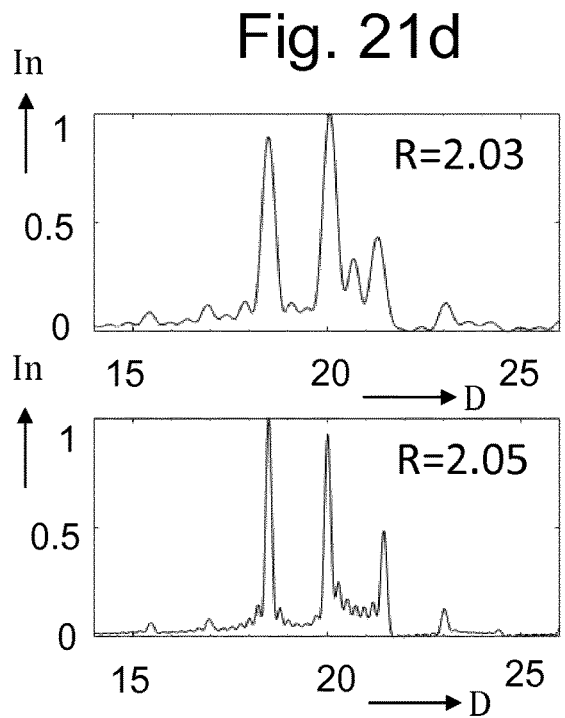
Fig. 21d
Fig. 21f
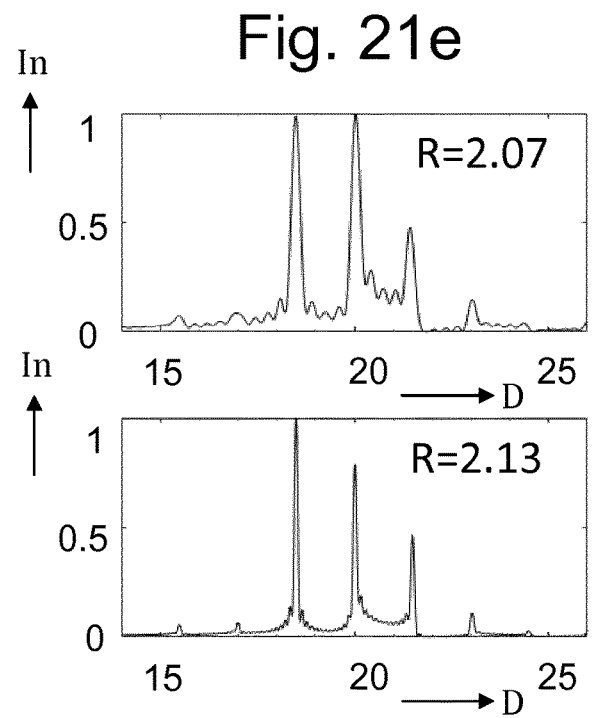
Fig. 21e
Fig. 21g
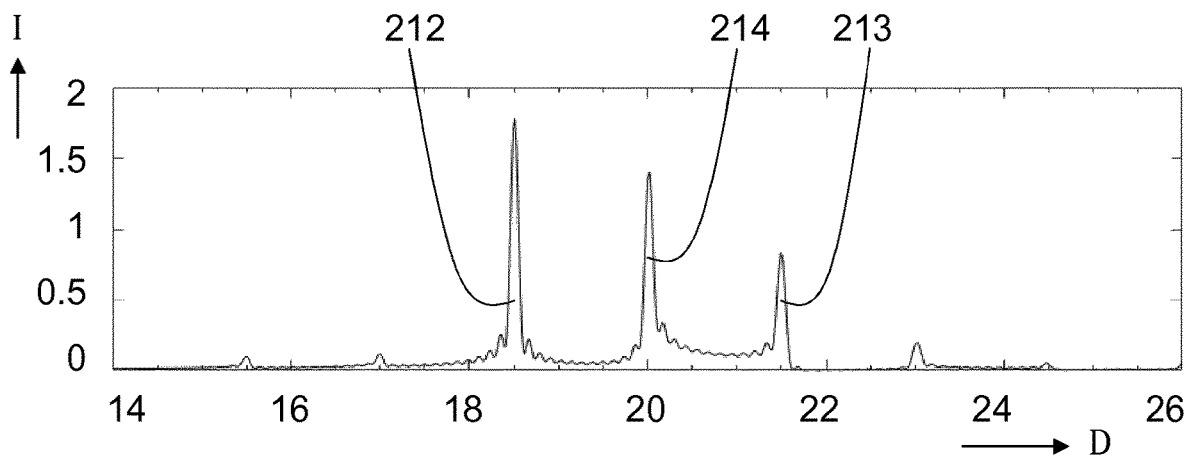
Fig. 21h

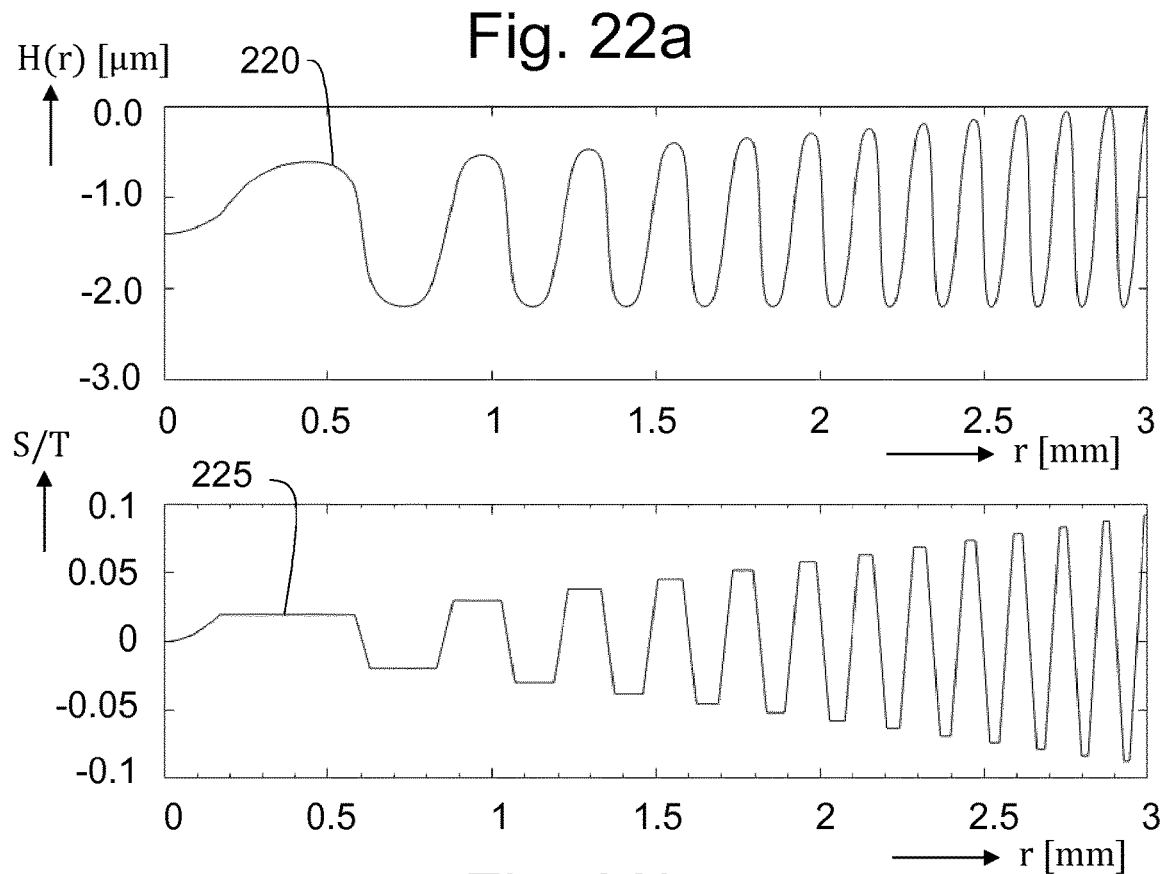
Fig. 22a
Fig. 22b
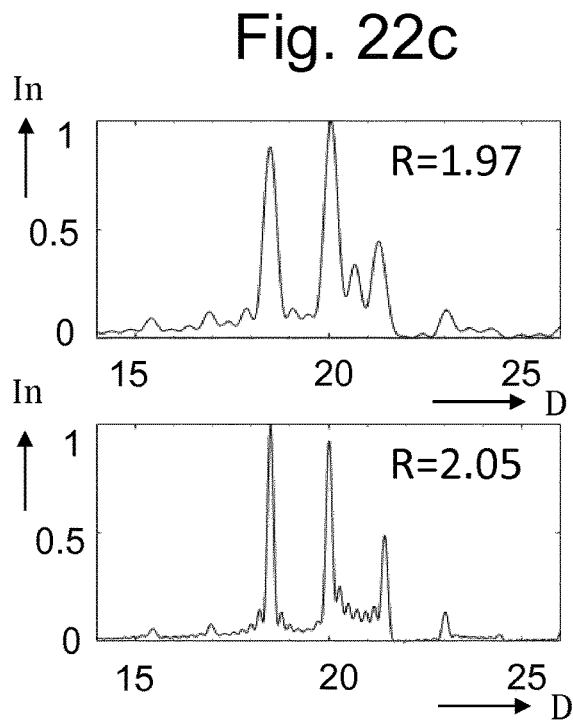
Fig. 22c
Fig. 22e
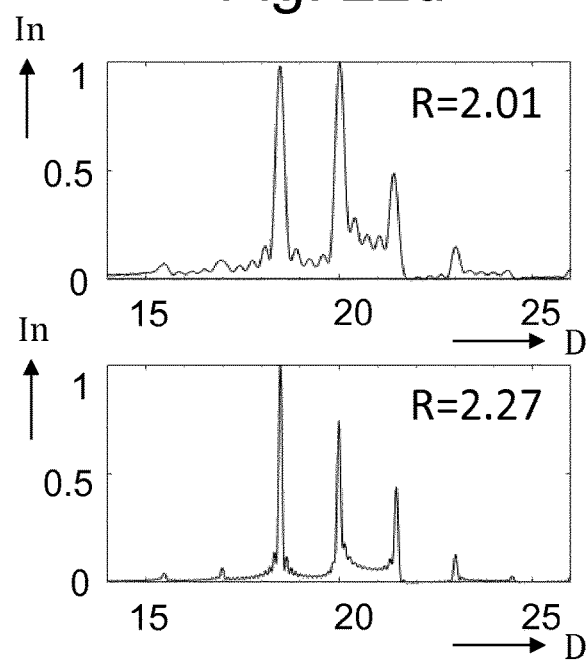
Fig. 22d
Fig. 22f

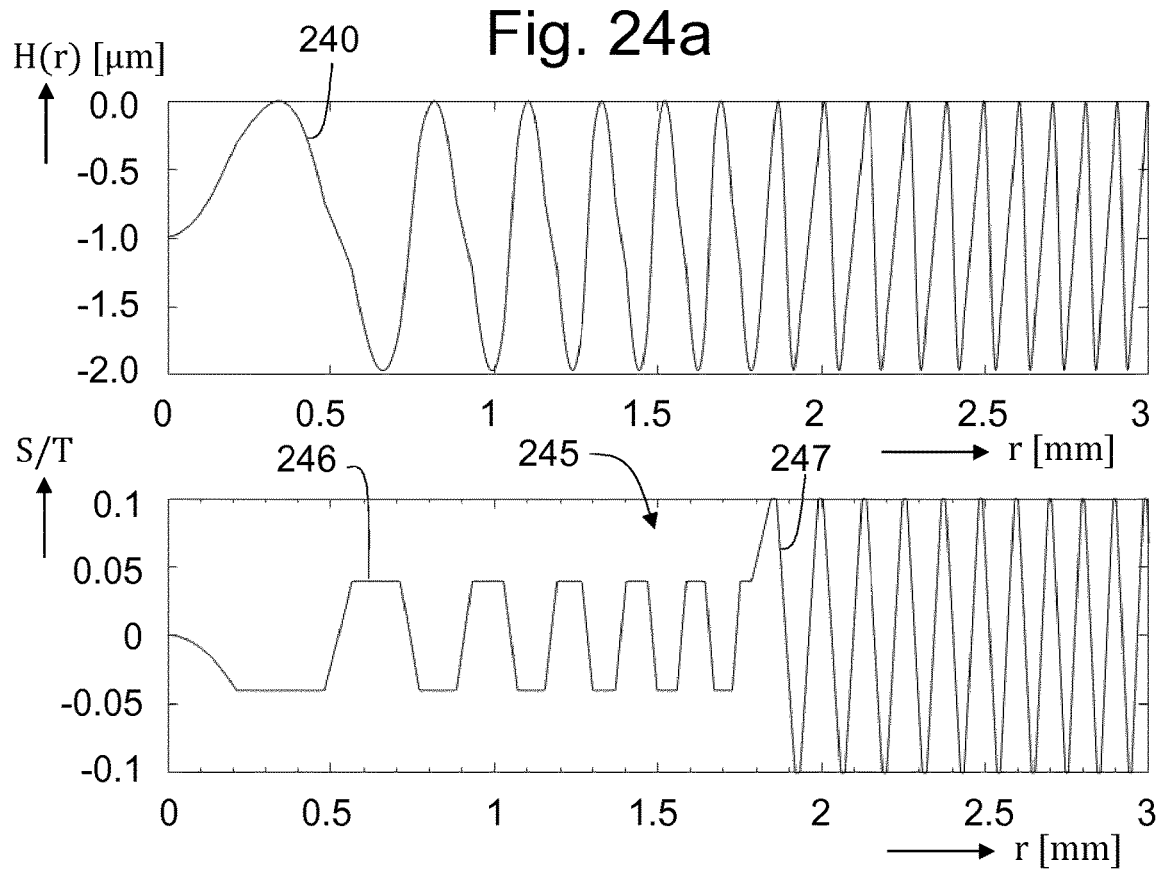
Fig. 24a
Fig. 24b
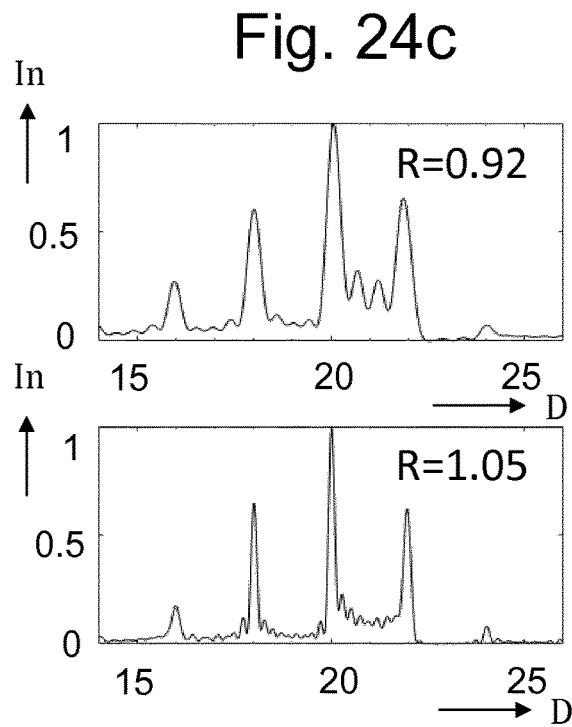
Fig. 24c
Fig. 24e
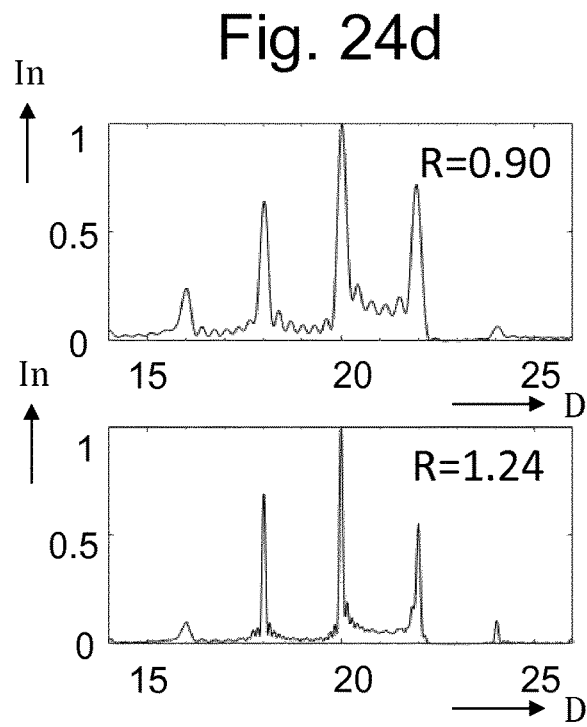
Fig. 24d
Fig. 24f

OPHTHALMIC MULTIFOCAL DIFFRACTIVE LENS

TECHNICAL FIELD

The present disclosure generally relates to ophthalmic lenses and, more specifically, to ophthalmic contact and intra-ocular multifocal diffractive lenses providing diffraction orders with tuned light distributions for different pupil sizes.

BACKGROUND

Ophthalmology is the field of medicine directed to the anatomy, physiology and diseases of the human eye.

The anatomy of the human eye is rather complex. The main structures of the eye include the cornea, a spherical clear tissue at the outer front of the eye; the iris, which is the coloured part of the eye; the pupil, an adaptable aperture in the iris that regulates the amount of light received in the eye; the crystalline lens, a small clear disk inside the eye that focuses light rays onto the retina; the retina is a layer that forms the rear or backside of the eye and transforms sensed light into electrical impulses that travel through the optic nerve to the brain. The posterior chamber, i.e. the space between the retina and the lens, is filled with aqueous humour, and the anterior chamber, i.e. the space between the lens and the cornea, is filled with vitreous humour a clear, jelly-like substance.

The natural crystalline lens has a flexible, transparent, biconvex structure, and together with the cornea, operates to refract light to be focused on the retina. The lens is more flat on its anterior side than on its posterior side and its curvature is controlled by the ciliary muscles to which the lens connects by suspensory ligaments, called zonules. By changing the curvature of the lens, the focal distance of the eye is changed so as to focus on objects at various distances. To view an object at a short distance of the eye, the ciliary muscles contract, and the lens thickens, resulting in a rounder shape and thus high refractive power. Changing focus to an object at a greater distance requires the relaxation of the lens and thus increasing the focal distance. This process of changing curvature and adapting the focal distance of the eye to form a sharp image of an object at the retina is called accommodation.

In humans, the refractive power of the crystalline lens in its natural environment is approximately 18-20 dioptres, roughly one-third of the total optical power of the eye. The cornea provides the remaining 40 dioptres of the total optical power of the eye.

With the ageing of the eye, the opaqueness of the lens diminishes, called cataract. Some diseases like diabetes, trauma, but also some medications, and excessive UV light exposure may also cause cataract. Cataract is painless and results in a cloudy, blurry vision. Treatments for cataracts include surgery, by which the cloudy lens is removed and replaced with an artificial one, generally called an intraocular lens, IOL.

Another age related effect is called presbyopia, which is manifested by difficulty in reading small print or seeing nearby pictures clearly. Presbyopia generally is believed to be caused by a thickening and loss of flexibility of the natural lens inside the eye. Age-related changes also take place in the ciliary muscles surrounding the lens. With less elasticity it becomes harder to focus at objects close to the eye.

A variety of intraocular lenses are also employed for correcting other visual disorders, such as myopia or near-sightedness, when the eye is unable to see distant objects caused by the cornea having too much curvature, for example. The effect of myopia is that distant light rays focus at a point in front of the retina, rather than directly on its surface. Hyperopia or farsightedness, caused by an abnormally flat cornea, such that light rays entering the eye focus behind the retina, not allowing to focus on objects that are close, and astigmatism, which is another common cause of visual difficulty in which images are blurred due to an irregularly-shaped cornea.

In the majority of cases, intraocular lenses are implanted in a patient's eye during cataract surgery, to compensate for the loss of optical power of the removed lens. Modern IOL optics are designed to have a multifocal optic for providing short, intermediary and distance vision of objects, also called multifocal IOL, MIOL, or more specific trifocal lenses. Presbyopia is corrected by eye glasses or contact lenses and may also opt for multifocal optics. Multifocal ophthalmic lenses make use of two optical principles, refraction and diffraction.

For illustrating the physical difference between these principles, in the present description, the wave model of light is adopted. In this model an electromagnetic wave is propagating in a particular direction with a particular speed, and having a particular wavelength, amplitude and phase.

Refraction is the deflection that a light wave undergoes when travelling from one medium, such as air or liquid, into another medium, such as glass or plastic, having different propagation velocities of the light wave.

Diffraction, in its most basic form, is based on the physical effect that light waves, when impinging on irregularities at an object, become a source of secondary light waves. These secondary waves may interfere with one another in a constructive and destructive manner. Constructive interference occurs when the optical path difference between waves arriving at a particular point is an integer multiple of their wavelength, such that their amplitudes add up in a reinforcing manner. Also called that the waves are in-phase. Destructive interference occurs when the difference in optical path length travelled by interfering light waves is an odd multiple of half of the wavelength, such that a crest of one wave meets a trough of another wave and the waves partly or completely extinguish each other. This is also called that the waves are out-of-phase.

A multifocal ophthalmic lens generally has a biconvex or plano-convex shape or a biconcave or plano-concave shape, the curvature and thickness of which is adapted to provide a first focal point at its optical axis by refraction. At one or both the anterior and the posterior surface of the lens a transmissive surface relief or diffraction grating may be provided, comprised of regularly or periodically spaced ridges and/or grooves, designed to diffract transmitted light, and arranged in concentrically rings or zones at a respective surface of the lens. The periodic spacing or pitch of the ridges and/or grooves substantially determines the points of destructive and constructive interference at the optical axis of the lens. The shape and height of the ridges and/or grooves control the amount of incident light that is provided at a point of constructive interference by diffraction. The points of constructive interference are generally called diffraction orders or focal points. The diffraction relief can be designed such as to provide a second and third focal point of a trifocal lens, different from the refractive focal point, for example.

Present multifocal ophthalmic lenses are generally designed using two well-known types of basic diffraction gratings or reliefs, that is the sawtooth type and binary type gratings or reliefs. In this description, the term sawtooth type or jagged type designates a class of transmission diffraction gratings or reliefs comprised of a plurality of repetitive, contiguously arranged, prism shaped transparent diffractive optical elements, DOEs, having a monotonic sloping light receiving surface, such as a linear or curved monotonic sloping light receiving surface. The term binary type reliefs, for the purpose of the present description, designates a class of transmission diffraction reliefs comprised of a plurality of repetitive, spaced apart rectangular or prism shaped transparent DOEs.

For operating as a lens, the repetition period or pitch of a jagged grating has to monotonically decrease in radial direction r from the center or optical axis of the lens. Or more specifically, if the first period starts in the center of the lens and the second period starts at $(1*k)^{0.5}$, where k is a constant, then the third period starts at $(2*k)^{0.5}$, the fourth at $(3*k)^{0.5}$ and so on. Accordingly, in diffractive optics it is advantageous to represent the grating in the so called $r^2$ space. That is, the parameter along the horizontal axis varies with $r^2$, such that the period occurs at equidistant repetitions.

Calculation of the focal points, i.e. the diffractive orders, of such basic reliefs is well known and straightforward for the person skilled in the art of diffractive optical lenses. In general, for use as an ophthalmic lens, the period or pitch of the basic reliefs or gratings is selected to have the first and/or second diffraction orders to provide the target focal points. This, because with these basic reliefs most of the light is diffracted in the lower diffraction orders. In the design process, the relief is constructed having an amplitude profile, such to arrive at a desired intensity profile of the light coupled in the refractive focal point and diffracted in the first and/or second diffraction orders of these basic gratings or reliefs. However, such an approach does not automatically lead to an optimal distribution of the light that incidents the lens, because an amount of light is also distributed into higher diffraction orders, that are not used, which makes tuning or controlling of the relative light distribution between the focal points of the lens difficult for different pupil sizes and that may significantly reduce the overall efficiency of the multifocal lens.

European patent 2 377 493 and European patent 2 503 962, for example, try to solve this loss of efficiency for trifocal intraocular lenses by superposing diffraction reliefs or gratings, each designed to individually provide one of the target diffractive focal points of the lens. The pitches of the reliefs or gratings have to be selected such that the second diffraction order of the one profile coincides with the first diffraction order of the other profile. Besides that the design freedom of such an intraocular lens is thereby limited to specific focal distances at which first and second diffraction orders of the different reliefs coincide, it will be appreciated that light diffracted into higher diffraction orders, not contributing to one of the target focal points, is still lost. Accordingly, these designs do not provide an effective remedy against diffraction loss in intraocular lenses.

International patent application WO2017/055503 discloses a superposition of different types of basic diffraction reliefs or gratings, such as the sawtooth type and the binary type, each having a same first order focal point. This joint focal point provides one of the target diffractive focal points of the lens. However, for the purpose of designing a multifocal lens, such as a trifocal lens, this design gets complicated as the other target focal point of the lens occurs with the summation of the superposed profiles, and hence cannot be calculated and targeted individually. beforehand.

European patent application EP 2 375 276 observes that controlling or tuning the light distribution in the focal points of diffraction reliefs or gratings comprised of sawtooth type and binary type DOEs, for example, generally designated as stepped DOEs, by varying the shape and height or amplitude of the optical transfer function of the diffraction grating, may result in diffraction gratings having sharp edges in their height profile, which are difficult to manufacture.

To this end, EP 2 375 276 discloses smoothing of the sharp edges of a stepped diffraction relief or grating, by any of curve approximation using sinusoidal and cosine functions, polynomial expressions, filtering or convolution integration using a super-Gaussian function. The smoothing has the effect that the sharp edges or steps of the sawtooth type or binary type DOEs are stretched or spread in the radial direction of the lens. EP 2 375 276 is, however, silent about providing different light distributions for different pupil sizes for a given set of target focal points.

Published US patent application 2006/0116764 discloses diffractive zones that can be disposed within a portion of a lens surface, referred to as the apodization zone, surrounded by a peripheral portion of the surface that is substantially devoid of diffractive structures. The diffractive zones can be separated from one another by a plurality of steps located at zone boundaries that have substantially uniform heights. Alternatively, the step heights can be non-uniform. For example, the step heights can progressively decrease as a function of increasing distance from the lens's optical axis. By this apodization, the light distribution in the refractive focal point relative to the diffractive focal points is tuned.

None of the above-mentioned prior art publications allow tuning of the light distribution in the target focal points individually, and differently for different pupil sizes, for example. Accordingly, there is a need for an improved ophthalmic lens design that provides freedom in targeting diffraction orders or focal points, and tuning or controlling of the relative light intensity in all the target focal points, in particular for different pupil sizes, avoiding as much as possible light diffracted in diffraction orders not contributing to target focal points, thereby providing an improved overall user experience.

SUMMARY

In a first aspect, the present disclosure provides an ophthalmic multifocal lens, at least comprising focal points for near vision, intermediate vision and far vision, having a light transmissive lens body comprising an optical axis and providing a refractive focal point, and a periodic light transmissive diffraction grating extending concentrically in radial direction across at least part of at least one surface of the lens body providing a set of diffractive focal points, wherein the diffraction grating is designed to operate as an optical wave splitter for distributing light incident at the lens body in the refractive and diffractive focal points, the refractive focal point providing the focal point for intermediate vision and the diffractive focal points providing the focal points for near vision and far vision, the diffraction grating having an optical transfer function comprising a continuous periodic phase profile function extending in radial direction of the lens body. The continuous periodic phase profile function comprises an argument modulated as a function of the radial distance to the optical axis of the lens body, thereby tuning the distribution of light incident at the lens body.

The present disclosure is based on the insight that an ophthalmic lens having a continuous periodic phase profile function extending in radial direction of the lens body causes less vision discomfort and disability above a lens having a discontinuous or jagged type phase profile function. A function is called continuous when at each point or value of its argument, i.e. the variable, term or expression on which the function operates, (i) the function is defined in such point, (ii) the limits of the function when the argument approaches that point from the right-hand and left-hand exist and are equal, and (iii) the limit of the function as the argument approaches that point is equal to the value of the function in that point.

In accordance with the present disclosure, designing the phase profile function of the optical transfer function or light transmission function of the diffraction grating as a continuous periodic phase profile function, provides freedom in the selection of target focal points as well as control of the distribution of light in the target focal points, in that the relative light distribution in the diffractive and/or refractive focal points is tuneable by modulating the argument of the phase profile function as a function of the radius or radial distance to the optical axis of the lens body.

Lenses having a continuous periodic phase profile function are, inter alia, less sensitive for diopter miscalculation. That is, a miscalculation in the required optical power correction required by a particular user, due to less accurate measurement equipment of a doctor or physician in the case of fitting an intraocular lens, or an optometrist in the case of fitting a contact lens, for example. Further, sensitivity for lens displacement (decentration) in the case of intraocular lenses, which may occur after fitting of the lens, by tilt and dislocation of the lens, is reported to be negligible for lenses having a continuous periodic phase profile function. It also has been observed that such lenses are less probable to produce glare, i.e. the difficulty of seeing in the presence of bright light such as direct or reflected sunlight or artificial light such as car headlamps at night, scattering due to non-uniformities in the path that incident light travels through the lens, and also produce less halos, i.e. white or coloured light rings or spots seen at dim light, i.e. under mesopic conditions.

Lenses having a continuous periodic phase profile function, especially in the case of being comprised of smooth curves, have the advantage of being easier to manufacture according to a calculated profile. Profiles comprising sudden displacements and sharp points will always lead to increased manufacturing errors.

The above advantages result, for the larger part, from the absence of concentric rings or zones having sharp edges in a diffraction grating having a continuous periodic phase profile function. With the present disclosure, in particular, it now becomes possible, by modulating the argument of the continuous periodic phase profile function, to effectively adapt or tune the relative light distribution or energy distribution in each of the target focal points of a periodic phase profile function. Hence, the present disclosure provides multifocal ophthalmic lenses having the advantages mentioned above and being tuneable with respect to the individual light distribution in all of its relevant or usable focal points.

In accordance with an embodiment of the present disclosure, the argument is modulated by periodic smoothened transitions in the continuous periodic phase profile function, i.e. the corresponding height profile or optical transfer function of the diffraction grating comprised by the continuous periodic phase profile function.

By introducing periodic, smoothened transitions in the continuous periodic phase profile function, i.e. the corresponding height profile, manufacturing of an optical transfer function comprising such a phase profile function does not constitute a machining problem. By smoothening of the transitions, none or negligible artefacts are introduced in the diffraction grating, such that the properties of the tuned lens comprising a continuous periodic phase profile function with respect to less unwanted optical effects like stray light, chromatic aberration, halos, glare, scattering and the like, are maintained.

In a further embodiment of the ophthalmic multifocal lens according to the present disclosure, the light distribution in each transition extends over part of a period of the continuous periodic phase profile function, thereby tuning the light distribution in the diffractive focal points, wherein each transition comprises at least one of:

a transition providing a displacement in the continuous periodic phase profile function in radial direction of the lens body, and a transition providing a displacement in the continuous periodic phase profile function in a direction transverse to the at least one surface of the lens body.

It has been found that a transition providing a local displacement in a period of the continuous periodic phase profile function in radial direction of the lens body and/or in a direction transverse to the at least one surface of the lens body, causes a change in the relative light distribution between the diffractive focal points, i.e. the focal points for near vision and far vision, compared to the continuous periodic phase profile function without such argument modulation. Whether the relative light distribution is promoted in the focal point for near vision or the focal point for far vision depends on the direction of the local displacement in a period of the continuous periodic phase profile function.

In another embodiment of the ophthalmic multifocal lens according to the present disclosure, the transitions providing a displacement in the continuous periodic phase profile function in radial direction of the lens body are arranged at a position of at least one of a leading and trailing edge or flank of the continuous periodic phase profile function, and the transitions providing a displacement in the continuous periodic phase profile function in a direction transverse to the at least one surface of the lens body are arranged at a position of at least one of a crest and a trough of the continuous periodic phase profile function.

It has been found that already small displacements in radial direction of the lens body, arranged at one or both of a leading and trailing edge, and relatively small displacements transverse to the radial direction at one or both of a crest and a trough, affect very efficiently the ratio of the light distributed between the diffractive foci.

The argument may be modulated such that transitions are provided in a plurality of periods of the continuous periodic phase profile function. That is a plurality of contiguous periods or a plurality of non-contiguous periods, dependent on the required tuning of the light distribution. Further, combinations of different modulation types are feasible. That is, combinations of transitions at leading and trailing edges or flanks of the continuous periodic phase profile function and transitions at or close to a crest or a trough of the continuous periodic phase profile function.

In accordance with a further embodiment of the present disclosure, the transitions in the continuous periodic phase profile function may comprise:

transitions providing an identical displacement in the continuous periodic phase profile function in a plurality of periods of the continuous periodic phase profile function, transitions providing a displacement in the continuous periodic phase profile function that increases over a plurality of periods of the continuous periodic phase profile function, and transitions providing a displacement in the continuous periodic phase profile function that decreases over a plurality of periods of the continuous periodic phase profile function.

The term 'identical' refers to transitions that periodically provide a substantially identical displacement in the continuous periodic phase profile function. The terms 'increase' or 'decrease' refer to transitions by which the displacement in the continuous periodic phase profile function increases or decreases, respectively, over a number of periods in radial direction of the lens body.

In the case of an identical displacement in a plurality of periods of the continuous periodic phase profile function, the light distribution in the focal points remains essentially constant over an area of the lens body, i.e. the number of periods of the continuous periodic phase profile function across which the transitions occur. By providing several, for example adjacent, areas at the lens body with mutually different displacements, different light distributions for different pupil sizes may be provided.

By varying the modulation of the argument of the continuous periodic phase profile function over the surface of the lens body, i.e. in radial direction from the optical axis, the light distribution in the focal points will vary dependent on the area of the surface of the lens body that is exposed to incident light. In this way, the relative light distribution in the focal points is made dependent from the pupil size of a user. In general, the pupil is small in size while reading a book or the like, since this is typically done in well-light environments. However, darker conditions, that bring with them a wider pupil, often occur during critical situations such as driving a car or a bike, for example. In these latter cases it is desirous to have more light in the focal point for far vision compared to the expected situations with a relatively small pupil size.

With transitions providing one of an increasing or a decreasing displacement in a plurality of periods extending over an area of the lens body, i.e. the number of periods of the continuous periodic phase profile function across which the transitions occur, the relative light distribution in the diffractive focal points will gradually change with changing pupil size.

It has been observed, for example, that by modulating the argument of, for example, three to five contiguous periods of the continuous periodic phase profile function a significant contribution is achieved in tuning the relative light distribution in the diffractive focal points, for light incident at an area of the lens across which these periods extend.

That is, for example, the argument of a first plurality of three to five contiguous periods of the continuous periodic phase profile function, starting from the optical axis of the lens body corresponding to a relatively small pupil size may be periodically modulated such that the light distributed in the near focal point is enhanced compared to the focal points for intermediate and far vision. Whereas by modulation of the argument of a further plurality of three to five contiguous periods of the continuous periodic phase profile function adjacent to or spaced over a distance in radial direction from the first plurality, the light distributed in the focal point for far vision is enhanced compared to the focal points for near and intermediate vision.

Accordingly, a spatially distributed argument modulation of a continuous periodic phase profile function, i.e. by having different modulations extending over an area or surface of the lens body, i.e. varying continuously or piecewise or discretely as a function of the radial distance to the optical axis of the lens body, provides for an effective tuning of the light distribution in the focal points for different pupil sizes.

In a further embodiment of the ophthalmic multifocal lens according to the present disclosure, the argument of the continuous periodic phase profile function is differently modulated across the lens body, thereby tuning the distributing of light incident at the lens body differently for different pupil sizes. In particular, wherein the argument is modulated in a number of contiguous periods of the continuous periodic phase profile function covering at least one area of the lens body, wherein the number of contiguous periods and modulation strength and/or modulation type of the argument differs at different areas across the lens body.

In an embodiment of the present disclosure, an ophthalmic multifocal lens is provided, wherein the argument of the continuous periodic phase profile function is modulated for providing first trifocal properties at a first area of the surface of the lens extending in radial direction and including the optical axis, which first trifocal properties emphasizing light distributed in the focal point for near vision, and providing second trifocal properties at a second area of the surface of the lens extending beyond the first area in radial direction of the lens towards a circumferential edge of the lens body, the second trifocal properties emphasizing light distributed in the focal point for far vision.

In another embodiment of the ophthalmic multifocal lens according to the present disclosure the argument is modulated providing in a same period length of the continuous periodic phase profile function a first and second transition, spaced apart in radial direction of the lens body, wherein the second transition at least partly counteracts operation of the first transition.

With substantially counteracting first and second transitions in a period length of the continuous periodic phase profile function, deviations in the period of the continuous periodic phase profile function, and thereby the position of the target focal points are effectively prevented. Further, in this way, it is possible to modify each period of the continuous periodic phase profile function independently and in a controlled manner, to get the desired local contribution to the intensity distribution. The amount of light distributed in the refractive focal point is essentially not affected by such transitions and will remain essentially the same compared to the continuous periodic phase profile function without transitions.

In a still further embodiment of the ophthalmic multifocal lens according to the present disclosure, the argument is modulated in accordance with an argument modulation function, in particular wherein the argument modulation function is a periodic function having a period equal to a period of the continuous periodic phase profile function, in particular a periodic function symmetrical about the optical axis, comprising one of a continuous function, a continuous trigonometric function, a triangle function and a trapezoid function. Such a periodic argument modulation may provide smooth transitions in the continuous periodic phase profile function as discussed above, for example.

As the diffraction grating has a periodic structure, the phase profile function of the optical transfer function is a periodic function and hence can be expanded into a Fourier series. Optimization of the overall efficiency of the light distribution in the target refractive and diffractive focal points requires that the sum of the light energies of the diffraction orders associated with the target focal points should be maximum. The light energy of each order corresponds to the square of the absolute value of the Fourier coefficient $\tau_k$ of the respective diffraction order k.

In the case of a wave splitting trifocal ophthalmic lens, for example, wherein the refractive focal point represents the focal point of intermediate vision, and the diffractive focal points represent the focal points for near and far vision, respectively, $|\tau_{-m}|^2+|\tau_0|^2+|\tau_p|^2$ should be optimized, wherein the indices −m, 0 and p represent the diffraction order providing the focal point for near vision, the refractive focal point providing intermediate vision, and the diffraction order providing the focal point for far vision, respectively.

The value of the diffraction orders −m and p need not be equal. In the present disclosure, in the case that the value of m equals the value of p, such as m=p=1, the wave splitter is called a symmetric wave splitter, whereas if the values of m and p are different, the wave splitter is called asymmetric.

The above-mentioned constraint of optimizing the overall efficiency of the light distribution in the target refractive and diffractive focal points, such that the sum of the light energies of the diffraction orders associated with the target focal points should be maximum, does not imply that the light energies in each of the target refractive and diffractive focal point should be equal. Accordingly, an optimum phase function can be derived dependent on both target focal points and target light intensities or light energies in the target focal points.

The term concentrically in respective of the repetitive DOEs of the diffraction grating, in accordance with the present disclosure, is not to be limited to concentric circular or annular zones, but includes concentric elliptic or oval shaped zones, for example, or more in general any type of concentric rotational zone shapes.

According to the publication "Analytical derivation of the optimum triplicator", by F. Gori et al., in Optics Communication 157 (1998), p. 13-16, which publication is herein incorporated by reference, for a planar symmetric wave splitter comprising two diffractive focal points at diffraction orders +1 and −1 and a refractive focal point at order 0, the phase profile function providing optimum overall efficiency, i.e. splitting an incident light beam with the highest conceivable efficiency in the focal points at the ±1 diffractive orders and the 0th order, can be expressed in a single continuous closed-form expression or function.

In an embodiment of the multifocal ophthalmic lens according to the present disclosure, the diffraction grating is arranged for operating as a wave splitter and comprises two diffractive focal points at diffraction orders +1 and −1, and wherein the continuous periodic phase profile function is expressed by a single continuous closed-form expression or function in accordance with:

$$\phi(r) = A(r) * F\left[\alpha(r) * G\left(\frac{2\pi\{r^2 - S(r)\}}{T}\right)\right] + B(r) \quad (1)$$

wherein:

$\phi(r)$ is the continuous periodic phase profile function of the diffraction grating, r is the radial distance or radius outwardly from the optical axis of the lens body, [mm], A(r) is an amplitude modulation function of the continuous periodic phase profile function in radial direction of the lens body, $F[\alpha*G]$ is a function in radial direction of the lens body providing the wave splitter operation, G(r) is a continuous periodic function in $r^2$ space, $\alpha(r)$ is an argument magnitude modulation function of G, S(r) is an argument angle modulation function of G in $r^2$ space, [mm$^2$], T is a period or pitch of the diffraction grating in $r^2$ space, [mm$^2$], and B(r) is an amplitude modulation function of the continuous periodic phase profile function, wherein at least one of the argument magnitude modulation function $\alpha(r)$ and the argument angle modulation function S(r) comprises the argument modulated as a function of the radial distance to the optical axis of the lens body.

Both $\alpha(r)$ and S(r) may be independently selected for modulating the argument of the continuous periodic phase profile function for tuning the light distribution in the target focal points, for different pupil sizes.

In accordance with the present disclosure, the light distribution in the diffractive and refractive focal points may be further tuned by an adaptation of at least one of the amplitude modulation function A(r) and the amplitude modulation function B(r) of the continuous periodic phase profile function.

The amplitude modulation functions A(r) and B(r) provide a further control of the amount of light that is distributed between the ±1 diffraction orders and the 0th order dependent on the pupil size. In general, provided that the largest phase retardation in the phase profile is below the design wavelength, an increase of any or both of the amplitude modulation functions will increase the amount light diffracted in the ±1 diffraction orders, i.e. the diffractive focal points, compared to the 0th order or refractive focal point, while a decrease of any or both of the amplitude modulation functions will increase the amount of light provided in the refractive focal point compared to the diffractive focal points.

The amplitude modulation functions may vary as a function of the radial distance from the center or optical axis of the lens, for apodizing purposes. Changing the amplitude is a manner to control the relative light intensity in the intermediate, i.e. the refractive, focal point. In practical embodiments, according to the present disclosure, the amplitude modulation functions A(r) and B(r) may be constant over part of the lens body.

It can be proven that the phase profile function $\phi(r)$ in equation (1) wherein $F[\alpha*G]$ is an inverse tangent function and G (r) is a sine function, with S(r)=0, A(r)=1 and B(r)=0, represents a continuous periodic phase profile function of a planar diffraction grating splitting an incident light beam with the highest conceivable efficiency in the focal points at the ±1 diffractive orders and the 0th order, as disclosed by Gori et al.

The argument magnitude modulation function or light distribution parameter $\alpha(r)$ according to Gori et al. determines the amount of light that is distributed among the ±1 diffractive orders and the 0th order. The overall efficiency of such a phase profile function $\phi(r)$ for planar diffraction gratings is above 0.925. In the case of a constant value of $\alpha(r)=2.65718$ light energy in the planar diffraction grating is evenly distributed among the target focal points.

Hence, a periodic continuous phase profile function, in addition to the above-mentioned advantages, provides for optimization of the overall efficiency of the light distribution in the target refractive and diffractive focal points, avoiding as much as possible light diffracted in diffraction orders not contributing to target focal points, thereby providing an improved overall user experience.

As the optimum triplicator by Gori et al. is calculated for a linear or planar phase grating, transforming same into a lens, such that the distances between the periods of the phase profile function having a square root dependency, equal distribution of light in the focal points, for example, is achieved with the present disclosure by modulation of the argument of the continuous periodic phase profile function. A nearly even light distribution in the focal points over an area of the lens body, for example, is provided when the value of the argument angle modulation S(r)=0.33, the value of the argument magnitude modulation function or light distribution parameter α(r) over part of the lens body equals the value of 2.65718 and the amplitude modulation functions have constant values of A(r)=0.96 and B(r)=0. Those skilled in the art will appreciate that other values of the modulation functions or modulation parameters mentioned above may result in a nearly even light distribution in the focal points of the lens.

In general, for tuning the light distribution, the argument angle modulation function S(r) may have a constant value over part of or over the complete lens body. In practice, values of S(r) may range between −0.5*T and 0.5*T in $r^2$ space. In particular S(r) may have a constant value ranging between 0.35*T and 0.5*T and/or between −0.05*T and −0.15*T, in particular S(r)=0.42*T in $r^2$ space. The region ranging between 0.35 T and 0.50 T offers a good intensity distribution for the three foci with the possibility to tune according to how much far vision dominance is desired. A value of S(r)=0.42*T provides a good balance of the foci for an ophthalmic lens. The region ranging between −0.05 T and −0.15 T renders a relatively even light distribution. This region is furthermore very suitable for argument modulations that (locally or over the whole lens) promote the far focus point since the disturbances created by such modulation are negligible. In some regions there can be a small increases of higher orders when argument modulation is implemented.

A constant value of the argument angle modulation function S(r) represents a phase shift of the continuous periodic phase profile function and determines the start of the slope of the phase profile function and thereby whether more light is diffracted in the +1 diffraction order or whether more light is diffracted in the −1 diffraction order, dependent on the sign and value of the phase shift, respectively. It is advantageous to express this phase shift S as a fraction of the period T of the grating, such as S=±0.25*T. Those skilled in the art will appreciate that a particular phase shift including integer values of the period T of the diffraction grating will take the same effect as a corresponding phase shift within a single period T.

By a proper selection of the argument magnitude modulation function or light distribution parameter α(r) the amount of light that is distributed in the 0th order, i.e. the focal point of intermediate vision in the present disclosure, can be tuned. In accordance with the present disclosure, α(r) may have a constant value across part of or across the complete lens body. In practice, values of α(r) may range between 2 and 3, for example.

In practical embodiments, according to the present disclosure, the amplitude modulation functions A(r) and B(r) may also have a constant value across part of or across the complete lens body, i.e. providing aggregated amplitude modulation parameters that may range between 1.4 and 0.6, for example.

By setting any or all of the modulation variables α(r), S(r), A(r) and B(r) at respective values over part of the lens body in radial direction thereof, the light intensity profile of a trifocal intraocular lens, for example, can be effectively tuned for different pupil sizes.

The surface of the lens body can also be modified by applying Fourier filtering or convolution with a kernel, or other known signal processing methods may be applied to smoothen or slightly reshape the lens profile to change the energy distribution between the diffraction orders or to remove unwanted stray light. Such modifications are often easier to apply in $r^2$ space.

In an embodiment of the ophthalmic multifocal lens according to the present disclosure, based on the phase profile function φ(r) disclosed in equation (1) above, the height profile H(r) of the diffraction grating of the lens may be expressed in a single continuous closed-form function defined by:

$$H(r) = A(r) * \frac{\lambda}{n - n_m} * \frac{\phi(r)}{2\pi} + B'(r) \qquad (2)$$

wherein: H(r) height profile of the diffraction grating of the lens, [nm],
λ is the design wavelength of the lens, [nm],
n is the index of refraction of the lens body,
$n_m$ is the index of refraction of the medium surrounding the lens body, and $$B'(r) = \frac{\lambda}{2\pi(n - n_m)} B(r), \text{ [nm]}.$$

For the phase profile function φ(r) in equation (1) wherein F[α*G] is an inverse tangent function and G (r) is a sine function, A(r)=1 and B(r)=0, for example, the height profile H(r) of the diffraction grating of the lens disclosed in equation (2) above is a closed-form continuous geometric function based on sine and cosine functions and, accordingly, has no sharp transitions which are difficult to manufacture in the lens body. Accordingly, the height profile or height function H(r) not only provides optimum efficiency, but allows also for accurate manufacturing and hence for accurately tailoring of lenses providing target focal points and a targeted light distribution among the target focal points.

The trifocal properties of the ophthalmic lens according to the present disclosure may be limited to a first area in radial direction of the surface of the lens body including the optical axis. Further outwards in radial direction of the lens beyond the first area and towards the circumferential edge thereof, the lens may comprise a second area having bifocal properties, for example. Such as only providing focal points for intermediate and far vision at this second area.

In practice, numerical methods may be required for calculating the phase function or phase profile function optimizing overall efficiency of light distribution in the refractive and diffractive focal points of a symmetric or asymmetric beam splitter having focal points for near and far vision different than the first diffractive orders ±1 as elucidated above.

It is further noted that the teachings according to the present disclosure are equally applicable for designing and tuning the light distribution of a multifocal ophthalmic lens having four target focal points, i.e. a so-called quad-focal lens, or even a multifocal ophthalmic lens having five target focal points, i.e. a so-called penta-focal lens.

In a second aspect, the present disclosure provides a method of manufacturing an ophthalmic multifocal lens, at least comprising focal points for near vision, intermediate vision and far vision, having a light transmissive lens body comprising an optical axis providing a refractive focal point, and a periodic light transmissive diffraction grating, extending concentrically in radial direction across at least part of a surface of the lens body providing a set of diffractive focal points, wherein the diffraction grating is designed to operate as an optical wave splitter for distributing light incident at the lens body in the refractive and diffractive focal points, the refractive focal point providing the focal point for intermediate vision and the diffractive focal points providing the focal points for near vision and far vision, the method comprising the steps of:

determining target focal points for near vision, intermediate vision and far vision;
determining a target light distribution of incident light in the target focal points;
providing the light transmissive lens body having a refractive focal point providing the target focal point for intermediate vision;
providing the diffraction grating having an optical transfer function comprising a continuous periodic phase profile function extending in radial direction of the lens body providing the target focal points for near vision and far vision and a distribution of light in the target focal points,
characterized by the steps of:
providing the continuous periodic phase profile function having a modular argument as a function of radial distance to the optical axis of the lens body,
tuning the distributing of light in the target focal points for providing the target light distribution by modulating the argument across the lens body, providing a modulated argument,
providing a height profile of the diffraction grating in accordance with the periodic phase profile function comprising the modulated argument, and
producing the ophthalmic multifocal lens by applying the diffraction grating in accordance with the height profile at the lens body.

The height profile of the diffraction grating of the lens, specifying the height and position of the varies DOEs that extend as ring, oval or other rotational shaped zones at the surface of the lens concentric to the optical axis or center of the lens, can be applied in the lens body by any of laser micro machining, diamond turning, 3D printing, or any other machining or lithographic surface processing technique, for example. A lens with the same optical effect can also be created by holographic means, using a holographic optical element to spread the light to the desired foci.

The lens body may comprise any of Hydrophobic Acrylic, Hydrophilic Acrylic, Silicone materials, or any other suitable light transmissive material.

In the method according to the present disclosure, the argument of the continuous periodic phase profile function may be modulated for producing the ophthalmic multifocal lens in accordance with the first aspect of the present disclosure, in particular for providing a lens having different target light distributions in the target focal points for different pupil sizes.

Although the continuous periodic phase profile function may be calculated mathematically analytically, in accordance with the present disclosure, the phase profile function of the diffraction grating of the lens may be provided by computer calculations, wherein the phase profile function is represented by a Fourier series and each diffraction order is represented by a respective Fourier coefficient. The phase profile function may be calculated such that a summation of squared absolute values or weighted squared absolute values of Fourier coefficients of diffraction orders associated with the target focal points is maximum.

The continuous phase profile function and the height profile of the lens in the method according to the present disclosure may be provided remote from the equipment for manufacturing the lens. Particularities of the height profile of the diffraction grating of the lens may be forwarded to the manufacturing site or equipment by data transfer over a telecommunication network available in practice, such as the Internet.

Tuning and smoothing of the optical properties and the light distribution in the target refractive and diffractive focal points may be applied such that the amount of light diffracted in a particular focal point or order is spread or smeared out over part of the optical axis, to provide an ophthalmic lens having enhanced depth of focus, ED, properties.

In a third aspect the present disclosure provides an ophthalmic multifocal lens as disclosed above, arranged as one of a contact lens, an intraocular lens, an aphakic contact lens, an aphakic intraocular lens, and a spectacle lens. It is to be noted that in the case of an intraocular lens, the lens body generally takes the form of biconvex or plano-convex optically transparent disk. In the case of a contact lens or spectacle or eye-glass lens, the lens body may take any of a biconvex or plano-convex and biconcave or plano-concave shape or combinations thereof, whether or not enhanced by further optical corrections arranged at or in the optically transparent body.

These and other aspects of the disclosure will be apparent from and elucidated with reference to the examples described hereinafter.

BRIEF DESCRIPTION OF THE DRAWINGS

FIG. 1 illustrates, in a schematic manner, focusing of light beams from several distances at the human eye.

FIG. 2a illustrates, in a schematic manner, a top view of a typical prior art multifocal aphakic intraocular lens.

FIG. 2b illustrates, in a schematic manner, a side view of the multifocal aphakic intraocular lens shown in FIG. 2a.

FIGS. 5a-25b, schematically, graphically illustrate examples of height profiles, argument modulation parameters and argument modulation functions of diffraction gratings on a biconvex lens body in accordance with the present disclosure, and corresponding computer simulated light intensity distributions.

DETAILED DESCRIPTION

Figure 3:
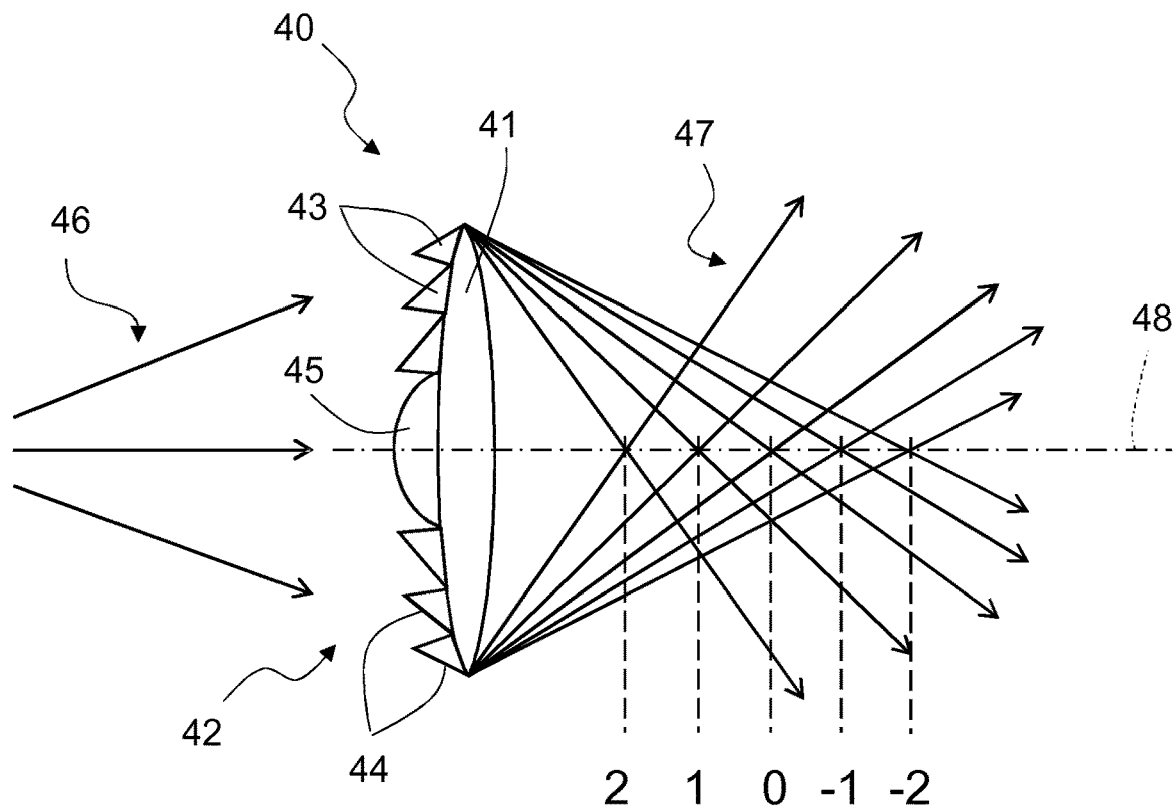
FIG. 3 illustrates, in a schematic manner, in a cross-sectional view, the optical operation of a prior art diffractive lens comprising a biconvex light transmissive body and a light transmissive diffraction grating.

FIG. 1 shows, in a simplified manner, the anatomy of the human eye 10, for the purpose of illustrating the present disclosure. The front part of the eye 10 is formed by the cornea 11, a spherical clear tissue that covers the pupil 12. The pupil 12 is the adaptable light receiving part of the eye 10 that controls the amount of light received in the eye 10. Light rays passing the pupil 12 are received at the natural crystalline lens 13, a small clear and flexible disk inside the eye 10, that focuses light rays onto the retina 14 at the rear part of the eye 10. The retina 14 serves the image forming by the eye 10. The posterior chamber 15, i.e. the space between the retina 14 and the lens 13, is filled with aqueous humour, and the anterior chamber 16, i.e. the space between the lens 13 and the cornea 11, is filled with vitreous humour a clear, jelly-like substance. Reference numeral 20 indicates the optical axis of the eye 10.

For a sharp and clear far field view by the eye 10, the lens 13 should be relatively flat, while for a sharp and clear near field view the lens 13 should be relatively curved. The curvature of the lens 13 is controlled by the ciliary muscles (not shown) that are in turn controlled from the human brain. A healthy eye 10 is able to accommodate, i.e. to control the lens 13, in a manner for providing a clear and sharp view of images at any distance in front of the cornea 11, between far field and near field.

Ophthalmic or artificial lenses are applied to correct vision by the eye 10 in combination with the lens 13, in which cases the ophthalmic lens is positioned in front of the cornea 11, or to replace the lens 13. In the latter case also indicated as aphakic ophthalmic lenses.

Multifocal ophthalmic lenses are used to enhance or correct vision by the eye 10 for various distances. In the case of trifocal ophthalmic lenses, for example, the ophthalmic lens is arranged for sharp and clear vision at three more or less discrete distances or focal points, generally called far, intermediate and near vision, in FIG. 1 indicated by reference numerals 17, 18 and 19, respectively. Light rays emanating from objects arranged at or near these distances or focal points 17, 18 and 19 are correctly focused at the retina 14, i.e. such that clear and sharp images of these objects are projected. The focal points 17, 18 and 19, in practice, may correspond to focal distances ranging from a few meters, to tens of centimeters, to centimeters, respectively.

The amount of correction that an ophthalmic lens provides is called the optical power, OP, and is expressed in Diopter, D. The optical power OP is calculated as the inverse of a focal distance f measured in meters. That is, $OP=1/f$, wherein f is a respective focal distance from the lens to a respective focal point for far 17, intermediate 18 or near vision 19. The optical power of a cascade of lenses is found by adding the optical powers of the constituting lenses, for example. The optical power of a healthy human lens 13 is about 20 D.

FIG. 2a shows a top view of a typical ophthalmic multifocal aphakic intraocular lens 30, and FIG. 2b shows a side view of the lens 30. The lens 30 comprises a light transmissive circular disk-shaped lens body 31 and a pair of haptics 32, that extend outwardly from the lens body 31, for supporting the lens 30 in the human eye. The lens body 31 has a biconvex shape, comprising a center part 33, a front or anterior surface 34 and a rear or posterior surface 35. The lens body 31 further comprises an optical axis 29 extending transverse to front and rear surfaces 34, 35 and through the center of the center part 33. Those skilled in the art will appreciate that the optical axis 29 is a virtual axis, for the purpose of referring the optical properties of the lens 30. The convex lens body 31, in a practical embodiment, provides a refractive optical power of about 20D.

In the embodiment shown, at the front surface 34 of the lens body 31 a periodic light transmissive diffraction grating or relief 36 is arranged, comprised of rings or zones extending concentrically with respect to the optical axis 29 through the center part 33 over at least part of the front surface 34 of the lens body 31. The diffraction grating or relief 36 provides a set of diffractive focal points. Although not shown, the diffraction grating or relief 36 may also be arranged at the rear surface 35 of the lens body 31, or at both surfaces 34, 35. In practice, the diffraction grating 36 is not limited to concentric circular or annular ring-shaped zones, but includes concentric elliptic or oval shaped zones, for example, or more in general any type of concentric rotational zone shapes.

In practice the optic diameter 37 of the lens body 31 is about 5-7 mm, while the total outer diameter 38 of the lens 30 including the haptics 31 is about 12-14 mm. The lens 30 may have a center thickness 39 of about 1 mm. In the case of ophthalmic multifocal contact lenses and spectacle or eye glass lenses, the haptics 32 at the lens body 31 are not provided, while the lens body 31 may have a plano-convex, a biconcave or plano-concave shape, or combinations of convex and concave shapes. The lens body may comprise any of Hydrophobic Acrylic, Hydrophilic Acrylic, Silicone materials, or any other suitable light transmissive material for use in the human eye in case of an aphakic ophthalmic lens.

FIG. 3 schematically illustrates, the optical operation of a known periodic light transmissive diffraction grating or relief 42 of a lens 40 comprising a biconvex light transmissive circular disk-shaped lens body 41. The lens 40 is shown in a cross-sectional view in radial direction of the lens body. The diffraction grating or relief 42 comprises a plurality of repetitive, contiguously arranged, prism shaped transparent diffractive optical elements, DOEs, 43. The DOEs 43 extend in concentric zones around the center part 45 of the lens body 41, in a manner similar to the rings or zones of the grating or relief 36 shown in FIG. 2a. For illustrative purposes, the DOEs 43 of the diffraction grating 42 are shown as well-known jagged or saw-tooth type elements, comprising a continuous, sloping light receiving surface 44, such as a linear or curved sloping light receiving surface 44. Gratings or reliefs in which the DOEs 43 are spaced apart in radial direction of the lens body 41, are called binary type reliefs (not shown). The repetition period or pitch of the DOEs 43 monotonically decreases in radial direction from the center or optical axis of the lens and various with the square of the radial distance.

An incident or primary light beam 46 that passes the grating 42 and the lens body 41 is, respectively, diffracted and refracted and results in an output or secondary light beam 47. The refracted and diffracted light waves 47 form a plurality of focal points at the optical axis 48 of the lens 40, due to constructive interference of the light waves 47. Constructive interference occurs when the optical path difference between light waves 47 arriving from the lens body 41, at a particular focal point, is an integer multiple of their wavelength, i.e. the light waves are in-phase, such that their amplitudes add-up in a reinforcing manner. When the difference in optical path length travelled by interfering light waves 47 from the lens body 41 is an odd multiple of half of the wavelength, such that a crest of one wave meets a trough of another wave, the light waves 47 partly or completely extinguish each other, i.e. the light waves are out of phase, not resulting in focal points at the optical axis 48 of the lens body 41.

The points of constructive interference at various distances from the lens body 41 are generally designated diffraction orders. The focal point that corresponds to the focal point that originates due to refractive operation of the curvature of the lens 40 is indicated by order zero, 0. The other focal points are designated by orders +1, +2, +3, etc. if the respective focal point occurs at the left-hand side of the zero order when viewed in the plane of the drawing, i.e. at a distance in the direction towards the lens body 41, and designated by order −1, −2, −3, etc. if the respective focal point occurs at the right-hand side of the zero order when viewed in the plane of the drawing, i.e. at a distance in the direction away from the lens body 41. Such as illustrated in FIG. 3.

The diffraction relief 42 can be designed to provide focal points at different distances from the lens body 41. The periodic spacing or pitch of the DOEs 43 substantially determines where the points of destructive and constructive interference occur at the optical axis 48 of the lens, i.e. the position of the diffractive orders at the optical axis 48. By the shape and height of the DOEs 43 the amount of incident light that is provided at a point of constructive interference, i.e. at or in a particular diffraction order, is controlled.

In case of a diffraction grating or relief 42 providing diffraction orders that are regularly spaced at both sides of the zero order, the grating or relief is called a symmetric wave splitter, as the incident light beam 45 is symmetrically diffracted or split with respect to the zero order. A grating or relief producing a non-regular spacing of diffractive orders, such as +1, +2, −3, −5 is called an asymmetric beam splitter.

The light energy in light waves 47 that are focussed or diffracted in focal points or orders that do not contribute to image forming at the retina 14 of the human eye 10 is lost and reduces the overall efficiency of the lens 40, and hence the quality of images perceived by a human being using such lens. In practice, for optimally designing a lens, it is advantageous if the focal points for providing or correcting far, intermediate and near vision to the human eye, such as illustrated in FIG. 1, for example, can be set beforehand, and a diffraction grating 42 is provided that maximizes the overall efficiency of the light energy received from the incident light beam 46 in these pre-set focal points is optimal.

In scientific literature, a diffraction grating optimizing overall efficiency of light distribution in pre-set or target refractive and diffractive focal points or orders is found from determining a phase-only function or phase profile that generates the target diffraction orders with a maximum overall efficiency n or figure of merit defined as the sum of the normalized light energies of all these target orders.

Those skilled in the art will appreciate that the lens body 41 may comprise a plano-convex, a biconcave or plano-concave shape, and combinations of convex and concave shapes or curvatures (not shown).

Assuming a circular, disk-shaped lens having a diffraction grating as shown in FIGS. 2a, 2b and 3, for example. If the phase profile function of the diffraction grating is denoted by $\varphi(r)$, the optical transfer function of the grating to be determined is given by: $T(r)=\exp[i\ \varphi(r)]$, wherein exp represents the exponential function, i represents the unit imaginary number, and r represents the radial distance or radius from the center or optical axis of the lens body in which the repetitive DOEs extend.

As the diffraction grating is a periodic repetitive structure, $T(r)$ can be expanded into its Fourier series:

$$T(r) = \sum_{n=-\infty}^{n=\infty} \tau_n \exp\left[\frac{i2\pi n r}{P}\right] \qquad (3)$$

wherein $\tau_n$ represents the Fourier coefficient of the $n^{th}$ diffraction order and P is the period or pitch of the diffraction grating and n is a positive integer value inclusive zero.

Maximizing the overall efficiency requires that the sum of the normalized energies of the target focal points or orders equals 1, that is:

$$\sum_{n=-\infty}^{n=\infty} |\tau_n|^2 = 1. \qquad (4)$$

In the case of a wave splitting trifocal ophthalmic lens, for example, wherein the refractive focal point represents the focal point of intermediate vision, and the diffractive focal points represent the focal points for near and far vision, respectively, $|\tau_{-m}|^2+|\tau_0|^2+|\tau_p|^2$ should be optimized, wherein the indices −m, 0 and p represent the diffraction order providing the focal point for near vision, the refractive focal point providing intermediate vision, and the diffraction order providing the focal point for far vision, respectively. The optimum phase function may also be derived dependent on weighted light intensities or light energies in the target focal points.

The value of the diffraction orders −m and p need not be equal. In the present disclosure, in the case that the value of m equals the value of p, such as m=p=1, the wave splitter is called a symmetric wave splitter, whereas if the values of m and p are different, the wave splitter is called asymmetric.

In accordance with the present disclosure, a general expression for a continuous periodic phase profile function is provided by:

$$\phi(r) = A(r) * F\left[\alpha(r) * G\left(\frac{2\pi\{r^2 - S(r)\}}{T}\right)\right] + B(r) \qquad (1)$$

wherein:

$\phi(r)$ is a continuous periodic phase profile function of the diffraction grating, r is the radial distance or radius outwardly from the optical axis of the lens body, [mm], $A(r)$ is an amplitude modulation function of the continuous periodic phase profile function in radial direction of the lens body, $F[\alpha*G]$ is a function in radial direction of the lens body providing the wave splitter operation, $G(r)$ is a periodic function in $r^2$ space, $\alpha(r)$ is an argument magnitude modulation function of G, $S(r)$ is an argument angle modulation function of G in $r^2$ space, [mm$^2$], T is a period or pitch of the diffraction grating in $r^2$ space, [mm$^2$], and B(r) is an amplitude modulation function of the continuous periodic phase profile function.

Following the present disclosure, for controlling or tuning the amount of light distributed in the focal points, argument modulation of the continuous periodic function F[α*G] as a function of the radius or radial distance at the lens body is provided by the argument magnitude modulation function α(r) of G(r) and the argument angle modulation function S(r) of G(r). Amplitude modulation functions A(r) and B(r) provide a further control or tuning of the amount of light that is distributed between the focal points of diffraction and the focal point of refraction.

Figure 4:
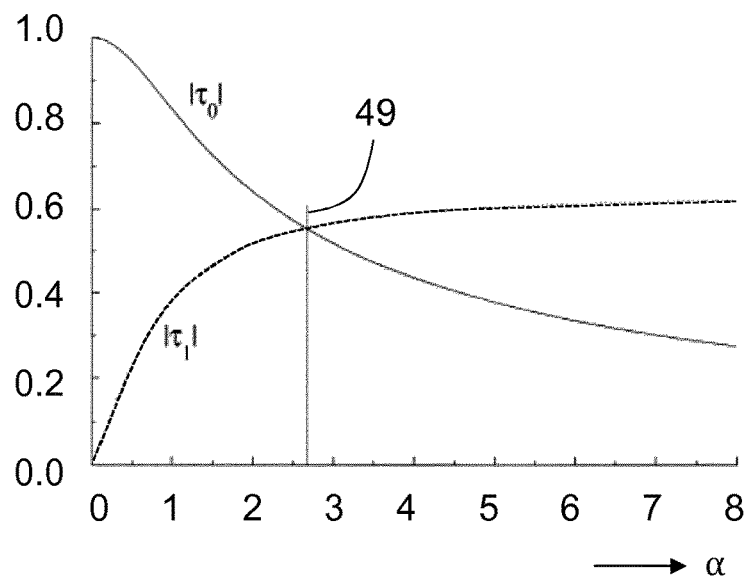
FIG. 4 illustrates, in a schematic, graphic manner the relative energy distribution between the target diffraction orders for an optimum efficiency symmetrical planar beam splitter as a function of a constant argument magnitude modulation function $\alpha(r)$.

FIG. 4 graphically illustrates the relative energy distribution between the first diffraction orders ±1, represented by the dotted line |τ$_1$|, and the zero order, represented by the solid line |τ$_0$| in the case of a constant value of the argument magnitude modulation function α(r) for a linear or planar optimum triplicator diffraction grating having a continuous periodic phase profile function:

$$\phi(r) = \tan^{-1}\left[\alpha(r) * \sin\left(\frac{2\pi r^2}{T}\right)\right] \quad (5)$$

Equation (5) is presented by F. Gori et al. in the publication titled "Analytical derivation of the optimum triplicator", in Optics Communication 157 (1998), p. 13-16.

The light distribution parameter α(r) determines the amount of light that is distributed among the ±1 diffractive orders and the 0th order. In accordance with equation (5), for a value of α=2.65718, indicated by reference numeral 49 in FIG. 4, light energy is evenly distributed among all the target focal points, i.e. the ±1 diffractive orders and the 0th order. The overall efficiency η that can be achieved with such a phase profile function φ(r) is above 0.925.

In an embodiment of the ophthalmic multifocal lens according to the present disclosure, based on the phase profile function φ(r) disclosed in equations (1) and (2) above, the height profile or height function H(r) of the diffraction grating of the actual lens is expressed in a single continuous closed-form function defined by:

$$H(r) = A(r) * \frac{\lambda}{n - n_m} * \frac{\tan^{-1}\left[\alpha(r)\sin\left(\frac{2\pi\{r^2 - S(r)\}}{T}\right)\right]}{2\pi} + B(r) * \frac{\lambda}{2\pi(n - n_m)} \quad (6)$$

wherein:

H(r) height profile of the lens, [nm],

λ is the design wavelength of the lens, [nm], n is the index of refraction of the lens body, n$_m$ is the index of refraction of the medium surrounding the lens body.

FIGS. 5a-22f schematically, graphically, illustrate examples of the height profile or height function H(r) of equation (6) and computer simulated light intensity distributions of a biconvex lens body 31 of an ophthalmic lens 30 of the type shown in FIGS. 2a, 2b, comprising such height profiles. The lens 30 is designed for targeting a zero order focal point at 20 diopter, D, and first order focal points at 21.5 D and 18.5 D, symmetrically positioned with respect to the zero order. That is, providing a focal point for intermediate vision at 20 D for the zeroth order focal point, providing a focal point for far vision at 18.5 D by diffraction order −1, and providing a focal point for near vision at 21.5 D by the +1 diffraction order. Those skilled in the art will appreciate that these optical powers or focal points may differ for actual lenses, dependent on the target focal points. The examples are calculated using MATLAB™ based simulation software.

The height of the height profile H(r) is depicted at μm scale along the vertical axis. The optical axis, running through the center of the lens body, is assumed to be at a radial position r=0, whereas the radial distance r measured in outward direction from the optical axis is expressed in mm along the vertical axis. In the intensity profiles, the intensity I of the diffracted light is depicted in arbitrary units along the vertical axis as a function of the optical power in diopter, D, depicted along the horizontal axis.

In these designs, the design wavelength λ of the lens is assumed 550 nm, the index of refraction n of the lens body is set to 1.4618, and the index of refraction n$_m$, of the medium surrounding the lens body is assumed 1.336. If not otherwise indicated, the amplitude modulation function A(r) =1, the amplitude modulation function B(r)=0 and the argument magnitude modulation function α(r)=2.65718. The period T=0.733 mm$^2$ in r$^2$ space.

Figure 5A:
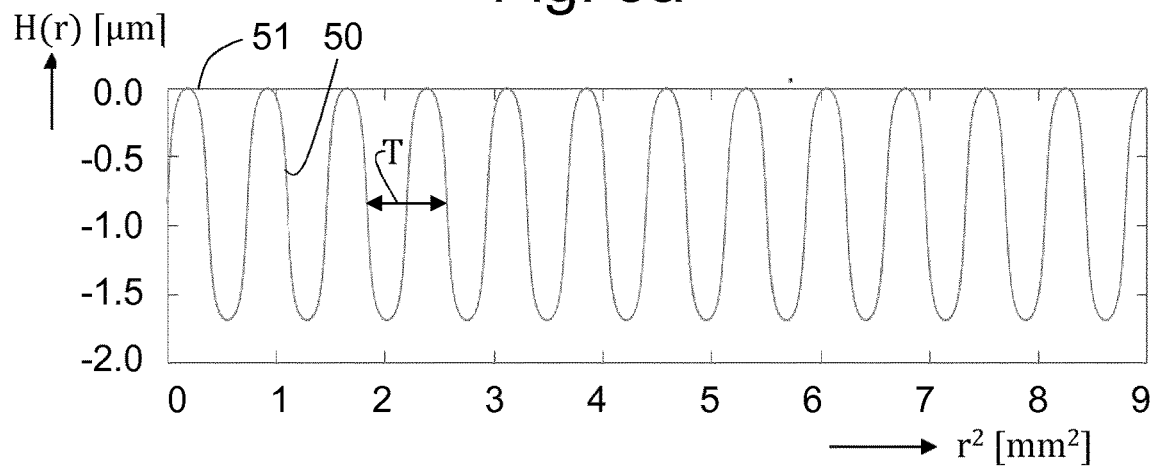
Figure 5B:
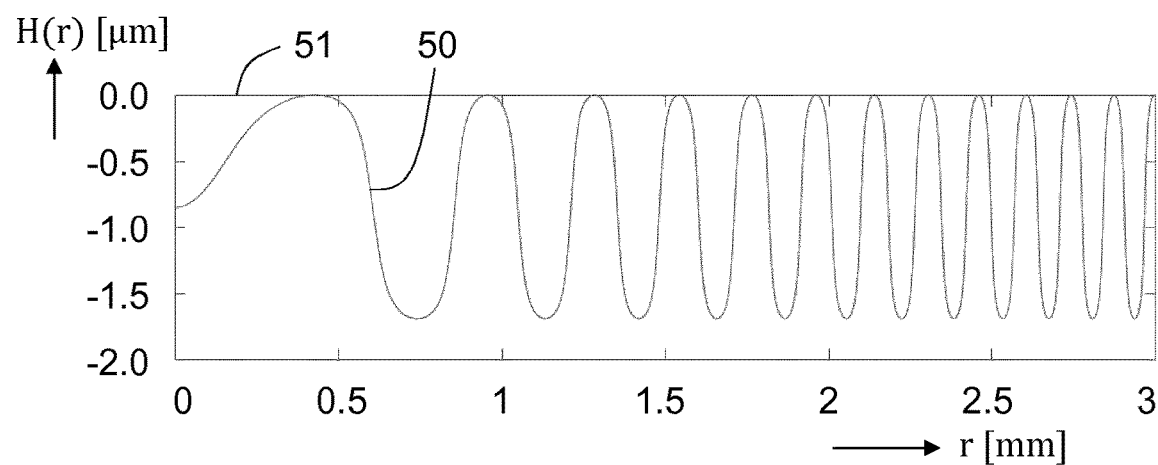

Reference numeral 50 in FIG. 5a shows the height profile or height function H(r) according to equation (6) in r$^2$ space, expressed in mm$^2$ and FIG. 5b shows the same height function along a linear scale as function of the radial distance r. In this example, the argument angle modulation function S(r)=0, i.e. no phase shift or argument angle modulation.

Reference numeral 51 refers to the outer circumference of the front surface 34 of the lens body 30 having a diffraction grating or relief 36 comprising the diffraction profile function H(r) 50. See FIGS. 2a and 2b.

As can be viewed from FIG. 5a, in r$^2$ space each period T of the height profile H(r) 50 is depicted with an equal or equidistant length. The height profile or height function H(r) is a single, closed-form continuous geometric function defining concentrically arranged DOEs having no sharp transitions which are difficult to manufacture in the lens body. Accordingly, the height profile H(r) 50 of the diffraction grating not only provides optimum efficiency, but allows accurate manufacturing and hence accurately tailoring of the lenses providing target focal points and a target light distribution among the target focal points.

Figure 5C:
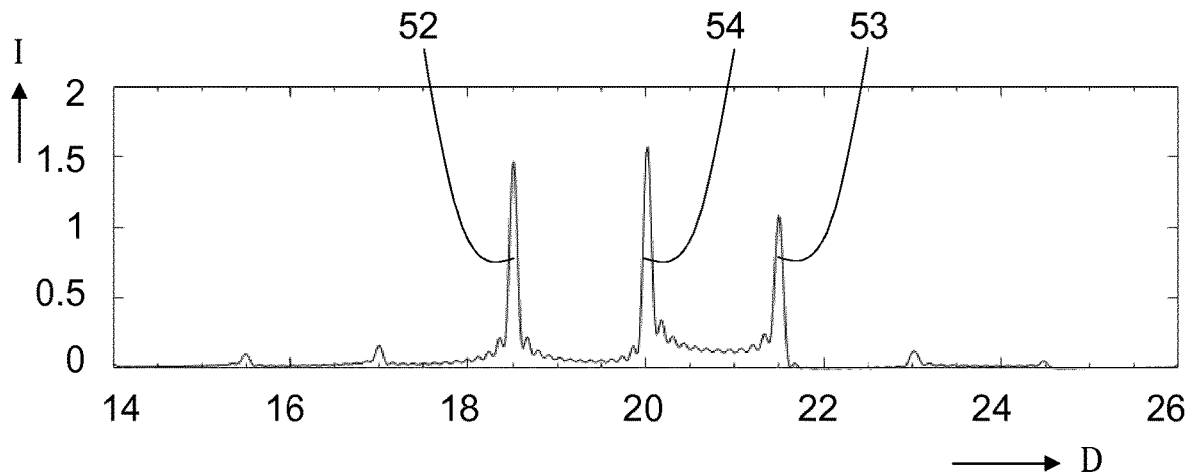

The amount of light diffracted by the lens having the height profile H(r) 50 is shown in the intensity simulation of FIG. 5c. Reference numeral 54 refers to diffraction order 0, providing a focal point for intermediate vision, reference numeral 52 refers to diffraction order −1, providing a focal point for far vision, and reference numeral 53 refers to the +1 diffraction order, providing a focal point for near vision. As can be seen from FIG. 5c, different from the lens phase profile calculated for the planar optimal triplicator by Gori et al., for α(r)=2.65718 the amount of light incident at the curved lens body is not distributed equally in the target focal points. This, because the optimum triplicator periodic phase profile function by Gori et al. is calculated for a linear or planar phase grating lens for which the distances between the periods show a linear dependency, while by transforming same into a lens, the distances between the periods of the phase profile function comprise a square root dependency.

FIG. 6a shows the height profile H(r) according to equation (6) above as a function of the radial distance r, however modulated by a constant argument angle modulation S=0.25*T, indicated by reference numeral 60. Reference numeral 61 refers to the outer circumference of the front surface 34 of the lens body 30.

The amount of light diffracted by the lens is shown in the simulation of FIG. 6b. Reference numeral 64 refers to diffraction order 0, reference numeral 62 refers to diffraction order −1, and reference numeral 63 refers to the +1 diffraction order. As can be seen from FIG. 6a, by this argument angle modulation S relatively more light is diffracted in the +1 order compared to the height profile 50 having no argument angle modulation S.

An argument angle modulation in the other direction, i.e. S=−0.25*T illustrated by the height profile 70 shown in FIG. 7a, shows that relatively most light is diffracted in the order +1 corresponding to the focal point for near vision 73, as show in the intensity profile of FIG. 7b. From FIG. 7b it can be seen that relatively less light is diffracted in the −1 order 72, hence this modulation provides a relative strong promotion of the light intensity for near vision. Reference numeral 71 refers to the outer circumference of the front surface 34 of the lens body 30 having a diffraction grating or relief 36 comprising the diffraction profile function H(r) 70.

By the shift of the phase function, i.e. the height profile, the relative amount of light between the diffraction orders can be controlled or tuned to provide a target light distribution of the lens and/or to correct for tolerances and other production deviations in manufacturing the lens, for example.

As indicated above, it is advantageous to express the argument angle modulation S as a fraction of the period T of the grating in $r^2$ space. In practical embodiments, the argument angle modulation may range between about S=−0.5*T and about S=0.5*T in $r^2$ space, including integer multiples of the period T, dependent on the required correction of light between the near, intermediate and far vision focal points.

Figure 8A:
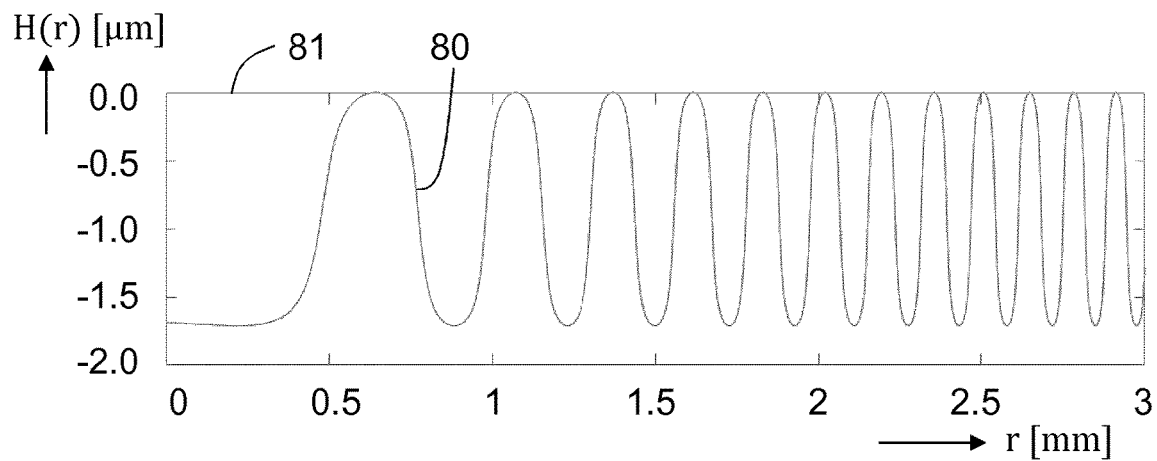
Figure 8B:
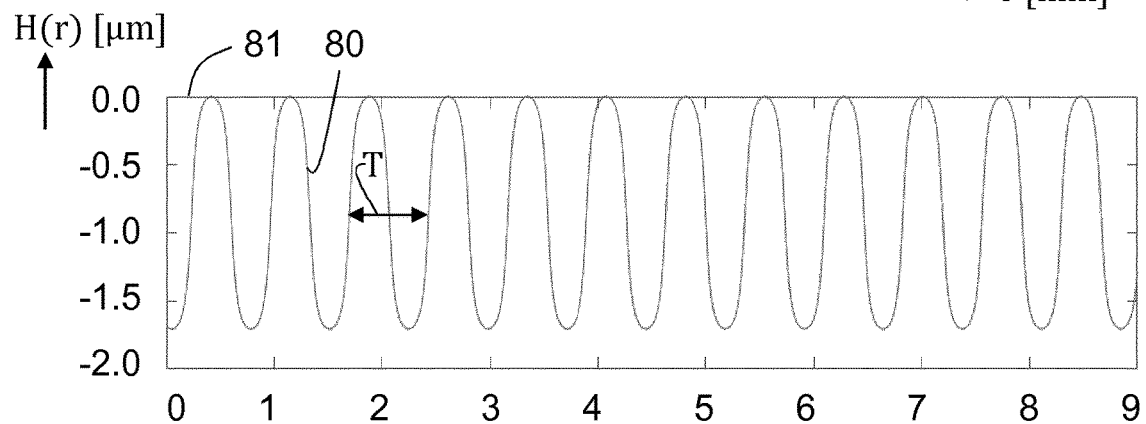

FIG. 8a shows a height profile or height function H(r) according to equation (6) above, as a function of the radial distance r of a diffraction grating in an embodiment of a trifocal intraocular ophthalmic lens according to the present disclosure, indicated by reference numeral 80. FIG. 8b shows the height profile 80 in the $r^2$ space. The argument angle of the height profile 80 of the diffraction grating is modulated by a modulation function S(r) having a fixed value S=0.315*T, and the amplitude modulation function A(r)=1.013. Reference numeral 81 refers to the outer circumference of the front surface 34 of the lens body 30 having a diffraction grating or relief 36 comprising the diffraction profile function H(r) 80.

Figure 8C:
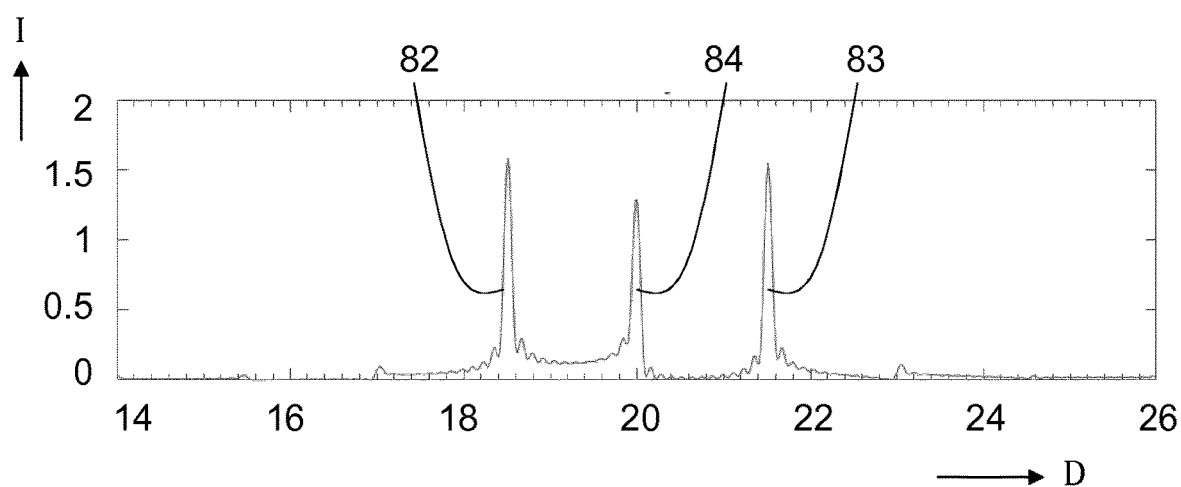

The light distribution achieved by the diffraction grating having the height profile 80 is shown in FIG. 8c. As can be seen from FIG. 8c, in the focal points for far vision 82 and near vision 83 an even amount of light is diffracted, whereas in the focal point 84 for intermediate vision relatively less light is distributed.

Figure 9A:
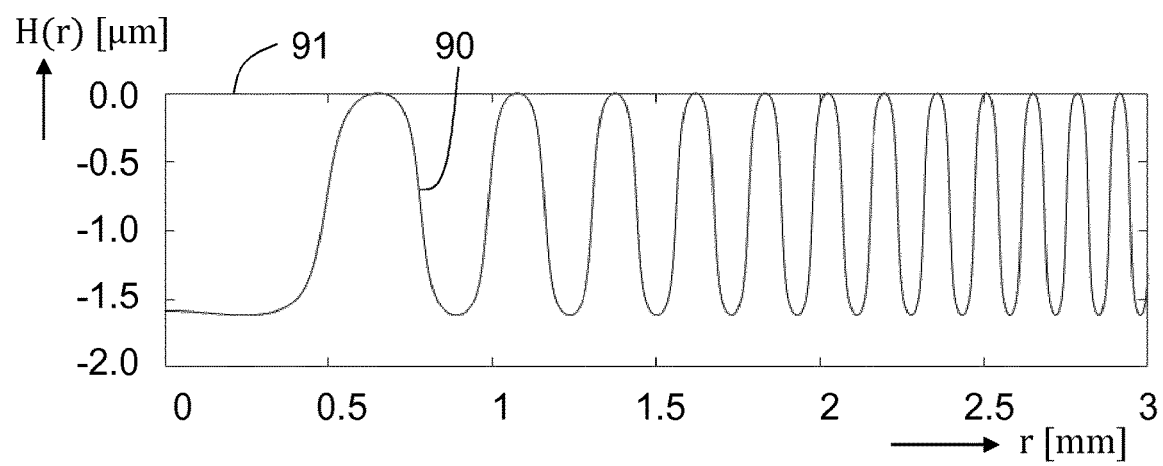

FIG. 9a shows a height profile or height function H(r) according to equation (6) above, as a function of the radial distance r of a diffraction grating in an embodiment of a trifocal intraocular ophthalmic lens according to the present disclosure, indicated by reference numeral 90. The argument angle of the height profile 90 is modulated by a modulation function S(r) having afixed value S=0.33*T, and the amplitude modulation function A(r)=0.96. Reference numeral 91 refers to the outer circumference of the front surface 34 of the lens body 30 having a diffraction grating or relief 36 comprising the diffraction profile function H(r) 90.

Figure 9B:
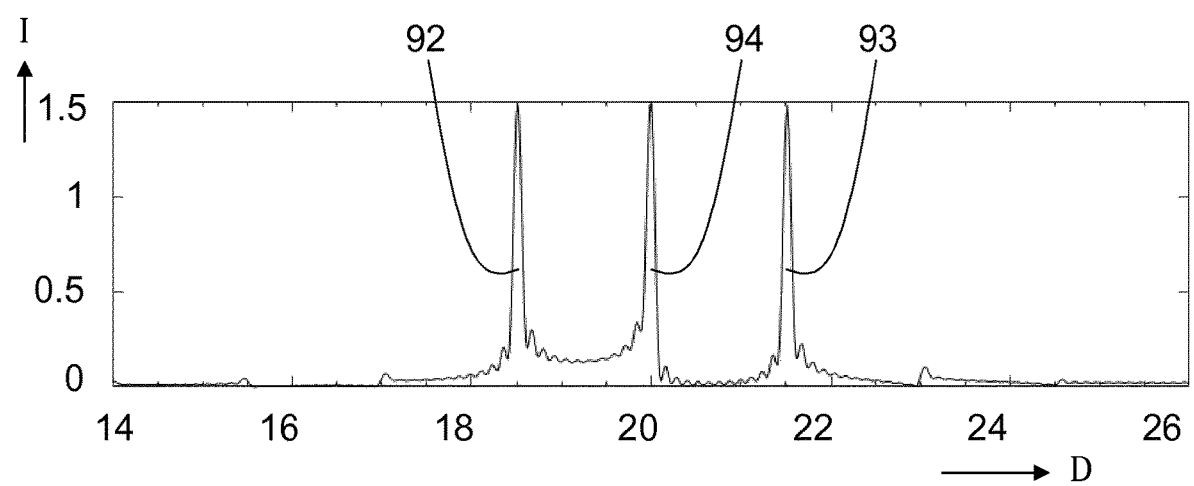

The light distribution achieved by the diffraction grating having the height profile 90 is shown in FIG. 9b. As can be seen from FIG. 9b, with the above-mentioned argument modulation parameters, in the focal points for far vision 92, near vision 93, and the focal point for intermediate vision 94 an even amount of light is distributed.

Instead of a fixed value of the argument angle modulation function S(r) and/or the argument magnitude modulation function or light distribution parameter α(r), and any or both of the amplitude modulation functions A(r) and B(r), as illustrated above, in accordance with the present disclosure, the argument angle and argument magnitude modulation functions S(r) and/or α(r), respectively, and the amplitude modulation functions A(r) and B(r) may comprise modulation functions varying across and with the radial distance to the optical axis of the lens body, for achieving a respective target light distribution or focus enhancement by tuning the light distribution in the target focal points or target foci, in particular for providing a pupil dependent light distribution in the focal points.

FIGS. 10a-13c are provided to illustrate the effect on the light distribution of an ophthalmic multifocal lens according to the present disclosure, wherein the argument of the continuous periodic profile function is modulated by a periodic argument angle modulation function or a periodic argument magnitude modulation function, providing periodic transitions in the continuous periodic phase profile function, i.e. the height profile of the lens.

FIG. 10a shows a height profile or height function H(r) 100 according to equation (6) above, as a function of the radial distance r of a diffraction grating in an example of a trifocal intraocular ophthalmic lens according to the present disclosure, modulated by a periodic argument angle modulation function S(r) 105, shown in FIG. 10b. The argument angle modulation function 105 is a periodic square wave function having a period equal to a period of the continuous periodic height function 100. The value of S(r) 105 ranges between S=±0.07*T, as indicated along the vertical axis in FIG. 10b. Reference numeral 101 refers to the outer circumference of the front surface 34 of the lens body 30 having a diffraction grating or relief 36 comprising the diffraction profile function H(r) 100.

In the example shown, an upward or leading edge 106 of the argument angle modulation function 105 causes a transition 108 providing a displacement of the height profile function 100, i.e. the continuous periodic phase profile function of the diffraction grating, in outward radial direction r of the lens body, situated at a leading edge or upward flank of the height profile function 100. A downward or trailing edge 107 of the argument angle modulation function 105 causes a transition 109 providing a displacement of the height profile function 100 in inward radial direction of the lens body, counteracting the displacement by the transition 108, and situated at a trailing edge or downward flank of the height profile function 100.

The light distribution achieved by the diffraction grating having the height profile 100 is shown in FIG. 10c. As can be seen from FIG. 10c, with the above-mentioned argument angle modulation function 105, relatively more light is distributed or coupled in the focal point for far vision 102 compared to the focal point for near vision 103. The amount of light distributed in the focal point for intermediate vision 104 is substantially equal to the amount of light distributed in the focal point for intermediate vision 54 of the height profile 50 shown in FIG. 5, having no argument angle modulation.

Accordingly, with the argument angle modulation function 105 a strong promotion of the relative amount of light in the focal point 102 for far vision is achieved.

FIG. 11a shows a height profile or height function H(r) 110 according to equation (6) above, as a function of the radial distance r of a diffraction grating in an example of a trifocal intraocular ophthalmic lens according to the present disclosure, modulated by a periodic argument angle modulation function S(r) 115, shown in FIG. 11b. The argument angle modulation function 115 is a periodic square wave function having a period equal to a period of the continuous periodic height function 110. The value of S(r) 115 ranges between S=±0.07*T, as indicated along the vertical axis in FIG. 11b. Reference numeral 111 refers to the outer circumference of the front surface 34 of the lens body 30 having a diffraction grating or relief 36 comprising the diffraction profile function H(r) 110.

In the example shown, an upward or leading edge 116 of the argument angle modulation function 115 causes a transition 118 providing a displacement of the height profile function 110, i.e. the continuous periodic phase profile function of the diffraction grating, in outward radial direction r of the lens body, situated at a trailing edge or downward flank of the height profile function 110. A downward or trailing edge 117 of the argument angle modulation function 115 causes a transition 119 providing a displacement of the height profile function 110 in inward radial direction of the lens body, counteracting the displacement by the transition 118, and situated at a leading edge or upward flank of the height profile function 110.

The light distribution achieved by the diffraction grating having the height profile 110 is shown in FIG. 11c. As can be seen from FIG. 11c, with the above-mentioned argument angle modulation function 115, relatively more light is distributed or coupled in the focal point for near vision 113 compared to the focal point for far vision 112. The amount of light distributed in the focal point for intermediate vision 114 is substantially equal to the amount of light distributed in the focal point for intermediate vision 54 of the height profile 50 shown in FIG. 5, having no argument angle modulation.

Accordingly, with the argument angle modulation function 115 a strong promotion of the relative amount of light in the focal point 113 for near vision is achieved.

FIG. 12a shows a height profile or height function H(r) 120 according to equation (6) above, as a function of the radial distance r of a diffraction grating in an example of a trifocal intraocular ophthalmic lens according to the present disclosure, modulated by a periodic argument magnitude modulation function α(r) 125, shown in FIG. 12b. The argument magnitude modulation function 125 is a periodic square wave function having a period equal to a period of the continuous periodic height function 120. The value of α(r) 125 is normalized with respect to the value of α=2.65718, as indicated along the vertical axis in FIG. 12b, and ranges between 1.4≥α(r)/2.65718≥0.7. The argument angle modulation function S(r)=0 for the height profile function 120. Reference numeral 121 refers to the outer circumference of the front surface 34 of the lens body 30 having a diffraction grating or relief 36 comprising the diffraction profile function H(r) 120.

In the example shown, an upward or leading edge 126 of the argument magnitude modulation function 125 causes a transition 128 providing a displacement of the height profile function 120, i.e. the continuous periodic phase profile function of the diffraction grating, in a direction transverse to the at least one surface 34 of the lens body 30 and upwards in the direction to the outer circumference 121. The transition 128 is situated at the top or crest of the height profile function 120. A downward or trailing edge 127 of the argument magnitude modulation function 125 causes a transition 129 providing a displacement of the height profile function 120, i.e. the continuous periodic phase profile function of the diffraction grating, in a direction transverse to the at least one surface 34 of the lens body 30 downwards, i.e. away from the outer circumference 121. The transition 129 is situated at the bottom or trough of the height profile function 120 and counteracts the displacement by the transition 128.

The light distribution achieved by the diffraction grating having the height profile 120 is shown in FIG. 12c. As can be seen from FIG. 12c, with the above-mentioned argument magnitude modulation function 125, relatively more light is distributed or coupled in the focal point for far vision 122 compared to the focal point for near vision 123. The amount of light distributed in the focal point for intermediate vision 124 is substantially equal to the amount of light distributed in the focal point for intermediate vision 54 of the height profile 50 shown in FIG. 5, having no argument angle modulation and a fixed argument magnitude modulation.

Accordingly, with the argument angle modulation function 125 a strong promotion of the relative amount of light in the focal point 122 for far vision is achieved.

FIG. 13a shows a height profile or height function H(r) 130 according to equation (6) above, as a function of the radial distance r of a diffraction grating in an example of a trifocal intraocular ophthalmic lens according to the present disclosure, modulated by a periodic argument magnitude modulation function α(r) 135, shown in FIG. 13b. The argument magnitude modulation function 135 is a periodic square wave function having a period equal to a period of the continuous periodic height function 130. The value of α(r) 135 is normalized with respect to the value of α=2.65718, as indicated along the vertical axis in FIG. 13b, and ranges between 1.4≥α(r)/2.65718≥0.7. The argument angle modulation function S(r)=0 for the height profile function 130. Reference numeral 131 refers to the outer circumference of the front surface 34 of the lens body 30 having a diffraction grating or relief 36 comprising the diffraction profile function H(r) 130.

In the example shown, a downward or trailing edge 136 of the argument magnitude modulation function 135 causes a transition 138 providing a displacement of the height profile function 130, i.e. the continuous periodic phase profile function of the diffraction grating, in a direction transverse to the at least one surface 34 of the lens body 30 and downwards, i.e. away from the outer circumference 131. The transition 138 is situated at the top or crest of the height profile function 130. An upward or leading edge 137 of the argument magnitude modulation function 135 causes a transition 139 providing a displacement of the height profile function 130, i.e. the continuous periodic phase profile function of the diffraction grating, in a direction transverse to the at least one surface 34 of the lens body 30 upwards, i.e. towards the outer circumference 131. The transition 139 is situated at the bottom or trough of the height profile function 130 and counteracts the displacement by the transition 138.

The light distribution achieved by the diffraction grating having the height profile 130 is shown in FIG. 13c. As can be seen from FIG. 13c, with the above-mentioned argument magnitude modulation function 135, relatively more light is distributed or coupled in the focal point for near vision 133 compared to the focal point for far vision 132. The amount of light distributed in the focal point for intermediate vision 134 is substantially equal to the amount of light distributed in the focal point for intermediate vision 54 of the height profile 50 shown in FIG. 5, having no argument angle modulation and a fixed argument magnitude modulation.

Accordingly, with the argument angle modulation function 135 a strong promotion of the relative amount of light in the focal point 133 for near vision is achieved. Those skilled in the art will appreciate that it is possible to combine periodic displacements of the height profile function in a direction transverse to the at least one surface 34, as described e.g. in FIGS. 10 and 11, with displacements of the height profile function parallel with the radial direction of the lens body, as described in FIGS. 12 and 13, to strengthen the effect of the tuning. In this way the relative intensities of the diffractive focal points can be changed very drastically.

From FIGS. 10a, 11a, 12a and 13a it can be seen that the transitions provided by the respective modulation functions shown in FIGS. 10b, 11b, 12b and 13c cause abrupt displacements in the height or phase profile functions, which displacements, in practice, may cause machining problems in manufacturing a lens having such a height profile.

In accordance with the present disclosure, it is advantageous to modulate the argument of the continuous periodic phase profile function causing periodic smoothened transitions or displacements in the continuous periodic phase profile function, i.e. the corresponding height profile or optical transfer function of the diffraction grating comprised by the continuous periodic phase profile function.

Figures 14A, 14B:
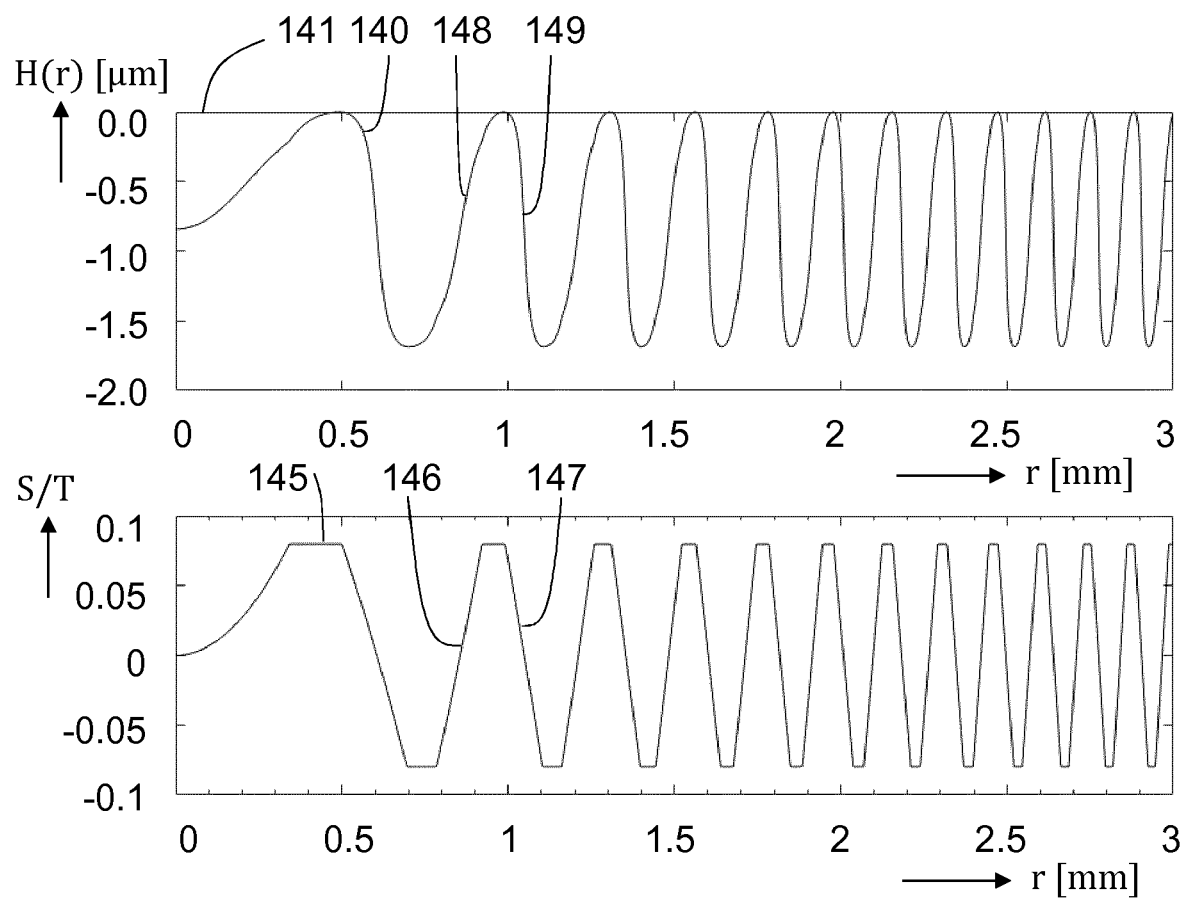

FIG. 14a shows a height profile or height function H(r) 140 according to equation (6) above, as a function of the radial distance r of a diffraction grating in an example of a trifocal intraocular ophthalmic lens according to the present disclosure, modulated by a periodic argument angle modulation function S(r) 145, shown in FIG. 14b. Different from the square wave argument angle modulation function 105 shown in FIG. 10b, the periodic argument angle modulation function S(r) 145 is a trapezoidal function having a period equal to a period of the continuous periodic height function 140. The maximum value of S(r) 145 ranges between $S=\pm 0.08*T$, as indicated along the vertical axis in FIG. 14b. Reference numeral 141 refers to the outer circumference of the front surface 34 of the lens body 30 having a diffraction grating or relief 36 comprising the diffraction profile function H(r) 140.

In the example shown, an upward or leading edge 146 of the argument angle modulation function 145 causes a smooth transition 148 providing a linear gradual displacement of the height profile function 140, i.e. the continuous periodic phase profile function of the diffraction grating, in outward radial direction r of the lens body, situated at a leading edge or upward flank of the height profile function 140. A downward or trailing edge 147 of the argument angle modulation function 145 causes a transition 149 providing a linear gradual displacement of the height profile function 140 in inward radial direction of the lens body, counteracting the displacement by the transition 148, and situated at a trailing edge or downward flank of the height profile function 140. The transitions provided by the S(r) function 145 provide a promotion of the light distributed in the focal point for far vision.

Figures 15A, 15B:
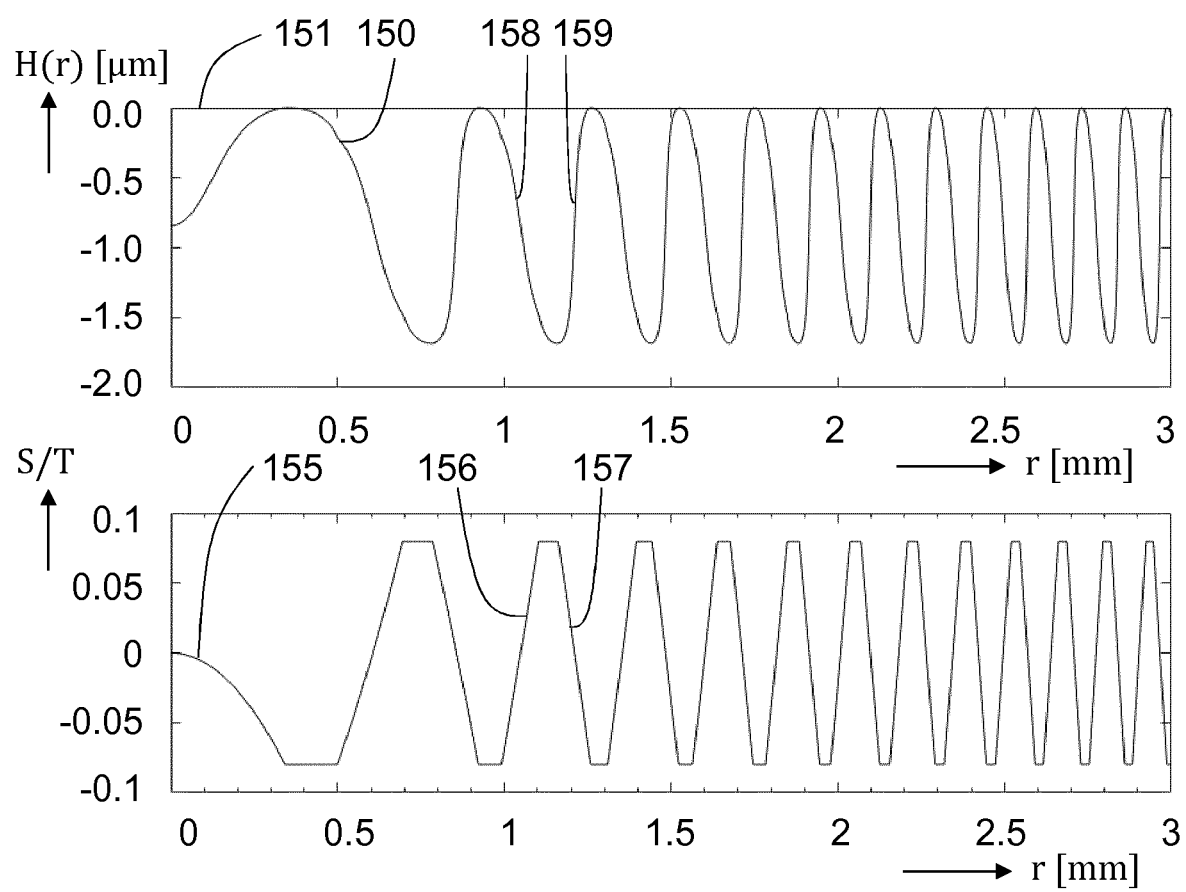

FIG. 15a shows a height profile or height function H(r) 150 according to equation (6) above, as a function of the radial distance r of a diffraction grating in an example of a trifocal intraocular ophthalmic lens according to the present disclosure, modulated by a periodic argument angle modulation function S(r) 155, shown in FIG. 15b. Different from the square wave argument angle modulation function 115 shown in FIG. 11b, the periodic argument angle modulation function S(r) 155 is a trapezoidal function having a period equal to a period of the continuous periodic height function 150. The maximum value of S(r) 155 ranges between $S=\pm 0.08*T$, as indicated along the vertical axis in FIG. 15b. Reference numeral 151 refers to the outer circumference of the front surface 34 of the lens body 30 having a diffraction grating or relief 36 comprising the diffraction profile function H(r) 150.

In the example shown, an upward or leading edge 156 of the argument angle modulation function 155 causes a smooth transition 158 providing a linear gradual displacement of the height profile function 150, i.e. the continuous periodic phase profile function of the diffraction grating, in outward radial direction r of the lens body, situated at a trailing edge or downward flank of the height profile function 150. A downward or trailing edge 157 of the argument angle modulation function 155 causes a smooth transition 159 providing a linear gradual displacement of the height profile function 150 in inward radial direction of the lens body, counteracting the displacement by the transition 118, and situated at a leading edge or upward flank of the height profile function 110. The transitions provided by the S(r) function 155 provide a promotion of the light distributed in the focal point for near vision.

By introducing periodic, smoothened transitions 148, 149 and 158, 159 in the continuous periodic phase profile functions, i.e. the corresponding height profiles 140, 150, respectively, manufacturing of an optical transfer function comprising such a phase profile function does not constitute a machining problem. By smoothening of the transitions, none or negligible artefacts are introduced in the diffraction grating, such that the properties of the tuned lens comprising a continuous periodic phase profile function with respect to less unwanted optical effects like stray light, chromatic aberration, halos, glare, scattering and the like, are maintained.

Those skilled in the art will appreciate that the argument magnitude modulation functions 125 and 135, shown in FIGS. 12b and 13b, respectively, may also be replaced with trapezoidal argument magnitude modulation functions, thereby providing smooth transitions, i.e. gradual displacements in a direction transverse to the surface of the lens body comprising a respective diffraction grating (not shown). In accordance with the present disclosure, other periodic argument angle and/or magnitude functions comprising one of a continuous function, a continuous trigonometric function, a triangle function, etc. may be applied, providing non-linear gradual displacements, for example.

FIG. 16a shows, by way of example, a height profile or height function H(r) 160 according to equation (6) above, as a function of the radial distance r of a diffraction grating in an example of a trifocal intraocular ophthalmic lens according to the present disclosure, modulated by a periodic argument angle modulation function S(r) 165, shown in FIG. 16b. Different from the linear smoothing shown in FIG. 15, in this example smoothing is provided by cubic spline interpolation. The argument magnitude modulation is provided at a so-called baseline phase value, chosen at $S=0.33*T$, while the maximum value of S(r) ranges between $0.41*T \geq S(r) \geq 0.25*T$, as indicated along the vertical axis in FIG. 16b. Reference numeral 161 refers to the outer circumference of the front surface 34 of the lens body 30 having a diffraction grating or relief 36 comprising the diffraction profile function H(r) 160. It will be appreciated that other baseline phase values may be selected.

In the example shown, a downward or trailing edge 166 of the argument angle modulation function 165 causes a smooth transition 168 providing a linear gradual displacement of the height profile function 160, i.e. the continuous periodic phase profile function of the diffraction grating, in outward radial direction r of the lens body, situated at a leading edge or upward flank of the height profile function 160. An upward or leading edge 167 of the argument angle modulation function 165 causes a smooth transition 169 providing a linear gradual displacement of the height profile function 160 in inward radial direction of the lens body, counteracting the displacement by the transition 168, and situated at a trailing edge or downward flank of the height profile function 160. The transitions provided by the S(r) function 165 provide a promotion of the light distributed in the focal point for near vision 163 compared to the focal point of far vision 162, shown in the intensity or light energy distribution diagram of FIG. 16c. reference numeral 164 refers to the amount of light distributed in the focal point for intermediate vision.

Those skilled in the art will appreciate that the argument angle modulation functions and the argument magnitude modulation functions shown in the previous Figures may be mutually interchanged and combined for providing, i.e. tuning of, an initially designed or selected continuous periodic phase or height profile function to arrive at a target or required light distribution in the target focal points.

The present disclosure is particularly suitable for providing a pupil dependent light distribution in the target focal points. This can be achieved in several manners, by suitable argument modulation of the continuous periodic phase profile function.

FIG. 17a shows, by way of example, a height profile or height function H(r) 170 according to equation (6) above, as a function of the radial distance r of a diffraction grating in an example of a trifocal intraocular ophthalmic lens according to the present disclosure, modulated by a periodic argument angle modulation function S(r) 175, shown in FIG. 17b. In this example, the periodic argument angle modulation function S(r) 175 comprises a first part, designated by reference numeral 176, extending over a radial distance of 1.7 mm from the optical axis, and a second part 177 extending from a radial distance of 1.7 mm outwards to the circumference of the lens body.

The first part 176 of the argument angle modulation function is comprised of a trapezoidal function having a period equal to a period of the continuous periodic height function 170, providing smooth transitions at the leading/trailing edges of the height profile function 170. In this first part, the value of S(r) ranges between S=±0.02*T, as indicated along the vertical axis in FIG. 17b.

The second part 177 of the argument angle modulation function is comprised of a trapezoidal function having a period equal to a period of the continuous periodic height function 170, likewise providing smooth transitions at the leading/trailing edges of the height profile function 170. In this second part, the value of S(r) ranges between S=±0.1*T, as indicated along the vertical axis in FIG. 17b.

FIGS. 17c-17f show intensity profiles for light partly incident at the lens body for several distances from the optical axis, thereby mimicking several pupil distances. FIG. 17c refers to a pupil diameter of 3 mm, FIG. 17d refers to a pupil diameter of 3.75 mm, FIG. 17e refers to a pupil diameter of 4.5 mm, and FIG. 17f refers to a pupil diameter of 6 mm. A pupil diameter of about 3 mm corresponds to a situation wherein the amount of light in the focus on near vision should be relatively enhanced, whereas a pupil diameter of about 6 mm corresponds to a situation wherein relative more light for the focus on far vision is preferred.

In the FIGS. 17c-17f, the intensity values are shown normalized with respect to the intensity for intermediate vision, i.e. at 20 D, indicated by In. The focal point for near vision is set at 21.5 D and the focal points for far vision is set at 18.5 D. For each intensity diagram, the light distribution ratio R of the amount of light coupled into focal points for far and near vision is indicated, that is R=In-far/In-near. If R equals 1, an equal amount of light is coupled into the diffractive focal points. For R<1 relatively more light is distributed into the focal point for near vision compared to the focal point for far vision. For R>1 relatively more light is distributed into the focal point for far vision compared to the focal point for near vision.

From the simulated normalized light intensities and the light distribution ratios calculated, it can be seen that the first part 176 of the argument angle modulation function 175 compared to the second part 177 thereof, emphasizes or promotes near vision for small pupil diameters, i.e. 3 mm and 3.75 mm, providing R values of 1.08 and 1.04, respectively, whereas far vision is emphasized or promoted by the second part 177 for larger pupil diameters, i.e. 4.5 mm and 6 mm, providing R values of 1.18 and 1.46, respectively.

FIG. 18a shows, by way of example, a height profile or height function H(r) 180 according to equation (6) above, as a function of the radial distance r of a diffraction grating in an example of a trifocal intraocular ophthalmic lens according to the present disclosure, modulated by a periodic argument angle modulation function S(r) 185, shown in FIG. 18b. In this example, the periodic argument angle modulation function S(r) 185 is comprised of a trapezoidal function having a period equal to a period of the continuous periodic height function 180, providing smooth transitions at the leading/trailing edges of the height profile function 180. The value of S(r) 185 exponentially increases in radial direction outwards to the circumference of the lens body, from a value S=0 to S=±0.1*T, as indicated along the vertical axis in FIG. 18b.

FIGS. 18c-18f show normalized intensity profiles for light partly incident at the lens body for several distances from the optical axis, in accordance with FIGS. 17c-17f, respectively. From the simulated normalized light intensities and the calculated light distribution ratios R, it can be seen that the argument angle modulation 185 moderately emphasizes or promotes near vision for the small pupil diameter of 3 mm, providing an R value of 1.74, compared to the R value of 1.90 for a pupil diameter of 6 mm, promoting far vision.

FIG. 19a shows, by way of example, a height profile or height function H(r) 190 according to equation (6) above, as a function of the radial distance r of a diffraction grating in an example of a trifocal intraocular ophthalmic lens according to the present disclosure, modulated by a periodic argument angle modulation function S(r) 195, shown in FIG. 19b. In this example, the periodic argument angle modulation function S(r) 195 is comprised of a trapezoidal function having a period equal to a period of the continuous periodic height function 190, providing smooth transitions at the leading/trailing edges of the height profile function 190. The value of S(r) 195 decreases exponentially in radial direction outwards to the circumference of the lens body, with respect to a baseline phase shift of S=0.33*T, from a value 0.38*T≥S(r)≥0.2*T, as indicated along the vertical axis in FIG. 19b.

FIGS. 19c-19f show normalized intensity profiles for light partly incident at the lens body for several distances from the optical axis, in accordance with FIGS. 17c-17f, respectively.

From the simulated normalized light intensities and the calculated light distribution ratios R, it can be seen that the argument angle modulation 195, contrary to the previous examples, promotes or emphasizes far vision for the smaller pupil diameters of 3 mm and 3.75 mm, providing R values of 1.6 and 1.67, respectively. Near vision is enhanced for the larger pupil diameters compared to the smaller pupil sizes, providing respective R values of 1.44 for a pupil diameter of 4.5 mm and 1.27 for a pupil diameter of 6 mm. It will be appreciated that this type of lens constitutes a special case and may be used for providing non-conventional power corrections.

The embodiments of the invention described and shown in FIGS. 18*a-f* and 19*a-f* have the advantage of providing gradually varying intensity distributions for different pupil sizes without an abrupt change between different zones as shown in FIG. 17*b*, for example, thereby providing less jarring and, accordingly, an enhanced experience for the user.

FIG. 20*a* shows, by way of example, a height profile or height function H(r) 200 according to equation (6) above, as a function of the radial distance r of a diffraction grating in an example of a trifocal intraocular ophthalmic lens according to the present disclosure, modulated by a periodic argument angle modulation function S(r) 205, shown in FIG. 20*b*. In this example, the periodic argument angle modulation function S(r) 200 comprises a first part, designated by reference numeral 206, extending over a radial distance of 1.5 mm from the optical axis, and a second part 207 extending from a radial distance of 1.5 mm outwards to the circumference of the lens body.

The first part 206 of the argument angle modulation function 205 is comprised of a trapezoidal function having a period equal to a period of the continuous periodic height function 200, providing smooth transitions at the leading/trailing edges of the height profile function 200. In this first part, the value of S(r) decreases exponentially in radial direction outwards to the circumference of the lens body, with respect to a baseline phase shift of S=0.33*T. The second part 207 of the argument angle modulation function 205 is comprised of a trapezoidal function having a period equal to a period of the continuous periodic height function 200, likewise providing smooth transitions at the leading/trailing edges of the height profile function 170. In this second part, the value of S(r) increases exponentially in radial direction outwards to the circumference of the lens body, with respect to the baseline phase shift of S=0.33*T. In the first part, the maximum value of S(r) 205 ranges between 0.44*T≥S(r)≥0.28*T, and in the second part 207 between S=±0.20*T, as indicated along the vertical axis in FIG. 20*b*.

FIGS. 20*c*-20*f* show normalized intensity profiles for light partly incident at the lens body for several distances from the optical axis, in accordance with FIGS. 17*c*-17*f*, respectively. From the simulated normalized light intensities and the calculated light distribution ratios R, it can be seen that the argument angle modulation 205, strongly promotes the light distribution in the focal point for near vision for the smaller pupil diameters of 3 mm and 3.75 mm, as well for a pupil diameter of 4.5 mm. providing R values of 0.68, 0.89 and 0.93, respectively. Far vision is slightly enhanced for the larger pupil diameter of 6 mm compared to the smaller pupil sizes, providing a respective R value of 1.08.

FIG. 21*a* shows a height profile or height function H(r) 210 according to equation (6) above, as a function of the radial distance r of a diffraction grating in an example of a trifocal intraocular ophthalmic lens according to the present disclosure, modulated by a periodic argument magnitude modulation function α(r) 216, shown in FIG. 21*b* and an argument angle modulation function S(r) 215.

The argument magnitude modulation function 216 is as stepwise or piecewise increasing function in radial outward direction of the lens body. The width of the pieces or steps is equal to the period of the continuous periodic height function 210. The value of α(r) 216 is normalized with respect to the value of α=2.65718, as indicated along the vertical axis in FIG. 21*b*, and ranges between 2≥α(r)/2.65718≥0.9. In the example shown, the argument magnitude modulation function 216 causes a periodic increase of the height of the height profile or height function 210 with increasing distance from the optical axis, having the effect of an apodization of the height profile 210.

The argument angle modulation function S(r) 215 is comprised of a trapezoidal function having a period equal to a period of the continuous periodic height function 180, providing smooth transitions at the leading/trailing edges of the height profile function 210. The value of S(r) 215 exponentially increases in radial direction outwards to the circumference of the lens body, from a value S=0 to S=±0.1*T, as indicated along the vertical axis in FIG. 21*c*.

FIG. 21*h* shows the light distribution or intensity profile for a lens comprising a diffraction grating having the height profile function 210. As can be seen from FIG. 21*h*, due to the argument angle modulation function S(r) 215 the amount of incident light distributed in the focal point 212 for far vision strongly exceeds the amount of incident light coupled into the focal point 213 for near vision. Further, compared to the intensity profile of FIG. 5*b*, for example, the amount of light in the focal point 214 for intermediate vision is reduced, due to the angle magnitude modulation function α(r) 216.

FIGS. 21*d*-21*g* show the normalized intensity profiles for light partly incident at the lens body for several distances from the optical axis, in accordance with FIGS. 17*c*-17*f*, respectively. From the simulated normalized light intensities and the calculated light distribution ratios R, it can be seen that the argument magnitude modulation function 216 strongly promotes or emphasizes far vision for all the pupil diameters of 3 mm, 3.75 mm, 4.5 and 6 mm, providing relative high R values of 2.03, 2.07, 2.05 and 2.13, respectively, compared to the R values of the previous examples.

From the normalized intensity profiles in FIGS. 21*f* and 21*g* it can be seen that the amount of light distributed in the focal point for intermediate vision reduces with increasing α(r) 216.

FIG. 22*a* shows a height profile or height function H(r) 220 according to equation (6) above, as a function of the radial distance r of a diffraction grating in an example of a trifocal intraocular ophthalmic lens according to the present disclosure, modulated by a periodic argument angle modulation function S(r) 225 shown in FIG. 22*b*, which periodic argument angle modulation function S(r) 225 is equal to the periodic argument angle modulation function S(r) 215, shown in FIG. 21*b*. Further, height apodization is applied at the height profile function 220, by an amplitude modulation function A(r) that exponentially increases with the radial distance to the optical axis of the lens (not shown). Note that the height profile function 220 is drawn on larger scale compared to the height profile functions of the previous examples.

From the normalized intensity profiles shown in FIGS. 22*c*-22*f* it can be derived, among others, that that the amount of incident light distributed in the focal point for intermediate vision reduces with increasing amplitude modulation A(r). The calculated light distribution ratios R show that near vision is relatively promoted for the smaller pupil diameters of 3 mm and 3.75 mm, respectively R=1.97 and R=2.01, whereas far vision is promoted for the larger pupil diameters of 4.5 and 6 mm, providing relative high R values of 2.05 and 2.27, respectively.

Hence, by the example profiles in FIGS. 21a and 22a, it is demonstrated that by apodization, either by one or both of argument magnitude modulation and amplitude modulation, the amount of light distributed in the focal point for intermediate vision, i.e. the refractive focal point, can be effectively tuned. Tuning of the light distribution in the diffractive focal points, inclusive pupil dependent tuning, has been demonstrated by the various examples of argument angle modulation.

Further, it has been observed that apodization using argument magnitude modulation, for achieving a similar effect in terms of tuning, requires less increase in height of the height function H(r) in radial direction of the lens body and less absolute height difference of the height function over the lens body from the optical axis to the circumference of the lens body, compared to apodization by amplitude modulation. Less absolute height difference is preferred from a manufacturing point of view. Further, such a profile is less sensitive for accumulation of dust, dirt and moisture and the like. Accordingly, apodization by argument magnitude modulation is preferred above amplitude modulation of the height function or height profile.

Although in the previous examples tuning of the light distribution in the focal points of a lens comprising a diffraction grating having a height profile in accordance with the continuous periodic phase profile function based on equation (6) above has been shown, the teachings of the present disclosure are not limited to this particular type of continuous periodic phase profile function.

Figure 23A:
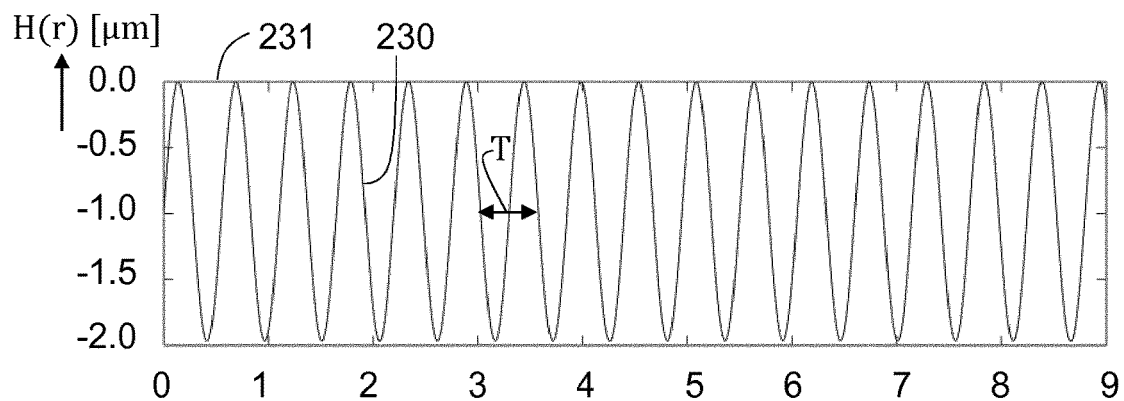
Figure 23B:
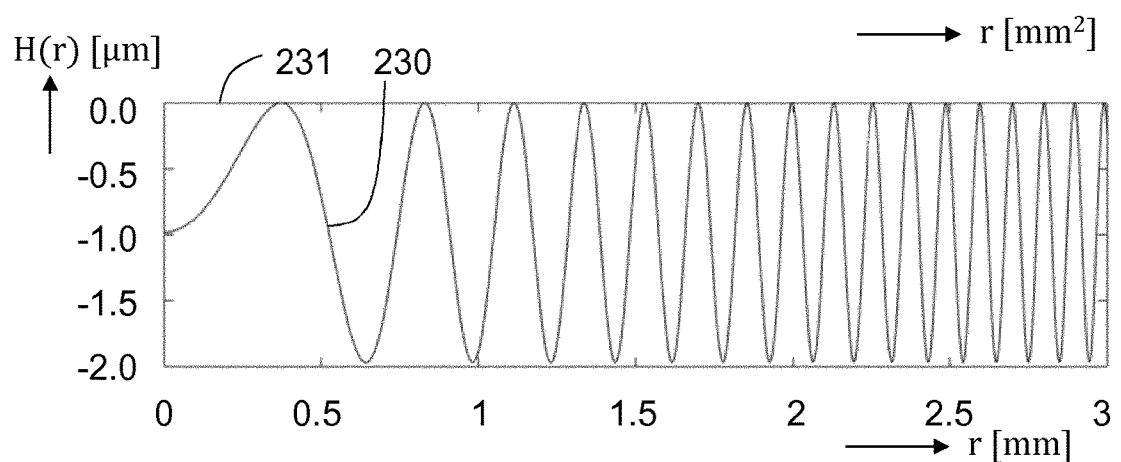

FIGS. 23a and 23b illustrate, by way of example, the height profile or height function H(r) of a true sine wave continuous periodic phase profile function in accordance with equation (7) below:

$$H(r) = A(r) * \frac{\lambda}{n - n_m} * \sin\left(\frac{2\pi\{r^2 - S(r)\}}{T}\right) \quad (7)$$

wherein:

H(r) height profile of the lens, [nm],

A(r) is amplitude modulation function of the continuous periodic phase profile function in radial direction of the lens body, $\lambda$ is the design wavelength of the lens, [nm], n is the index of refraction of the lens body, $n_m$ is the index of refraction of the medium surrounding the lens body S(r) is argument angle modulation function in $r^2$ space, [mm$^2$], and T is a period or pitch of the diffraction grating in $r^2$ space, [mm$^2$].

FIG. 23a shows the height profile or height function H(r) 230 in $r^2$ space, expressed in mm$^2$ and FIG. 23b shows the same height function 230 along a linear scale as function of the radial distance r. In this example, the argument angle modulation function S(r)=0, i.e. no phase shift or argument angle modulation.

The height of the height profile H(r) is depicted at μm scale along the vertical axis. The optical axis, running through the center of the lens body, is assumed to be at a radial position r=0, whereas the radial distance r measured in outward direction from the optical axis is expressed in mm along the vertical axis. Reference numeral 231 refers to the outer circumference of the front surface 34 of the lens body 30 having a diffraction grating or relief 36 comprising the diffraction profile function H(r) 230. See FIGS. 2a and 2b.

In this design, the design wavelength $\lambda$ of the lens is assumed 550 nm, the index of refraction n of the lens body is set to 1.4618, and the index of refraction $n_m$ of the medium surrounding the lens body is assumed 1.336. The amplitude modulation function A(r)=0.225. In the case of A(r)=0.5 the maximum phase retardation of 1 wavelength $\lambda$ is obtained. The period T=0.55 mm$^2$ in $r^2$ space.

Figure 23C:
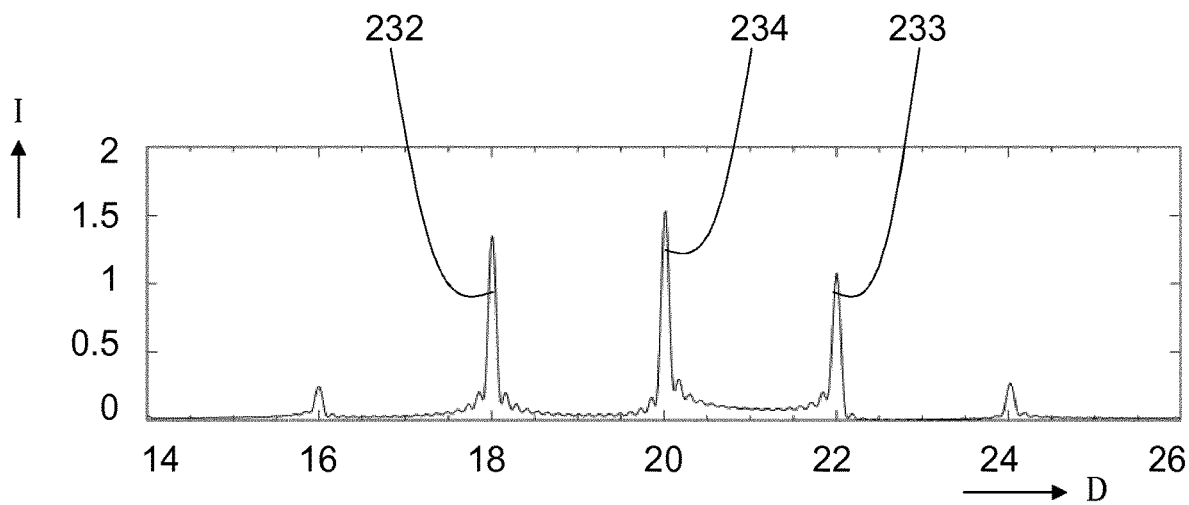

FIG. 23c shows a computer simulated light intensity distribution of a biconvex lens body 31 of an ophthalmic lens 30 of the type shown in FIGS. 2a, 2b, comprising a diffraction grating having the height profile 230. In the intensity profile, the intensity I of the diffracted light is depicted in arbitrary units along the vertical axis as a function of the optical power in diopter, D, depicted along the horizontal axis.

For illustration purposes, the lens is designed for targeting a zero order focal point at 20 diopter, D, and first order focal points at 22 D and 18 D, symmetrically positioned with respect to the zero order. That is, providing a focal point for intermediate vision 234 at 20 D for the zero order focal point, providing a focal point for far vision 232 at 18 D by diffraction order −1, and providing a focal point for near vision 233 at 22 D by the +1 diffraction order.

FIG. 24a shows, by way of example, a height profile or height function H(r) 240 according to equation (7) above, as a function of the radial distance r of a diffraction grating in an example of a trifocal intraocular ophthalmic lens according to the present disclosure, modulated by a periodic argument angle modulation function S(r) 245 in accordance with the present disclosure, shown in FIG. 24b. In this example, the periodic argument angle modulation function S(r) 245 comprises a first part, designated by reference numeral 246, extending over a radial distance of 1.75 mm from the optical axis, and a second part 247 extending from a radial distance of 1.75 mm outwards to the circumference of the lens body.

The first part 246 of the argument angle modulation function is comprised of a trapezoidal function having a period equal to a period of the continuous periodic height function 240, providing smooth transitions at the leading/trailing edges of the height profile function 240. In this first part, the value of S(r) ranges between S=±0.045*T, as indicated along the vertical axis in FIG. 24b.

The second part 247 of the argument angle modulation function is comprised of a trapezoidal function having a period equal to a period of the continuous periodic height function 240, likewise providing smooth transitions at the leading/trailing edges of the height profile function 240. In this second part, the value of S(r) ranges between S=±0.1*T, as indicated along the vertical axis in FIG. 24b.

FIGS. 24c-24f show normalised intensity profiles for light partly incident at the lens body comprising the height function 240, for several distances from the optical axis, in accordance with FIGS. 17c-17f. From the simulated normalized light intensities and the light distribution ratios calculated, it can be seen that the first part 246 of the argument angle modulation function 245 emphasizes or promotes near vision for small pupil diameters, i.e. 3 mm and 3.75 mm, providing R values of 0.92 and 0.90, respectively, whereas far vision is emphasized or promoted for larger pupil diameters, i.e. 4.5 mm and 6 mm, providing R values of 1.05 and 1.24, respectively, by the second part 247.

The optical transfer function or light transmission function in the present disclosure may have varying light transmission properties in radial direction r of the lens. In particular, wherein over a distance of about 2-3 mm in outward direction from the center of the lens the optical transfer function or light transmission function has a phase profile providing trifocal properties, while comprising bifocal properties having from a radial distance of about 2-3 mm to the circumferential edge of the lens a about r=5-7 mm. See FIG. 2a.

It is further noted that the teachings illustrated above are equally applicable for designing a multifocal ophthalmic lens having an asymmetrical diffraction grating and/or four target focal points, i.e. a so called quad-focal lens, or even five target focal points, i.e. a so-called penta-focal lens, for example.

Figure 25A:
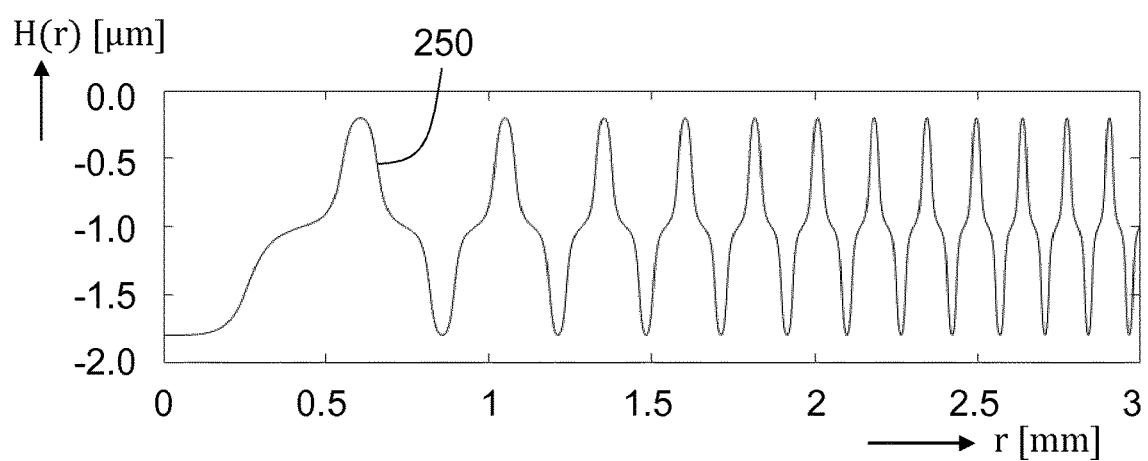

FIG. 25 illustrates, by way of example, a continuous periodic height profile function H(r) of a penta-focal lens along a linear scale as function of the radial distance r, comprising a diffraction grating, based on the continuous periodic phase profile function in accordance with equation (8) below:

$$\phi(r) = A(r) * \text{atan2}\left(2*\gamma(r)*\cos\left(2*\pi*\frac{r^2-S(r)}{T}\right), 1-2*\delta(r)*\cos\left(4*\pi*\frac{r^2-S(r)}{T}\right)\right) \quad (8)$$

wherein:

$\phi(r)$ is a continuous periodic phase profile function of the diffraction grating, r is the radial distance or radius outwardly from the optical axis of the lens body, [mm], atan 2 refers to the 2-argument arctangent, A(r) is an amplitude modulation function of the continuous periodic phase profile function in radial direction of the lens body, $\gamma(r)$ and $\delta(r)$ are argument modulation functions, S(r) argument angle modulation function in $r^2$ space, [mm$^2$], and T period or pitch of the diffraction grating in $r^2$ space, [mm$^2$].

The continuous periodic phase profile function (8) is based on teachings of the present disclosure and the publication by Romero, Louis A, and Fred M. Dickey, "Theory of optimal beam splitting by phase gratings. II. Square and hexagonal gratings." JOSA A 24.8 (2007): 2296-2312.

Figure 25B:
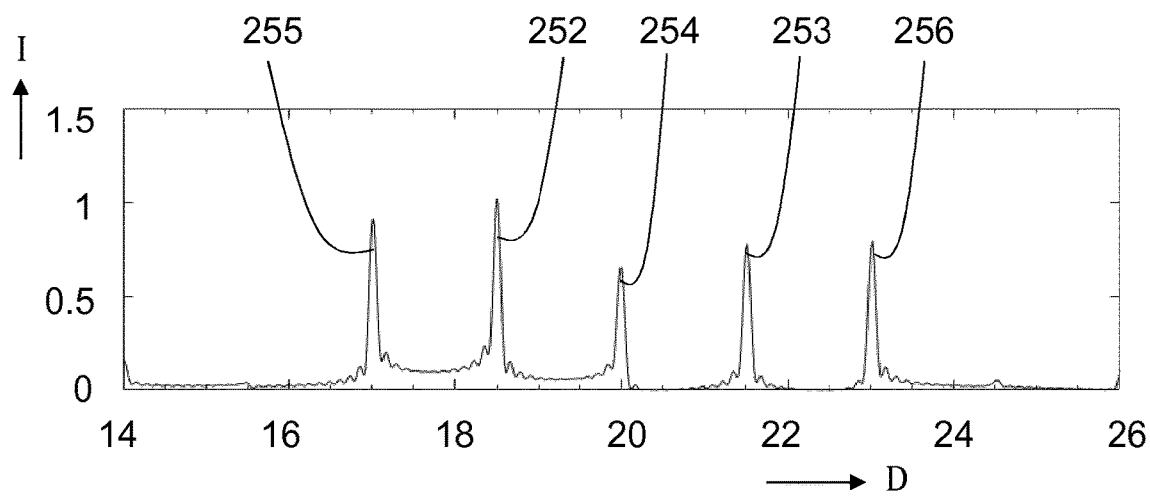

The amount of light diffracted by the lens having a diffraction profile comprising the height profile H(r) 250 is shown in the intensity simulation diagram of FIG. 25b. Reference numeral 254 refers to diffraction order 0, providing a focal point for intermediate vision, reference numerals 252 and 255 refer to diffraction orders −1 and −2, respectively, providing focal points for far vision, and reference numerals 253 and 256 refer to the +1 and +2 diffraction orders, providing focal points for near vision. In the present decision, the focal point for intermediate vision is set at 20 D, the focal points for far vision are set at 18.5 D and 17 D, and the focal points for near vision are set at 21.5 D and 23 D.

In accordance with the present disclosure, the distribution of incident light in the focal points can be tuned by amplitude and argument modulation applied by one or more of A(r), S(r), $\gamma(r)$ and $\delta(r)$. For the example height function 250 the following settings apply: A(r)=1, S(r)=0, $\gamma(r)$=0.459 and $\delta(r)$=0.899, T=0.733 mm$^2$ in $r^2$ space, the design wavelength $\lambda$ of the lens is assumed 550 nm, the index of refraction n of the lens body is set to 1.4618, and the index of refraction $n_m$ of the medium surrounding the lens body is assumed 1.336.

Figure 26:
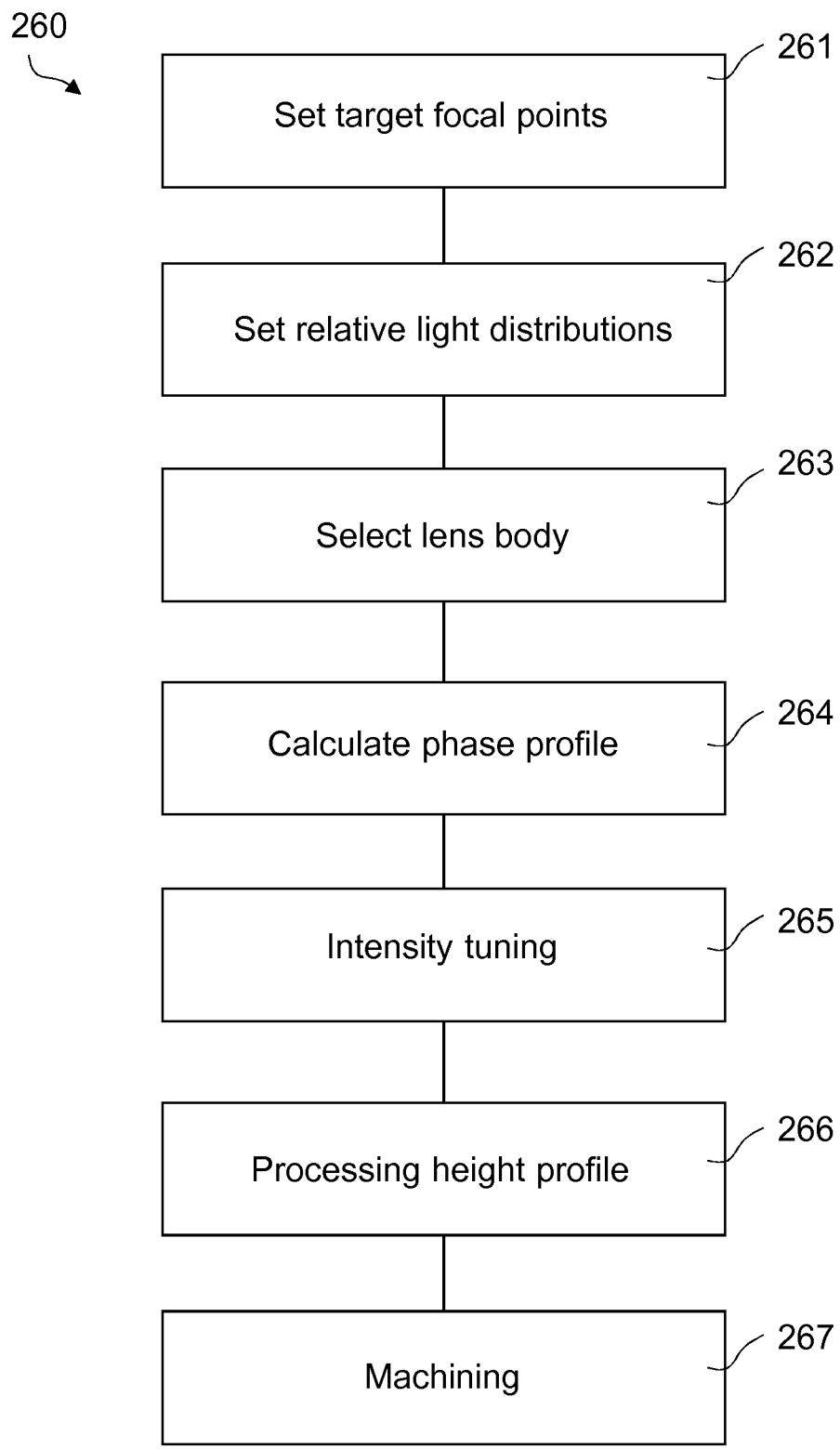
FIG. 26 illustrates, in a simplified flow diagram, steps of the method according to the present disclosure for manufacturing an ophthalmic multifocal lens.

The simplified flow diagram 260 in FIG. 26 illustrates generally steps of a method of manufacturing an ophthalmic multifocal lens, according to the present disclosure. The direction of the flow is from the top to the bottom of the drawing.

In a first step, at least target focal points for near, intermediate and far vision of the lens are set, i.e. block 261 "Set target focal points". In a second step, a target relative light distribution between the different focal points for different pupil sizes of a user are determined, i.e. block 262 "Set relative light distributions". The selected pupil sizes may, for example, range from diameter values of 0-3 mm, 0-4.5 mm, and 0-6 mm. Above 6 mm the lens may, for example, exhibit bifocal properties, i.e. relating to intermediate and far vision.

Next, a light transmissive lens body is selected, having a refractive focal point providing the target focal point for intermediate vision, i.e. block 263 "Select lens body". For providing the diffractive focal points, a continuous periodic phase profile function of a diffraction grating is calculated, either mathematically or numerically using a suitable programmed processor or computer. The continuous periodic phase profile function may, for example, be calculated for optimizing overall efficiency of light distribution in the target refractive and diffractive focal points over the complete lens body or for a pupil diameter size of 6 mm, for example, i.e. step 264 "Calculate phase profile".

In a next step, the calculated phase profile function is adapted for fine-tuning and/or smoothing of the desired or target optical properties of the lens, such as a desired relative light distribution among the target focal points, i.e. step 265 "Intensity tuning". This intensity tuning may be likewise processed by a suitably programmed processor or computer and may involve modulation as taught above and shown in the examples of FIGS. 6a-25b, for example. This, also for taking into account optical deviations in the target focal points and profile as a result of tolerances and the like in the machining or manufacturing of the lens, for example.

Finally, the geometric height profile of the diffraction grating is calculated for manufacturing the lens, i.e. step 266 "Processing height profile". Again using a suitably programmed processor. Finally, the height profile or height function of the diffraction grating specifying the height and position of the varies DOEs that extend at a surface of the lens concentric to the optical axis or center thereof is applied at the lens body by any of laser micro machining, diamond turning, 3D printing, or any other machining or lithographic surface processing technique, for example. That is step 267, "Machining".

The calculations in step 264 may be based on power spectrum calculations from a Fourier series representation of the diffraction grating, such that a summation of squared absolute values of Fourier coefficients of diffraction orders associated with the target focal points is maximum. As noted above, this calculation may be performed under the constraint of equal or weighted target light intensities in the target focal points.

The calculations of the continuous periodic phase profile function of the optical transfer function or light transmission function of the lens and the height profile of the diffraction grating in the method according to the present disclosure may be provided remote from the equipment for machining the lens. Particularities of the calculated diffraction grating may be forwarded to the machining equipment by a data transfer over a telecommunication network available in practice, such as the Internet (not shown).

Other variations to the disclosed examples and embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope thereof. Same reference signs refer to equal or equivalent elements or operations.

While various embodiments have been described, it will be apparent to those of ordinary skill in the art that many more embodiments and implementations are possible. Accordingly, the embodiments described herein are examples, not the only possible embodiments and implementations.

The subject-matter of the disclosure may also relate, among others, to the following aspects:

A first aspect relates to an ophthalmic multifocal lens, at least comprising focal points for near vision, intermediate vision and far vision, having a light transmissive lens body comprising an optical axis and providing a refractive focal point, and a periodic light transmissive diffraction grating extending concentrically in radial direction across at least part of at least one surface of said lens body providing a set of diffractive focal points, wherein said diffraction grating is designed to operate as an optical wave splitter for distributing light incident at said lens body in said refractive and diffractive focal points, said refractive focal point providing said focal point for intermediate vision and said diffractive focal points providing said focal points for near vision and far vision, said diffraction grating having an optical transfer function comprising a continuous periodic phase profile function extending in radial direction of said lens body, characterized in that said continuous periodic phase profile function comprises an argument modulated as a function of radial distance to said optical axis of said lens body, thereby tuning said distributing of light incident at said lens body.

A second aspect relates to the ophthalmic multifocal lens according to the first aspect, wherein said argument is modulated providing periodic smooth transitions in said continuous periodic phase profile function.

A third aspect relates to the ophthalmic multifocal lens according to the second aspect, wherein each transition extends over part of a period of said continuous periodic phase profile function, thereby tuning said light distribution in said diffractive focal points, wherein each transition comprises at least one of:
  a transition providing a displacement in said continuous periodic phase profile function in radial direction of said lens body, and
  a transition providing a displacement in said continuous periodic phase profile function in a direction transverse to said at least one surface of said lens body.

A fourth aspect relates to the ophthalmic multifocal lens according to the third aspect, wherein transitions providing a displacement in said continuous periodic phase profile function in radial direction of said lens body are arranged at a position of at least one of a leading and trailing edge or flank of said continuous periodic phase profile function, and transitions providing a displacement in said continuous periodic phase profile function in a direction transverse to said at least one surface of said lens body are arranged at a position of at least one of a crest and a trough of said continuous periodic phase profile function.

A fifth aspect relates to the ophthalmic multifocal lens according to any of aspects two three or four, wherein said transitions comprise at least one of:
  transitions providing an identical displacement in said continuous periodic phase profile function in a plurality of periods of said continuous periodic phase profile function,
  transitions providing a displacement in said continuous periodic phase profile function that increases over a plurality of periods of said continuous periodic phase profile function, and
  transitions providing a displacement in said continuous periodic phase profile function that decreases over a plurality of periods of said continuous periodic phase profile function.

A sixth aspect relates to the ophthalmic multifocal lens according to any of aspects two three or four or five, wherein said argument is modulated providing in a same period length of said continuous periodic phase profile function a first and second transition, spaced apart in radial direction of said lens body, wherein said second transition at least partly counteracts operation of said first transition.

A seventh aspect relates to the ophthalmic multifocal lens according to any of the previous aspects, wherein said argument is modulated in accordance with an argument modulation function, in particular wherein said argument modulation function is a periodic function having a period equal to a period of said continuous periodic phase profile function, comprising one of a continuous function, a continuous trigonometric function, a triangle function and a trapezoid function.

An eighth aspect relates to the ophthalmic multifocal lens according to any of the previous aspects, wherein said argument of said continuous periodic phase profile function is differently modulated across said lens body, thereby tuning said distributing of light incident at said lens body differently for different pupil sizes, in particular wherein said argument is modulated in a number of contiguous periods of said continuous periodic phase profile function covering at least one area of said lens body, wherein said number of contiguous periods and modulation of said argument differ at different areas across said lens body.

A ninth aspect relates to the ophthalmic multifocal lens according to any of the previous aspects, wherein said diffraction grating is arranged for operating as a wave splitter and comprises diffractive focal points at diffraction orders +1 and −1, and said continuous periodic phase profile function is expressed according to:

$$\phi(r) = A(r) * F\left[\alpha(r) * G\left(\frac{2\pi\{r^2 - S(r)\}}{T}\right)\right] + B(r)$$

wherein:
  $\phi(r)$ is continuous periodic phase profile function of said diffraction grating,
  r is radial distance or radius outwardly from said optical axis of said lens body, [mm], A(r) is an amplitude modulation function of said continuous periodic phase profile function in radial direction of said lens body, F [α*G] is a function in radial direction of said lens body providing said wave splitter operation, G (r) is a continuous periodic function in $r^2$ space, α(r) is an argument magnitude modulation function of G, S(r) is an argument angle modulation function of G in $r^2$ space, [$mm^2$], T is a period or pitch of said diffraction grating in $r^2$ space, [$mm^2$], and B(r) is an amplitude modulation function of said continuous periodic phase profile function, wherein at least one of said argument magnitude modulation function α(r) and said argument angle modulation function S(r) comprises said argument modulated as a function of the radial distance to said optical axis of said lens body.

A tenth aspect relates to the ophthalmic multifocal lens according to aspect nine, wherein said light distribution in said refractive and diffractive focal points is further tuned by an adaptation of at least one of said amplitude modulation function A(r) and said amplitude modulation function B(r) of said continuous periodic phase profile function.

An eleventh aspect relates to the ophthalmic multifocal lens according to aspects nine or ten, wherein F is an inverse tangent function, G is a sine function, said argument magnitude modulation function α(r) has a constant value ranging between 2.5 and 3, and said argument angle modulation function S(r) has a constant value ranging between $-0.5*T$ and $0.5*T$ in $r^2$ space, in particular wherein S(r) has a constant value ranging between $0.30*T$ and $0.50*T$ in $r^2$ space, more particular wherein S(r) has a constant value ranging between $-0.05*T$ and $-0.15*T$ in $r^2$ space, and even more in particular wherein $S(r)=0.42*T$ in $r^2$ space.

A twelfth aspect relates to the ophthalmic multifocal lens according to any of the previous aspects, wherein said argument of said continuous periodic phase profile function is modulated for providing first trifocal properties at a first area of said surface of said lens extending in radial direction and including said optical axis, said first trifocal properties emphasizing light distributed in said focal point for near vision, and providing second trifocal properties at a second area of said surface of said lens extending beyond said first area in radial direction of said lens towards a circumferential edge of said lens body, said second trifocal properties emphasizing light distributed in said focal point for far vision.

A thirteenth aspect relates to a method of manufacturing an ophthalmic multifocal lens, at least comprising focal points for near vision, intermediate vision and far vision, having a light transmissive lens body comprising an optical axis providing a refractive focal point, and a periodic light transmissive diffraction grating, extending concentrically in radial direction across at least part of a surface of said lens body providing a set of diffractive focal points, wherein said diffraction grating is designed to operate as an optical wave splitter for distributing light incident at said lens body in said refractive and diffractive focal points, said refractive focal point providing said focal point for intermediate vision and said diffractive focal points providing said focal points for near vision and far vision, said method comprising the steps of:
determining target focal points for near vision, intermediate vision and far vision;
determining a target light distribution of incident light in said target focal points;
providing said light transmissive lens body having a refractive focal point providing said target focal point for intermediate vision;
providing said diffraction grating having an optical transfer function comprising a continuous periodic phase profile function extending in radial direction of said lens body providing said target focal points for near vision and far vision and a distribution of light in said target focal points,
characterized by the steps of:
providing said continuous periodic phase profile function having a modular argument as a function of radial distance to said optical axis of said lens body,
tuning said distributing of light in said target focal points for providing said target light distribution by modulating said argument across said lens body, providing a modulated argument,
providing a height profile of said diffraction grating in accordance with said periodic phase profile function comprising said modulated argument, and
producing said ophthalmic multifocal lens by applying said diffraction grating in accordance with said height profile at said lens body.

A fourteenth aspect relates to the ophthalmic multifocal lens according to aspect thirteen, wherein said argument of said continuous periodic phase profile function is modulated for producing said ophthalmic multifocal lens in accordance with any of the aspects two through twelve.

A fifteenth aspect relates to the ophthalmic multifocal lens provided in accordance with to any of the previous aspects, arranged as one of a contact lens, an intraocular lens, an aphakic contact lens, an aphakic intraocular lens, and a spectacle lens.

The invention claimed is:

1. An ophthalmic multifocal lens, comprising: focal points for near vision, intermediate vision and far vision, having a light transmissive lens body comprising an optical axis and providing a refractive focal point, and a periodic light transmissive diffraction grating extending concentrically in a radial direction from said lens body across at least part of at least one surface of said lens body and providing a set of diffractive focal points, wherein said diffraction grating is configured to operate as an optical wave splitter for distribution of light incident at said lens body in said refractive and diffractive focal points, said refractive focal point providing said focal point for intermediate vision and said diffractive focal points providing said focal points for near vision and far vision, said diffraction grating having an optical transfer function comprising a continuous periodic phase profile function extending in the radial direction of said lens body, wherein said continuous periodic phase profile function comprises an argument modulated as a function of a radial distance to said optical axis of said lens body so as to tune said distribution of light incident at said lens body, wherein;
said argument is modulated to provide periodic smooth transitions in said continuous periodic phase profile function,
each of the transitions extends over part of a period of said continuous periodic phase profile function for tuning said light distribution in said diffractive focal points, and
transitions providing a displacement in said continuous periodic phase profile function in the radial direction of said lens body are arranged at a position of at least one of a leading edge, or a trailing edge, or a flank of said continuous periodic phase profile function, and transitions providing a displacement in said continuous periodic phase profile function in a direction transverse to said at least one surface of said lens body are arranged at a position of at least one of a crest or a trough of said continuous periodic phase profile function.

2. The ophthalmic multifocal lens according to claim 1, wherein each transition comprises at least one of:
a transition providing a displacement in said continuous periodic phase profile function in the radial direction of said lens body, or
a transition providing a displacement in said continuous periodic phase profile function in a direction transverse to said at least one surface of said lens body.

3. The ophthalmic multifocal lens according to claim 1, wherein said transitions comprise at least one of:
transitions providing an identical displacement in said continuous periodic phase profile function in a plurality of periods of said continuous periodic phase profile function,
transitions providing a displacement in said continuous periodic phase profile function that increases over a plurality of periods of said continuous periodic phase profile function, or
transitions providing a displacement in said continuous periodic phase profile function that decreases over a plurality of periods of said continuous periodic phase profile function.

4. The ophthalmic multifocal lens according to claim 1, wherein modulation of said argument provides, in a same period length of said continuous periodic phase profile function, a first and second transition, spaced apart in the radial direction of said lens body, wherein operation of said second transition at least partly counteracts operation of said first transition.

5. The ophthalmic multifocal lens according to claim 1, wherein said argument is modulated in accordance with an argument modulation function, wherein said argument modulation function is a periodic function having a period equal to a period of said continuous periodic phase profile function.

6. The ophthalmic multifocal lens according to claim 5, wherein said argument modulation function comprises one of a continuous function, a continuous trigonometric function, a triangle function or a trapezoid function.

7. The ophthalmic multifocal lens according to claim 1, wherein said argument of said continuous periodic phase profile function is differently modulated across said lens body to tune said distribution of light incident at said lens body differently for different pupil sizes.

8. The ophthalmic multifocal lens according to claim 7, wherein said argument is modulated in a number of contiguous periods of said continuous periodic phase profile function covering at least one area of said lens body, wherein said number of contiguous periods and modulation of said argument differ at different areas across said lens body.

9. The ophthalmic multifocal lens according to claim 1, wherein said diffraction grating is configured to operate as the optical wave splitter, to provide a plurality of diffractive focal points, comprising diffractive focal points at diffraction orders of +1 and −1.

10. The ophthalmic multifocal lens according to claim 1, wherein said continuous periodic phase profile function is expressed according to:

$$\phi(r) = A(r) * F\left[a(r) * G\left(\frac{2\pi\{r^2 - S(r)\}}{T}\right)\right] + B(r)$$

wherein:
ϕ(r) is continuous periodic phase profile function of said diffraction grating,
r is radial distance or radius outwardly from said optical axis of said lens body, [mm],
A(r) is an amplitude modulation function of said continuous periodic phase profile function in radial direction of said lens body,
F[α*G] is a function in radial direction of said lens body providing said wave splitter operation,
G(r) is a continuous periodic function in $r^2$ space,
α(r) is an argument magnitude modulation function of G,
S(r) is an argument angle modulation function of G in $r^2$ space, [$mm^2$],
T is a period or pitch of said diffraction grating in $r^2$ space, [$mm^2$], and
B(r) is an amplitude modulation function of said continuous periodic phase profile function,
wherein at least one of said argument magnitude modulation function α(r) or said argument angle modulation function S(r) comprises said argument modulated as a function of the radial distance to said optical axis of said lens body.

11. The ophthalmic multifocal lens according to claim 10, wherein said light distribution in said refractive and diffractive focal points is further tuned by an adaptation of at least one of said amplitude modulation function A(r) or said amplitude modulation function B(r) of said continuous periodic phase profile function.

12. The ophthalmic multifocal lens according to claim 10, wherein F is an inverse tangent function, G is a sine function, said argument magnitude modulation function α(r) has a constant value ranging between 2.5 and 3, and said argument angle modulation function S(r) has a constant value ranging between −0.5*T and 0.5*T in $r^2$ space.

13. The ophthalmic multifocal lens according to claim 10, wherein S(r) has a constant value ranging between 0.30*T and 0.50*T in $r^2$ space.

14. The ophthalmic multifocal lens according to claim 10, wherein S(r) has a constant value ranging between −0.05*T and −0.15*T in $r^2$ space.

15. The ophthalmic multifocal lens according to claim 10, wherein S(r)=0.42*T in $r^2$ space.

16. The ophthalmic multifocal lens according to claim 1, wherein said argument of said continuous periodic phase profile function is modulated for providing first trifocal properties at a first area of said surface of said ophthalmic multifocal lens extending in the radial direction and including said optical axis, said first trifocal properties emphasizing light distributed in said focal point for near vision, and providing second trifocal properties at a second area of said surface of said ophthalmic multifocal lens extending beyond said first area in the radial direction of said lens body towards a circumferential edge of said lens body, said second trifocal properties emphasizing light distributed in said focal point for far vision.

17. The ophthalmic multifocal lens according to claim 1, wherein said ophthalmic multifocal lens is configured as one of a contact lens, an intraocular lens, an aphakic contact lens, an aphakic intraocular lens, or a spectacle lens.

18. A method of manufacturing an ophthalmic multifocal lens comprising:
determining target focal points for near vision, intermediate vision and far vision;
determining a target light distribution of incident light in said target focal points;

providing a light transmissive lens body comprising an optical axis having a refractive focal point providing a target focal point for intermediate vision;

providing a periodic light transmissive diffraction grating extending concentrically in a radial direction across at least part of a surface of said lens body and providing a set of diffractive focal points, wherein said diffraction grating is configured to operate as an optical wave splitter for distributing light incident at said lens body in said refractive and diffractive focal points, said refractive focal point providing said focal point for intermediate vision and said diffractive focal points providing said focal points for near vision and far vision, said diffraction grating having an optical transfer function comprising a continuous periodic phase profile function extending in the radial direction of said lens body providing said target focal points for near vision and far vision and a distribution of light in said target focal points, providing said continuous periodic phase profile function having a modular argument as a function of radial distance to said optical axis of said lens body, tuning said distributing of light in said target focal points for providing said target light distribution by modulating said argument across said lens body, providing a modulated argument, providing a height profile of said diffraction grating in accordance with said periodic phase profile function comprising said modulated argument, and producing said ophthalmic multifocal lens by applying said diffraction grating in accordance with said height profile at said lens body.

19. The method according to claim 18, wherein said argument of said continuous periodic phase profile function is modulated for producing said ophthalmic multifocal lens.

* * * * *